United States Patent [19]
Itoh et al.

[11] Patent Number: 6,166,010
[45] Date of Patent: Dec. 26, 2000

[54] AZINE DERIVATIVES

[75] Inventors: Yoshiaki Itoh, Nagano; Tatsuya Ishida, Nagano-Ken; Yasuo Kikuchi, Nagano-Ken; Junji Suzuki, Nagano-Ken; Chiharu Morikawa, Nagano-Ken; Yokichi Tsukidate, Nagano-Ken; Kichizo Kudoh, Nagano-Ken, all of Japan; Graham Holmwood, Wuppertal, Germany; Udo Kraatz, Leverkusen, Germany; Ulrike Wachendorff-Neumann, Monheim, Germany; Christoph Erdelen, Leichlingen, Germany

[73] Assignees: Yashima Chemical Industry Co., LTD, Kanagawa, Japan; Bayer Aktiengesellschaft, Leverkusen, Germany

[21] Appl. No.: 08/274,940

[22] Filed: Jul. 14, 1994

[30] Foreign Application Priority Data

Jul. 21, 1993 [JP] Japan ................................. H5-200168
Dec. 2, 1993 [DE] Germany ............................ 43 41 065

[51] Int. Cl.⁷ ..................... C07D 263/14; C07D 263/12; C07D 413/04; A61K 31/535
[52] U.S. Cl. ..................... 514/228.8; 514/230.5; 544/88; 544/97; 544/90; 544/96; 544/71
[58] Field of Search ................... 544/90, 96, 88, 544/71; 514/230.5, 228.8

[56] References Cited

U.S. PATENT DOCUMENTS

| 3,397,201 | 8/1968 | Trepanier | 260/244 |
|---|---|---|---|
| 3,450,699 | 6/1969 | Seeliger et al. | 260/244 |
| 3,846,419 | 11/1974 | Seeliger et al. | 260/244 R |
| 4,144,211 | 3/1979 | Chamberlin et al. | 260/29.2 R |
| 5,538,967 | 7/1996 | Long | 514/226.8 |

FOREIGN PATENT DOCUMENTS

| 0226837 | 7/1987 | European Pat. Off. . | |
| 1478076 | 3/1967 | France . | |
| 1582751 | 9/1969 | France . | |
| 2158143 | 6/1973 | France . | |
| 2049160 | 4/1972 | Germany . | |
| 2185978 | 8/1987 | United Kingdom . | |
| 9414783 | 7/1994 | WIPO | C07D 265/08 |
| WO9414783 | 7/1994 | WIPO . | |
| WO 96/22286 | 7/1996 | WIPO . | |

OTHER PUBLICATIONS

Journal of the Chemical Society, No. 8, pp. 757/771–774; "A new stereospecific synthesis of 5,6–dihydro–4H–1,3–thiazines by polar . . . ", L. Abis et al; 1973 \*\*publication month not provided.
Derwent Abstract of Yamada et al., WO 9414783 (1994), CAS World Patents Index No. 94–234573/28.

Primary Examiner—John M. Ford
Assistant Examiner—King Lit Wong
Attorney, Agent, or Firm—Norris, McLaughlin & Marcus, P.A.

[57] ABSTRACT

The invention relates to the use of azine derivatives, some of which are known, of the formula

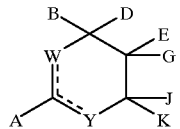

(I)

in which
A represents substituted phenyl, or represents in each case optionally substituted naphthyl, pyridyl, thienyl or pyrazolyl;
B represents hydrogen, alkyl or in each case optionally substituted phenyl, phenylalkyl, phenylalkenyl, phenoxyalkyl, phenylthioalkyl, phenylsulfinylalkyl or phenylsulfonylalkyl;
D represents hydrogen or alkyl;
E represents hydrogen, alkyl or in each case optionally substituted phenyl, phenylalkyl, phenoxyalkyl, phenylthioalkyl, phenylsulfinylalkyl or phenylsulfonylalkyl;
G represents hydrogen or alkyl;
J represents hydrogen or alkyl;
K represents hydrogen, alkyl or optionally substituted phenyl; or
B and D or D and G or E and G together represent optionally substituted alkanediyl, wherein one or two CH₂ groups are optionally replaced by O and/or S; and
W and Y are different and represent N, O or S, wherein the ring always contains an N atom,
for combating animal pests.

20 Claims, No Drawings

AZINE DERIVATIVES

The invention relates to the use of azine derivatives, some of which are known, for combating animal pests.

It is already known that certain azines, such as, for example, 3,6-bis-(2-chlorophenyl)-1,2,4,5-tetrazine have acaricidal properties (compare, for example, EP-A 0005912). However, the activity of these already known compounds is not completely satisfactory in all fields of use, especially when low amounts are used and at low concentrations.

It has now been found that the azine derivatives, some of which are known, of the formula (I)

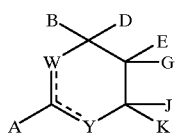

(I)

in which

A represents substituted phenyl, or represents in each case optionally substituted naphthyl, pyridyl, thienyl or pyrazolyl;

B represents hydrogen, alkyl or in each case optionally substituted phenyl, phenylalkyl, phenylalkenyl, phenoxyalkyl, phenylthioalkyl, phenylsulfinylalkyl or phenylsulfonylalkyl;

D represents hydrogen or alkyl;

E represents hydrogen, alkyl or in each case optionally substituted phenyl, phenylalkyl, phenoxyalkyl, phenylthioalkyl, phenylsulfinylalkyl or phenylsulfonylalkyl;

G represents hydrogen or alkyl;

J represents hydrogen or alkyl;

K represents hydrogen, alkyl or optionally substituted phenyl; or

B and D together represent optionally substituted alkanediyl, wherein one or two $CH_2$ groups are optionally replaced by O and/or S; or D and G together represent optionally substituted alkanediyl, wherein one or two $CH_2$ groups are optionally replaced by O and/or S; or E and G together represent optionally substituted alkanediyl, wherein one or two $CH_2$ groups are optionally replaced by O and/or S; and W and Y are different and represent N, O or S, wherein the ring always contains an N atom, are particularly suitable for combating animal pests, in particular arthropods and nematodes.

Depending on the nature of the substituents, the compounds of the formula (I) can be in the form of geometric and/or optical isomers or isomer mixtures of varying composition. The invention relates both to the pure isomers and to the isomer mixtures.

In formula (I), the broken line represents a double bond between the nitrogen atom and the adjacent carbon atom which carries the substituent A.

Surprisingly, the azines of the formula (I) used according to the invention show a considerably better activity against animal pests than the already known compounds which are the most similar in structure.

Formula (I) provides a general definition of the compounds which can be used according to the invention.

A preferably (preferentially) represents phenyl, which is monosubstituted to pentasubstituted in an identical or different manner by halogen, $C_1$–$C_6$-alkyl, $C_1$–$C_6$-alkoxy, $C_1$–$C_6$-alkylthio, $C_1$–$C_6$-halogenoalkyl, $C_1$–$C_6$-halogenoalkoxy, $C_1$–$C_6$-halogenoalkylthio, nitro or cyano;

or represents naphthyl, which is optionally monosubstituted to trisubstituted in an identical or different manner, substituents which may be mentioned being halogen, $C_1$–$C_6$-alkyl, $C_1$–$C_6$-alkoxy or $C_1$–$C_6$-halogenoalkoxy;

or represents pyridyl, which is optionally monosubstituted to trisubstituted in an identical or different manner, substituents which may be mentioned being halogen, $C_1$–$C_6$-alkyl, $C_1$–$C_6$-alkoxy, $C_1$–$C_6$-halogenoalkyl, $C_1$–$C_6$-halogenoalkoxy or cyano;

or represents thienyl, which is optionally monosubstituted to trisubstituted in an identical or different manner, substituents which may be mentioned being halogen or $C_1$–$C_6$-alkyl;

or represents pyrazolyl, which is optionally monosubstituted to trisubstituted in an identical or different manner, substituents which may be mentioned being halogen or $C_1$–$C_3$-alkyl.

B preferably represents hydrogen; or represents $C_1$–$C_6$-alkyl; or represents phenyl, benzyl, pheneth-1-yl, pheneth-2-yl, phenoxymethyl, phenylthiomethyl, phenylsulfinylmethyl, phenylsulfonylmethyl, phenylthioeth-1-yl, phenylsulfinyleth-1-yl, phenylsulfonyleth-1-yl, phenoxyeth-1-yl, phenoxyeth-2-yl or styryl, in each case optionally monosubstituted to pentasubstituted in an identical or different manner, phenyl substituents which may be mentioned in each case being halogen,
$C_1$–$C_{18}$-alkyl,
$C_1$–$C_8$-alkoxy-$C_1$–$C_8$-alkyl,
$C_1$–$C_8$-halogenoalkoxy,
$C_1$–$C_4$-halogenoalkyl,
$C_1$–$C_{18}$-alkoxy, which is optionally interrupted by a further 1 to 3 oxygen atoms,
$C_1$–$C_{18}$-alkylthio,
$C_1$–$C_8$-halogenoalkylthio,
tri-$C_1$–$C_8$-alkylsilyl,
phenyl-di-$C_1$–$C_8$-alkylsilyl,
3,4-difluoromethylenedioxo,
3,4-tetrafluoroethylenedioxo,
a fused-on benzo group,
a fused-on $C_3$–$C_4$-alkanediyl group,
benzyliminooxymethyl, which is optionally substituted by $C_1$–$C_4$-alkyl, $C_3$–$C_6$-cycloalkyl and/or halogen,
cyclohexyl or cyclohexyloxy, in each case optionally substituted by $C_1$–$C_6$-alkyl, $C_1$–$C_6$-alkoxy, cyclohexyl or phenyl;
pyridyloxy, which is optionally monosubstituted or disubstituted in an identical or different manner by halogen, $C_1$–$C_4$-alkyl or $C_1$–$C_4$-halogenoalkyl;
phenyl, phenyl-$C_1$–$C_6$-alkyl, phenoxy, phenylthio, phenyl-$C_1$–$C_6$-alkoxy or benzylthio,
in each case optionally monosubstituted to pentasubstituted in an identical or different manner by $C_1$–$C_{12}$-alkyl, halogen, $C_1$–$C_4$-halogenoalkyl, $C_1$–$C_{12}$-alkoxy, $C_1$–$C_6$-halogenoalkoxy, $C_1$–$C_6$-alkoxy-$C_1$–$C_6$-alkyl, $C_1$–$C_6$-alkoxy-ethyleneoxy, $C_1$–$C_6$-alkylthio and/or $C_1$–$C_6$-halogenoalkylthio.

D preferably represents hydrogen or methyl.

E preferably represents hydrogen, methyl or phenyl, phenyl-$C_1$–$C_6$-alkyl, phenoxy-$C_1$–$C_6$-alkyl, phenylthio-$C_1$–$C_6$-alkyl, phenylsulfinyl-$C_1$–$C_6$-alkyl or phenylsulfonyl-$C_1$–$C_6$-alkyl, in each case optionally monosubstituted to tetrasubstituted in an identical or different manner, possible substituents being the phenyl substituents mentioned above in the preferred definition of substituent B.

G preferably represents hydrogen or methyl.

J preferably represents hydrogen or methyl.

K preferably represents hydrogen or methyl, or represents phenyl, which can be monosubstituted to tetrasubstituted in an identical or different manner by the substituents mentioned for phenyl in connection with the preferred definition of B, or B and D together preferably represent 2- to 6-membered alkanediyl, which is optionally monosubstituted to tetrasubstituted in an identical or different manner, wherein one or two $CH_2$ groups are optionally replaced by O and/or S, possible substituents being: $C_1$–$C_4$-alkyl, and phenyl or a fused-on benzo group, in each case optionally monosubstituted to tetrasubstituted in an identical or different manner, possible substituents in each case being the substituents mentioned for phenyl in connection with the preferred definition of substituent B, or D and G together preferably represent 2- to 6-membered alkanediyl, which is optionally monosubstituted to tetrasubstituted in an identical or different manner, wherein one or two $CH_2$ groups are optionally replaced by O and/or S, possible substituents being: $C_1$–$C_4$-alkyl, and phenyl or a fused-on benzo group, in each case optionally monosubstituted to tetrasubstituted in an identical or different manner, possible substituents in each case being the substituents mentioned for phenyl in connection with the preferred definition of substituent B, or E and G together preferably represent 2- to 6-membered alkanediyl, which is optionally monosubstituted to tetrasubstituted in an identical or different manner, wherein one or two $CH_2$ groups are optionally replaced by O and/or S, possible substituents being: $C_1$–$C_4$-alkyl, and phenyl or a fused-on benzo group, in each case optionally monosubstituted to tetrasubstituted in an identical or different manner, possible substituents in each case being the substituents mentioned for phenyl in connection with the preferred definition of substituent B.

W and Y are different and also preferably represent N, O or S, the ring always containing an N atom.

A particularly preferably represents phenyl, which is monosubstituted to pentasubstituted in an identical or different manner by F, Cl, Br, $C_1$–$C_3$-alkyl, $C_1$–$C_3$-alkoxy, $C_1$–$C_3$-alkylthio, $C_1$–$C_2$-alkyl which is monosubstituted to pentasubstituted in an identical or different manner by F and/or Cl, $C_1$–$C_4$-alkoxy which is monosubstituted to pentasubstituted in an identical or different manner by F and/or Cl, $SCF_3$, $SCHF_2$, nitro or cyano;

or represents naphthyl, which is optionally monosubstituted to trisubstituted in an identical or different manner, substituents which may be mentioned being F, Cl, $C_1$–$C_6$-alkyl, $C_1$–$C_6$-alkoxy or $C_1$–$C_6$-alkoxy which is monosubstituted to trisubstituted in an identical or different manner by F and/or Cl;

or represents pyridyl, which is optionally monosubstituted to disubstituted in an identical or different manner, substituents which may be mentioned being F, Cl, $C_1$–$C_3$-alkyl, $C_1$–$C_3$-alkoxy, $CF_3$, $OCF_3$ or cyano; or represents thienyl, which is optionally monosubstituted to disubstituted in an identical or different manner, substituents which may be mentioned being Cl, Br, $CH_3$ or $C_2H_5$;

or represents pyrazolyl, which is optionally monosubstituted to trisubstituted in an identical or different manner, substituents which may be mentioned being F, Cl, Br or $C_1$–$C_3$-alkyl.

B particularly preferably represents hydrogen; or represents $C_1$–$C_4$-alkyl; or represents phenyl, benzyl, pheneth-1-yl, pheneth-2-yl, phenoxymethyl, phenylthiomethyl, phenylsulfinylmethyl, phenylsulfonylmethyl, phenylthioeth-1-yl, phenylsulfinyleth-1-yl, phenylsulfonyleth-1-yl, phenoxyeth-1-yl, phenoxyeth-2-yl, or styryl, in each case optionally monosubstituted to pentasubstituted in an identical or different manner, phenyl substituents which may be mentioned in each case being F, Cl, Br,
$C_1$–$C_{18}$-alkyl,
$C_1$–$C_6$-alkoxy-$C_1$–$C_8$-alkyl,
$C_1$–$C_8$-alkoxy which is monosubstituted to hexasubstituted in an identical or different manner by F and/or Cl,
$C_1$–$C_2$-alkyl which is monosubstituted to pentasubstituted in an identical or different manner by F and/or Cl,
$C_1$–$C_{18}$-alkoxy and —$(OC_2H_4)_{1-3}$—O—$C_1$–$C_6$-alkyl,
$C_1$–$C_{15}$-alkylthio,
$C_1$–$C_8$-alkylthio which is monosubstituted to hexasubstituted in an identical or different manner by F and/or Cl,
tri-$C_1$–$C_6$-alkylsilyl,
phenyl-di-$C_1$–$C_6$-alkylsilyl,
3,4-difluoromethylenedioxo,
3,4-tetrafluoroethylenedioxo,
a fused-on benzo group,
a fused-on $C_4$-alkanediyl group,
the groupings

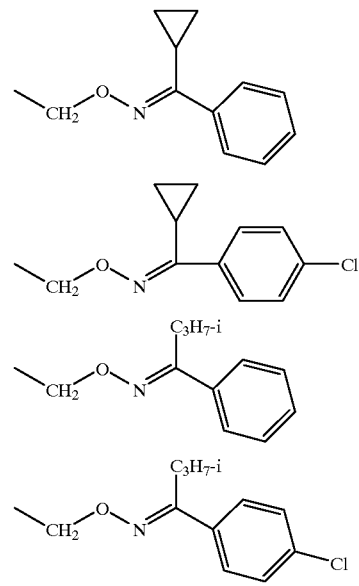

cyclohexyl or cyclohexyloxy, in each case optionally substituted by $C_1$–$C_4$-alkyl, $C_1$–$C_4$-alkoxy, cyclohexyl or phenyl;

pyridyloxy, which is optionally monosubstituted or disubstituted in an identical or different manner by F, Cl or $CF_3$;

phenyl, phenyl-$C_1$–$C_6$-alkyl, phenoxy, phenylthio, phenyl-$C_1$–$C_6$-alkoxy or benzylthio, in each case optionally monosubstituted to pentasubstituted in an identical or different manner by $C_1$–$C_{12}$-alkyl, F, Cl, Br, $C_1$–$C_4$-alkyl which is monosubstituted to hexasubstituted by F and/or Cl, $C_1$–$C_{12}$-alkoxy, $C_1$–$C_4$-alkoxy which is monosubstituted to hexasubstituted in an identical or different manner by F and/or Cl, $C_1$–$C_4$-alkoxy-$C_1$–$C_4$-alkyl, $C_1$–$C_4$-alkoxyethyleneoxy, $C_1$–$C_4$-alkylthio, or $C_1$–$C_4$-alkylthio which is monosubstituted to hexasubstituted in an identical or different manner by F and/or Cl.

D particularly preferably represents hydrogen or methyl.

E particularly preferably represents hydrogen, methyl or phenyl, phenyl-$C_1$–$C_4$-alkyl, phenoxy-$C_1$–$C_4$-alkyl, phenylthio-$C_1$–$C_4$-alkyl, phenylsulfinyl-$C_1$–$C_4$-alkyl or phenylsulfonyl-$C_1$–$C_4$-alkyl, in each case optionally monosubstituted to tetrasubstituted in an identical or different manner, possible substituents being the phenyl substituents mentioned above in the particularly preferred definition of substituent B.

G particularly preferably represents hydrogen or methyl.

J particularly preferably represents hydrogen or methyl.

K particularly preferably represents hydrogen or methyl, or represents phenyl, which can be monosubstituted to tetrasubstituted in an identical or different manner by the substituents mentioned for phenyl in connection with the particularly preferred definition of B, or B and D together also particularly preferably represent 2- to 6-membered alkanediyl, which is optionally monosubstituted to tetrasubstituted in an identical or different manner, wherein one or two $CH_2$ groups are optionally replaced by O and/or S, possible substituents being: $C_1$–$C_4$-alkyl, and phenyl or a fused-on benzo group, in each case optionally monosubstituted to tetrasubstituted in an identical or different manner, possible substituents in each case being the substituents mentioned for phenyl in connection with the particularly preferred definition of substituent B; or D and G together also particularly preferably represent 2- to 6-membered alkanediyl, which is optionally monosubstituted to tetrasubstituted in an identical or different manner, wherein one or two $CH_2$ groups are optionally replaced by O and/or S, possible substituents being: $C_1$–$C_4$-alkyl, and phenyl or a fused-on benzo group, in each case optionally monosubstituted to tetra substituted in an identical or different manner, possible substituents in each case being the substituents mentioned for phenyl in connection with the particularly preferred definition of substituent B, or E and G together also particularly preferably represent 2- to 6-membered alkanediyl, which is optionally monosubstituted to tetrasubstituted in an identical or different manner, wherein one or two $CH_2$ groups are optionally replaced by O and/or S, possible substituents being: $C_1$–$C_4$-alkyl, and phenyl or a fused-on benzo group, in each case optionally monosubstituted to tetrasubstituted in an identical or different manner, possible substituents in each case being the substituents mentioned for phenyl in connection with the particularly preferred definition of substituent B.

W and Y are different and also particularly preferably represent N, O or S, the ring always containing an N atom.

A especially preferably represents phenyl, which is monosubstituted to pentasubstituted in an identical or different manner by F, Cl, Br, $C_1$–$C_3$-alkyl, $C_1$–$C_3$-alkoxy, $C_1$–$C_3$-alkylthio, $C_1$–$C_2$-alkyl which is monosubstituted to pentasubstituted in an identical or different manner by F and/or Cl, $C_1$–$C_4$-alkoxy which is monosubstituted to pentasubstituted in an identical or different manner by F and/or Cl, $SCF_3$, $SCHF_2$, nitro or cyano;

B especially preferably represents hydrogen; or represents $C_1$–$C_4$-alkyl; or represents phenyl, benzyl, pheneth-1-yl, pheneth-2-yl, phenoxymethyl, phenylthiomethyl, phenylsulfinylmethyl, phenylsulfonylmethyl, phenylthioeth-1-yl, phenylsulfinyleth-1-yl, phenylsulfonyleth-1-yl, phenoxyeth-1-yl, phenoxyeth-2-yl, or styryl, in each case optionally monosubstituted to pentasubstituted in an identical or different manner, phenyl substituents which may be mentioned in each case being F, Cl, Br,
$C_1$–$C_{18}$-alkyl,
$C_1$–$C_6$-alkoxy-$C_1$–$C_8$-alkyl,
$C_1$–$C_8$-alkoxy which is monosubstituted to hexasubstituted in an identical or different manner by F and/or Cl,
$C_1$–$C_2$-alkyl which is monosubstituted to pentasubstituted in an identical or different manner by F and/or Cl,
$C_1$–$C_{18}$-alkoxy and —$(OC_2H_4)_{1-3}$—O—$C_1$–$C_6$-alkyl,
$C_1$–$C_{15}$-alkylthio,
$C_1$–$C_8$-alkylthio which is monosubstituted to hexasubstituted in an identical or different manner by F and/or Cl,
tri-$C_1$–$C_6$-alkylsilyl,
phenyl-di-$C_1$–$C_6$-alkylsilyl,
3,4-difluoromethylenedioxo,
3,4-tetrafluoroethylenedioxo,
a fused-on benzo group,
a fused-on $C_4$-alkanediyl group,
the groupings

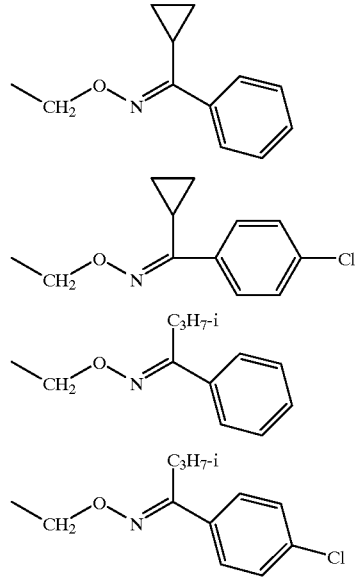

cyclohexyl or cyclohexyloxy, in each case optionally substituted by $C_1$–$C_4$-alkyl, $C_1$–$C_4$-alkoxy, cyclohexyl or phenyl;

pyridyloxy, which is optionally monosubstituted or disubstituted in an identical or different manner by F, Cl or $CF_3$;

phenyl, phenyl-$C_1$–$C_6$-alkyl, phenoxy, phenylthio, phenyl-$C_1$–$C_6$-alkoxy or benzylthio, in each case optionally monosubstituted to pentasubstituted in an identical or different manner by $C_1$–$C_{12}$-alkyl, F, Cl, Br, $C_1$–$C_4$-alkyl which is monosubstituted to hexasubstituted by F and/or Cl, $C_1$–$C_{12}$-alkoxy, $C_1$–$C_4$-alkoxy which is monosubstituted to hexasubstituted in an identical or different manner by F and/or Cl, $C_1$–$C_4$-alkoxy-$C_1$–$C_4$-alkyl, $C_1$–$C_4$-alkoxyethyleneoxy, $C_1$–$C_4$-alkylthio or $C_1$–$C_4$-alkylthio which is monosubstituted to hexasubstituted in an identical or different manner by F and/or Cl.

D especially preferably represents hydrogen or methyl.

E especially preferably represents hydrogen, methyl or phenyl, phenyl-$C_1$–$C_4$-alkyl, phenoxy-$C_1$–$C_4$-alkyl, phenylthio-$C_1$–$C_4$-alkyl, phenylsulfinyl-$C_1$–$C_4$-alkyl or phenylsulfonyl-$C_1$–$C_4$-alkyl, in each case optionally monosubstituted to tetrasubstituted in an identical or different manner, possible substituents being the phenyl substituents mentioned above in the especially preferred definition of substituent B.

G especially preferably represents hydrogen or methyl.

J especially preferably represents hydrogen or methyl.

K especially preferably represents hydrogen or methyl, or represents phenyl, which can be monosubstituted to tetrasubstituted in an identical or different manner by the substituents mentioned for phenyl in connection with the especially preferred definition of B, or B and D together especially preferably represent 2- to 6-membered alkanediyl which is optionally monosubstituted to tetrasubstituted in an identical or different manner, wherein one or two $CH_2$ groups are optionally replaced by O and/or S, possible substituents being: $C_1$–$C_4$-alkyl, and phenyl or a fused-on benzo group, in each case optionally monosubstituted to tetrasubstituted in an identical or different manner, possible substituents in each case being the substituents mentioned for phenyl in connection with the especially preferred definition of substituent B; or D and G together especially preferably represent 2- to 6-membered alkanediyl which is optionally monosubstituted to tetrasubstituted in an identical or different manner, wherein one or two $CH_2$ groups are optionally replaced by O and/or S, possible substituents being: $C_1$–$C_4$-alkyl, and phenyl or a fused-on benzo group, in each case optionally monosubstituted to tetrasubstituted in an identical or different manner, possible substituents in each case being the substituents mentioned for phenyl in connection with the especially preferred definition of substituent B; or E and G together especially preferably represent 2- to 6-membered alkanediyl which is optionally monosubstituted to tetrasubstituted in an identical or different manner, wherein one or two $CH_2$ groups are optionally replaced by O and/or S, possible substituents being: $C_1$–$C_4$-alkyl, and phenyl or a fused-on benzo group, in each case optionally monosubstituted to tetrasubstituted in an identical or different manner, possible substituents in each case being the substituents mentioned for phenyl in connection with the especially preferred definition of substituent B.

W and Y are different and especially preferably represent N, O or S, the ring always containing an N atom.

Some of the compounds of the formula (I) are known (compare, for example, Gazz. Chim. Ital. 104, 1181 (1974), FR 2 158 143, DE 2 158 615, IT 927 515, J. Org. Chem. 37, 2353 (1972), FR 1 585 475, J. Indian. Chem. Soc. 55, 195 (1978)).

The radical definitions and explanations given above generally or mentioned in preferred ranges can be combined with one another as desired, that is to say also between the particular ranges and preferred ranges.

The compounds of the formula (I) in which a combination of the meanings given above as preferred (preferably) is present are preferably used according to the invention.

The compounds of the formula (I) in which a combination of the meanings given above as particularly preferred is present are particularly preferably used according to the invention.

The compounds of the formula (I) in which a combination of these meanings given above as especially preferred is present are especially preferably used according to the invention.

Novel azine derivatives which can be used according to the invention are those of the formula (Ia)

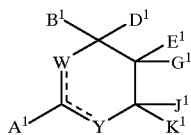

(Ia)

in which $A^1$ represents substituted phenyl, or represents in each case optionally substituted naphthyl, pyridyl, thienyl or pyrazolyl;

$B^1$ represents hydrogen, alkyl or in each case substituted phenyl, phenylalkyl, phenylalkenyl, phenoxyalkyl, phenylthioalkyl, phenylsulfinylalkyl or phenylsulfonylalkyl;

$D^1$ represents hydrogen or alkyl;

$E^1$ represents hydrogen, alkyl or in each case substituted phenyl, phenylalkyl, phenoxyalkyl, phenylthioalkyl, phenylsulfinylalkyl or phenylsulfonylalkyl;

$G^1$ represents hydrogen or alkyl;

$J^1$ represents hydrogen or alkyl;

$K^1$ represents hydrogen, alkyl or substituted phenyl; or $B^1$ and $D^1$ together represent optionally substituted alkanediyl, wherein one or two $CH_2$ groups are optionally replaced by O and/or S; or $D^1$ and $G^1$ together represent optionally substituted alkanediyl, wherein one or two $CH_2$ groups are optionally replaced by O and/or S; or $E^1$ and $G^1$ together represent optionally substituted alkanediyl, wherein one or two $CH_2$ groups are optionally replaced by O and/or S; and W and Y are different and represent N, O or S, wherein the ring always contains an N atom, with the proviso that at least one of the substituents $B^1$, $D^1$, $E^1$, $G^1$, $J^1$ and $K^1$ does not represent hydrogen or alkyl, and excluding the compounds of the formula

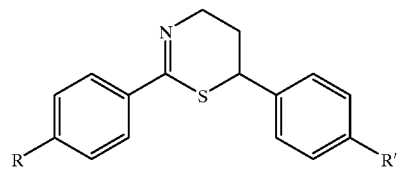

in which R and R' independently of one another represent chlorine, bromine, methyl or methoxy.

Depending on the nature of the substituents, the compounds of the formula (Ia) can be in the form of geometric and/or optical isomers or isomer mixtures of varying composition. The invention relates both to the pure isomers and to the isomer mixtures.

In formula (Ia), the broken line represents a double bond between the nitrogen atom and the adjacent carbon atom which carries the substituent $A^1$.

It has furthermore been found that the novel azine derivatives of the formula (Ia) are obtained by a) reacting aminoalcohols of the formula

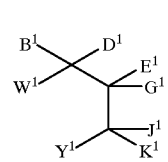

(II)

in which $B^1$, $D^1$, $E^1$, $G^1$, $J^1$ and $K^1$ have the abovementioned meanings;

$W^1$ represents amino and $Y^1$ represents hydroxyl; or $W^1$ represents hydroxyl and $Y^1$ represents amino; with a carboxylic acid of the formula $A^1$-COOH (III)

in which $A^1$ has the abovementioned meaning, with a dehydrating agent, if appropriate in the presence of a diluent; or b) reacting amide-alcohols of the formula

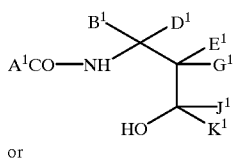
(IVa)

or

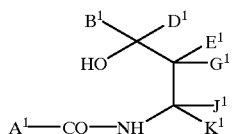
(IVb)

in which
$A^1$, $B^1$, $D^1$, $E^1$, $G^1$, $J^1$ and $K^1$ have the abovementioned meanings, with a dehydrating agent, if appropriate in the presence of a diluent; or c) reacting amide derivatives of the formula

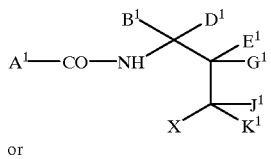
(Va)

or

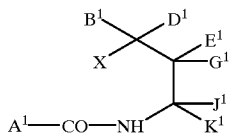
(Vb)

in which
$A^1$, $B^1$, $D^1$, $E^1$, $G^1$, $J^1$ and $K^1$ have the abovementioned meanings; and
X represents halogen, alkylsulfonyloxy or arylsulfonyloxy, with a base, if appropriate in the presence of a diluent; or d) reacting amide-alcohols of the formula

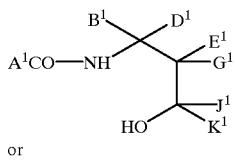
(IVa)

or

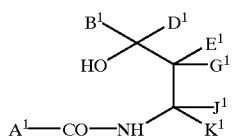
(IVb)

in which
$A^1$, $B^1$, $D^1$, $E^1$, $G^1$, $J^1$ and $K^1$ have the abovementioned meanings, with thienylating agents, if appropriate in the presence of a diluent.

Formula (Ia) provides a general definition of the novel compounds according to the invention.

$A^1$ preferably (preferentially) represents phenyl, which is monosubstituted to pentasubstituted in an identical or different manner by halogen, $C_1$–$C_6$-alkyl, $C_1$–$C_6$-alkoxy, $C_1$–$C_6$-alkylthio, $C_1$–$C_6$-halogenoalkyl, $C_1$–$C_6$-halogenoalkoxy, $C_1$–$C_6$-halogenoalkylthio, nitro or cyano;

or represents naphthyl, which is optionally monosubstituted to trisubstituted in an identical or different manner, substituents which may be mentioned being halogen, $C_1$–$C_6$-alkyl, $C_1$–$C_6$-alkoxy or $C_1$–$C_6$-halogenoalkoxy;

or represents pyridyl, which is optionally monosubstituted to trisubstituted in an identical or different manner, substituents which may be mentioned being halogen, $C_1$–$C_6$-alkyl, $C_1$–$C_6$-alkoxy, $C_1$–$C_6$-halogenoalkyl, $C_1$–$C_6$-halogenoalkoxy or cyano;

or represents thienyl, which is optionally monosubstituted to trisubstituted in an identical or different manner, substituents which may be mentioned being halogen or $C_1$–$C_6$-alkyl;

or represents pyrazolyl, which is optionally monosubstituted to trisubstituted in an identical or different manner, substituents which may be mentioned being halogen or $C_1$–$C_3$-alkyl.

$B^1$ preferably represents hydrogen; or represents $C_1$–$C_6$-alkyl; or represents phenyl, benzyl, pheneth-1-yl, pheneth-2-yl, phenoxymethyl, phenylthiomethyl, phenylsulfinylmethyl, phenylsulfonylmethyl, phenylthioeth-1-yl, phenylsulfinyleth-1-yl, phenylsulfonyleth-1-yl, phenoxyeth-1-yl, phenoxyeth-2-yl or styryl, in each case monosubstituted to pentasubstituted in an identical or different manner, phenyl substituents which may be mentioned in each case being
halogen,
$C_1$–$C_{18}$-alkyl,
$C_1$–$C_8$-alkoxy-$C_1$–$C_8$-alkyl,
$C_1$–$C_8$-halogenoalkoxy,
$C_1$–$C_4$-halogenoalkyl,
$C_1$–$C_{18}$-alkoxy, which is optionally interrupted by a further 1 to 3 oxygen atoms,
$C_1$–$C_{18}$-alkylthio,
$C_1$–$C_8$-halogenoalkylthio,
tri-$C_1$–$C_8$-alkylsilyl,
phenyl-di-$C_1$–$C_8$-alkylsilyl,
3,4-difluoromethylenedioxo,
3,4-tetrafluoroethylenedioxo,
a fused-on benzo group,
a fused-on $C_3$–$C_4$-alkanediyl group,
benzyliminooxymethyl, which is optionally substituted by $C_1$–$C_4$-alkyl or $C_3$–$C_6$-cycloalkyl and/or halogen,
cyclohexyl or cyclohexyloxy, in each case optionally substituted by $C_1$–$C_6$-alkyl, $C_1$–$C_6$-alkoxy, cyclohexyl or phenyl;
pyridyloxy, which is optionally monosubstituted or disubstituted in an identical or different manner by halogen, $C_1$–$C_4$-alkyl or $C_1$–$C_4$-halogenoalkyl;
phenyl, phenyl-$C_1$–$C_6$-alkyl, phenoxy, phenylthio, phenyl-$C_1$–$C_6$-alkoxy or benzylthio,
in each case optionally monosubstituted to pentasubstituted in an identical or different manner by $C_1$–$C_{12}$-alkyl, halogen, $C_1$–$C_4$-halogenoalkyl, $C_1$–$C_{12}$-alkoxy, $C_1$–$C_6$-halogenoalkoxy, $C_1$–$C_6$-alkoxy-$C_1$–$C_6$-alkyl, $C_1$–$C_6$-alkoxy-ethyleneoxy, $C_1$–$C_6$-alkylthio and/or $C_1$–$C_6$-halogenoalkylthio.

$D^1$ preferably represents hydrogen or methyl.

$E^1$ preferably represents hydrogen, methyl or phenyl, phenyl-$C_1$–$C_6$-alkyl, phenoxy-$C_1$–$C_6$-alkyl, phenylthio-$C_1$–$C_6$-alkyl, phenylsulfinyl-$C_1$–$C_6$-alkyl or phenylsulfonyl-$C_1$–$C_6$-alkyl, in each case monosubstituted to tetrasubstituted in an identical or different manner, possible substituents being the phenyl substituents mentioned above in the preferred definition of substituent $B^1$.

$G^1$ preferably represents hydrogen or methyl.

$J^1$ preferably represents hydrogen or methyl.

$K^1$ preferably represents hydrogen or methyl, or represents phenyl, which is monosubstituted to tetrasubstituted in an identical or different manner by the substituents mentioned for phenyl in connection with the preferred definition of $B^1$, or $B^1$ and $D^1$ together preferably represent 2- to 6-membered alkanediyl, which is optionally monosubstituted to tetrasubstituted in an identical or different manner, wherein one or two $CH_2$ groups are optionally replaced by O and/or S, possible substituents being: $C_1$–$C_4$-alkyl, and phenyl or a fused-on benzo group, in each case optionally monosubstituted to tetrasubstituted in an identical or different manner, possible substituents in each case being the substituents mentioned for phenyl in connection with the preferred definition of substituent $B^1$, or $D^1$ and $G^1$ together preferably represent 2- to 6-membered alkanediyl, which is optionally monosubstituted to tetrasubstituted in an identical or different manner, wherein one or two $CH_2$ groups are optionally replaced by O and/or S, possible substituents being: $C_1$–$C_4$-alkyl, and phenyl or a fused-on benzo group, in each case optionally monosubstituted to tetrasubstituted in an identical or different manner, possible substituents in each case being the substituents mentioned for phenyl in connection with the preferred definition of substituent $B^1$; or $E^1$ and $G^1$ together preferably represent 2- to 6-membered alkanediyl, which is optionally monosubstituted to tetrasubstituted in an identical or different manner, wherein one or two $CH_2$ groups are optionally replaced by O and/or S, possible substituents being: $C_1$–$C_4$-alkyl, and phenyl or a fused-on benzo group, in each case optionally monosubstituted to tetrasubstituted in an identical or different manner, possible substituents in each case being the substituents mentioned for phenyl in connection with the preferred definition of substituent $B^1$.

W and Y are different and also preferably represent N, O or S, the ring always containing an N atom.

$A^1$ particularly preferably represents phenyl, which is monosubstituted to pentasubstituted in an identical or different manner by F, Cl, Br, $C_1$–$C_3$-alkyl, $C_1$–$C_3$-alkoxy, $C_1$–$C_3$-alkylthio, $C_1$–$C_2$-alkyl which is monosubstituted to pentasubstituted in an identical or different manner by F and/or Cl, $C_1$–$C_4$-alkoxy which is monosubstituted to pentasubstituted in an identical or different manner by F and/or Cl, $SCF_3$, $SCHF_2$, nitro or cyano;

or represents naphthyl, which is optionally monosubstituted to trisubstituted in an identical or different manner, substituents which may be mentioned being F, Cl, $C_1$–$C_6$-alkyl, $C_1$–$C_6$-alkoxy or $C_1$–$C_6$-alkoxy which is monosubstituted to trisubstituted in an identical or different manner by F and/or Cl;

or represents pyridyl, which is optionally monosubstituted to disubstituted in an identical or different manner, substituents which may be mentioned being F, Cl, $C_1$–$C_3$-alkyl, $C_1$–$C_3$-alkoxy, $CF_3$, $OCF_3$ or cyano;

or represents thienyl, which is optionally monosubstituted to disubstituted in an identical or different manner, substituents which may be mentioned being Cl, Br, $CH_3$ or $C_2H_5$;

or represents pyrazolyl, which is optionally monosubstituted to trisubstituted in an identical or different manner, substituents which may be mentioned being F, Cl, Br or $C_1$–$C_3$-alkyl.

$B^1$ particularly preferably represents hydrogen; or represents $C_1$–$C_4$-alkyl; or represents phenyl, benzyl, pheneth-1-yl, pheneth-2-yl, phenoxymethyl, phenylthiomethyl, phenylsulfinylmethyl, phenylsulfonylmethyl, phenylthioeth-1-yl, phenylsulfinyleth-1-yl, phenylsulfonyleth-1-yl, phenoxyeth-1-yl, phenoxyeth-2-yl or styryl, in each case monosubstituted to pentasubstituted in an identical or different manner, phenyl substituents which may be mentioned in each case being F, Cl, Br,
$C_1$–$C_{18}$-alkyl,
$C_1$–$C_6$-alkoxy-$C_1$–$C_8$-alkyl,
$C_1$–$C_8$-alkoxy which is monosubstituted to hexasubstituted in an identical or different manner by F and/or Cl,
$C_1$–$C_2$-alkyl which is monosubstituted to pentasubstituted in an identical or different manner by F and/or Cl,
$C_1$–$C_{18}$-alkoxy and —$(OC_2H_4)_{1-3}$—O—$C_1$–$C_6$-alkyl,
$C_1$–$C_{15}$-alkylthio,
$C_1$–$C_8$-alkylthio which is monosubstituted to hexasubstituted in an identical or different manner by F and/or Cl,
tri-$C_1$–$C_6$-alkylsilyl,
phenyl-di-$C_1$–$C_6$-alkylsilyl,
3,4-difluoromethylenedioxo,
3,4-tetrafluoroethylenedioxo,
a fused-on benzo group,
a fused-on $C_4$-alkanediyl group,
the groupings

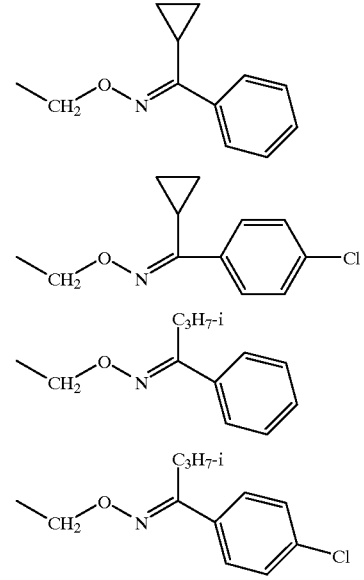

cyclohexyl or cyclohexyloxy, in each case optionally substituted by $C_1$–$C_4$-alkyl, $C_1$–$C_4$-alkoxy, cyclohexyl or phenyl;

pyridyloxy, which is optionally monosubstituted or disubstituted in an identical or different manner by F, Cl or $CF_3$;

phenyl, phenyl-$C_1$–$C_6$-alkyl, phenoxy, phenylthio, phenyl-$C_1$–$C_6$-alkoxy or benzylthio, in each case optionally monosubstituted to pentasubstituted in an identical or different manner by $C_1$–$C_{12}$-alkyl, F, Cl, Br, $C_1$–$C_4$-alkyl which is monosubstituted to hexasubstituted by F and/or Cl, $C_1$–$C_{12}$-alkoxy, $C_1$–$C_4$-alkoxy which is monosubstituted to hexasubstituted in an identical or different manner by F and/or Cl, $C_1$–$C_4$-alkoxy-$C_1$–$C_4$-alkyl, $C_1$–$C_4$-alkoxyethyleneoxy, $C_1$–$C_4$-alkylthio, or $C_1$–$C_4$-alkylthio which is monosubstituted to hexasubstituted in an identical or different manner by F and/or Cl.

$D^1$ particularly preferably represents hydrogen or methyl.

$E^1$ particularly preferably represents hydrogen, methyl or phenyl, phenyl-$C_1$–$C_4$-alkyl, phenoxy-$C_1$–$C_4$-alkyl, phenylthio-$C_1$–$C_4$-alkyl, phenylsulfinyl-$C_1$–$C_4$-alkyl or phenylsulfonyl-$C_1$–$C_4$-alkyl, in each case monosubstituted to tetrasubstituted in an identical or different manner, possible substituents being the phenyl substituents mentioned above in the particularly preferred definition of substituent $B^1$.

$G^1$ particularly preferably represents hydrogen or methyl.

$J^1$ particularly preferably represents hydrogen or methyl.

$K^1$ particularly preferably represents hydrogen or methyl, or represents phenyl, which is monosubstituted to tetrasubstituted in an identical or different manner by the substituents mentioned for phenyl in connection with the particularly preferred definition of $B^1$, or $B^1$ and $D^1$ together particularly preferably represent 2- to 6-membered alkanediyl, which is optionally monosubstituted to tetrasubstituted in an identical or different manner, wherein one or two $CH_2$ groups are optionally replaced by O and/or S, possible substituents being: $C_1$–$C_4$-alkyl, and phenyl or a fused-on benzo group, in each case optionally monosubstituted to tetrasubstituted in an identical or different manner, possible substituents in each case being the substituents mentioned for phenyl in connection with the particularly preferred definition of substituent $B^1$; or $D^1$ and $G^1$ together also particularly preferably represent 2- to 6-membered alkanediyl, which is optionally monosubstituted to tetrasubstituted in an identical or different manner, wherein one or two $CH_2$ groups are optionally replaced by O and/or S, possible substituents being: $C_1$–$C_4$-alkyl, and phenyl or a fused-on benzo group, in each case optionally monosubstituted to tetra substituted in an identical or different manner, possible substituents in each case being the substituents mentioned for phenyl in connection with the particularly preferred definition of substituent $B^1$; or $E^1$ and $G^1$ together also particularly preferably represent 2- to 6-membered alkanediyl, which is optionally monosubstituted to tetrasubstituted in an identical or different manner, wherein one or two $CH_2$ groups are optionally replaced by O and/or S, possible substituents being: $C_1$–$C_4$-alkyl, and phenyl or a fused-on benzo group, in each case optionally monosubstituted to tetrasubstituted in an identical or different manner, possible substituents in each case being the substituents mentioned for phenyl in connection with the particularly preferred definition of substituent $B^1$.

W and Y are different and also particularly preferably represent N, O or S, the ring always containing an N atom.

$A^1$ especially preferably represents phenyl, which is monosubstituted to pentasubstituted in an identical or different manner by F, Cl, Br, $C_1$–$C_3$-alkyl, $C_1$–$C_3$-alkoxy, $C_1$–$C_3$-alkylthio, $C_1$–$C_2$-alkyl which is monosubstituted to pentasubstituted in an identical or different manner by F and/or Cl, $C_1$–$C_4$-alkoxy which is monosubstituted to pentasubstituted in an identical or different manner by F and/or Cl, $SCF_3$, $SCHF_2$, nitro or cyano;

$B^1$ especially preferably represents hydrogen; or represents $C_1$–$C_4$-alkyl; or represents phenyl, benzyl, pheneth-1-yl, pheneth-2-yl, phenoxymethyl, phenylthiomethyl, phenylsulfinylmethyl, phenylsulfonylmethyl, phenylthioeth-1-yl, phenylsulfinyleth-1-yl, phenylsulfonyleth-1-yl, phenoxyeth-1-yl, phenoxyeth-2-yl or styryl, in each case monosubstituted to pentasubstituted in an identical or different manner, phenyl substituents which may be mentioned in each case being F, Cl, Br, $C_1$–$C_{18}$-alkyl, $C_1$–$C_6$-alkoxy-$C_1$–$C_8$-alkyl, $C_1$–$C_8$-alkoxy which is monosubstituted to hexasubstituted in an identical or different manner by F and/or Cl, $C_1$–$C_2$-alkyl which is monosubstituted to pentasubstituted in an identical or different manner by F and/or Cl, $C_1$–$C_{18}$-alkoxy and —$(OC_2H_4)_{1-3}$—O—$C_1$–$C_6$-alkyl, $C_1$–$C_{15}$-alkylthio, $C_1$–$C_8$-alkylthio which is monosubstituted to hexasubstituted in an identical or different manner by F and/or Cl, tri-$C_1$–$C_6$-alkylsilyl, phenyl-di-$C_1$–$C_6$-alkylsilyl, 3,4-difluoromethylenedioxo, 3,4-tetrafluoroethylenedioxo, a fused-on benzo group, a fused-on $C_4$-alkanediyl group, the groupings

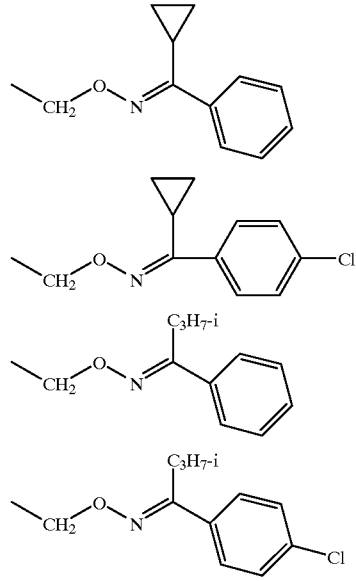

cyclohexyl or cyclohexyloxy, in each case optionally substituted by $C_1$–$C_4$-alkyl, $C_1$–$C_4$-alkoxy, cyclohexyl or phenyl;

pyridyloxy, which is optionally monosubstituted or disubstituted in an identical or different manner by F, Cl or $CF_3$;

phenyl, phenyl-$C_1$–$C_6$-alkyl, phenoxy, phenylthio, phenyl-$C_1$–$C_6$-alkoxy or benzylthio, in each case optionally monosubstituted to pentasubstituted in an identical or different manner by $C_1$–$C_{12}$-alkyl, F. Cl, Br, $C_1$–$C_4$-alkyl which is monosubstituted to hexasubstituted by F and/or Cl, $C_1$–$C_{12}$-alkoxy, $C_1$–$C_4$-alkoxy which is monosubstituted to hexasubstituted in an identical or different manner by F and/or Cl, $C_1$–$C_4$-alkoxy-$C_1$–$C_4$-alkyl, $C_1$–$C_4$-alkoxyethyleneoxy, $C_1$–$C_4$-alkylthio or $C_1$–$C_4$-alkylthio which is monosubstituted to hexasubstituted in an identical or different manner by F and/or Cl.

$D^1$ especially preferably represents hydrogen or methyl.

$E^1$ especially preferably represents hydrogen or methyl, or phenyl, phenyl-$C_1$–$C_4$-alkyl, phenoxy-$C_1$–$C_4$-alkyl, phenylthio-$C_1$–$C_4$-alkyl, phenylsulfinyl-$C_1$–$C_4$-alkyl or phenylsulfonyl-$C_1$–$C_4$-alkyl, in each case monosubstituted to tetrasubstituted in an identical or different manner, possible substituents being the phenyl substituents mentioned above in the especially preferred definition of substituent $B^1$.

$G^1$ especially preferably represents hydrogen or methyl.

$J^1$ especially preferably represents hydrogen or methyl.

$K^1$ especially preferably represents hydrogen or methyl, or represents phenyl, which is monosubstituted to tetrasubstituted in an identical or different manner by the substituents mentioned for phenyl in connection with the especially preferred definition of $B^1$, or $B^1$ and $D^1$ together especially preferably represent 2- to 6-membered alkanediyl which is optionally monosubstituted to tetrasubstituted in an identical or different manner, wherein one or two $CH_2$ groups are optionally replaced by O and/or S, possible substituents being: $C_1$–$C_4$-alkyl, and phenyl or a fused-on benzo group, in each case optionally monosubstituted to tetrasubstituted in an identical or different manner, possible substituents in each case being the substituents mentioned for phenyl in connection with the especially preferred definition of substituent $B^1$, $D^1$ and $G^1$ together especially preferably represent 2- to 6-membered alkanediyl which is optionally monosubstituted to tetrasubstituted in an identical or different manner, wherein one or two $CH_2$ groups are optionally replaced by O and/or S, possible substituents being: $C_1$–$C_4$-alkyl, and phenyl or a fused-on benzo group, in each case optionally monosubstituted to tetrasubstituted in an identical or different manner, possible substituents in each case being the substituents mentioned for phenyl in connection with the especially preferred definition of substituent $B^1$; or $E^1$ and $G^1$ together especially preferably represent 2- to 6-membered alkanediyl which is optionally monosubstituted to tetrasubstituted in an identical or different manner, wherein one or two $CH_2$ groups are optionally replaced by O and/or S, possible substituents being: $C_1$–$C_4$-alkyl, and phenyl or a fused-on benzo group, in each case optionally monosubstituted to tetrasubstituted in an identical or different manner, possible substituents in each case being the substituents mentioned for phenyl in connection with the especially preferred definition of substituent B.

W and Y are different and especially preferably represent N, O or S, the ring always containing an N atom.

In each case, at least one of the substituents $B^1$, $D^1$, $E^1$, $G^1$, $J^1$ and $K^1$ does not represent hydrogen or alkyl, and the compounds of the formula

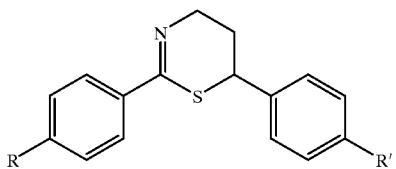

in which R and R' independently of one another represent chlorine, bromine, methyl or methoxy, are excluded.

The radical definitions and explanations given above generally or mentioned in preferred ranges can be combined with one another as desired, that is to say also between the particular ranges and preferred ranges. They apply accordingly to the end products and to the precursors and intermediates.

Compounds of the general formula (Ia) which are preferred according to the invention are those in which a combination of the meanings given above as preferred (preferably) is present.

Compounds of the general formula (Ia) which are particularly preferred according to the invention are those in which a combination of the meanings given above as particularly preferred is present.

Compounds of the general formula (Ia) which are especially preferred according to the invention are those in which a combination of these meanings given above as especially preferred is present.

Preferred compounds according to the invention are substances of the formula (Ia-1)

(Ia-1)

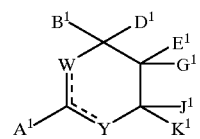

in which $A^1$, $B^1$, ($B^1$ and $D^1$), W and Y have the meanings given in the definition of the invention and $D^1$, $E^1$, $G^1$, $J^1$ and $K^1$ are identical or different and represent hydrogen or methyl.

Preferred novel compounds according to the invention are also substance groups of the formulae (Ia-2) to (Ia-17):

(Ia-2)

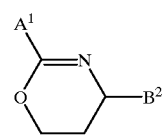

in which $A^1$ represents the abovementioned general, preferred and particularly preferred meanings and $B^2$ represents phenyl which is monosubstituted to pentasubstituted in an identical or different manner, possible substituents being the phenyl substituents mentioned above as preferred and particularly preferred under $B^1$.

(Ia-3)

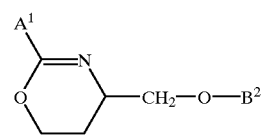

in which $A^1$ represents the abovementioned general, preferred and particularly preferred meanings and $B^2$ represents phenyl which is monosubstituted to tetrasubstituted in an identical or different manner, possible substituents being the phenyl substituents mentioned above as preferred and particularly preferred under $B^1$.

(Ia-4)

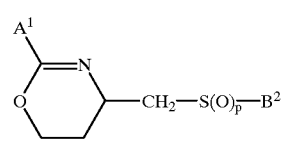

in which $A^1$ represents the abovementioned general, preferred and particularly preferred meanings and p represents 0, 1 or 2 and $B^2$ represents phenyl which is monosubstituted to tetrasubstituted in an identical or different manner, possible substituents being the phenyl substituents mentioned above as preferred and particularly preferred under $B^1$.

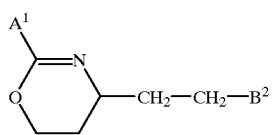 (Ia-5)

in which

A$^1$ represents the abovementioned general, preferred and particularly preferred meanings and B$^2$ represents phenyl which is monosubstituted to tetrasubstituted in an identical or different manner, possible substituents being the phenyl substituents mentioned above as preferred and particularly preferred under B$^1$.

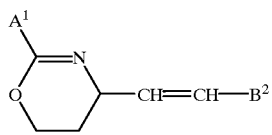 (Ia-6)

in which

A$^1$ represents the abovementioned general, preferred and particularly preferred meanings and B$^2$ represents phenyl which is monosubstituted to tetrasubstituted in an identical or different manner, possible substituents being the phenyl substituents mentioned above as preferred and particularly preferred under B$^1$.

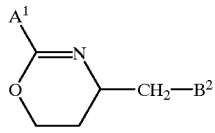 (Ia-7)

in which

A$^1$ represents the abovementioned general, preferred and particularly preferred meanings and B$^2$ represents phenyl which is monosubstituted to tetrasubstituted in an identical or different manner, possible substituents being the phenyl substituents mentioned above as preferred and particularly preferred under B$^1$.

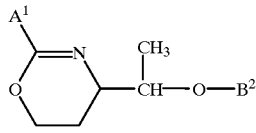 (Ia-8)

in which

A$^1$ represents the abovementioned general, preferred and particularly preferred meanings and B$^2$ represents phenyl which is monosubstituted to tetrasubstituted in an identical or different manner, possible substituents being the phenyl substituents mentioned above as preferred and particularly preferred under B$^1$.

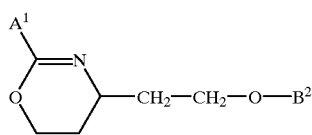 (Ia-9)

in which

A$^1$ represents the abovementioned general, preferred and particularly preferred meanings and B$^2$ represents phenyl which is monosubstituted to tetrasubstituted in an identical or different manner, possible substituents being the phenyl substituents mentioned above as preferred and particularly preferred under B$^1$.

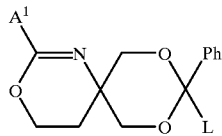 (Ia-10)

in which

A$^1$ represents the abovementioned general, preferred and particularly preferred meanings, L represents hydrogen or methyl and Ph represents phenyl which is optionally monosubstituted to tetrasubstituted in an identical or different manner, possible substituents being the phenyl substituents mentioned above as preferred and particularly preferred under B$^1$.

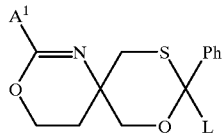 (Ia-11)

in which

A$^1$ represents the abovementioned general, preferred and particularly preferred meanings, L represents hydrogen or methyl and Ph represents phenyl which is optionally monosubstituted to tetrasubstituted in an identical or different manner, possible substituents being the phenyl substituents mentioned above as preferred and particularly preferred under B$^1$.

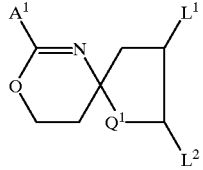 (Ia-12)

in which

A$^1$ represents the abovementioned general, preferred and particularly preferred meanings, Q$^1$ represents the groupings —CH$_2$CH$_2$—, —CH$_2$O— or —CH$_2$— and L$^1$ and L$^2$ represent hydrogen and phenyl, which is optionally monosubstituted to tetrasubstituted in an identical or different manner, possible substituents being the phenyl substituents mentioned above as preferred and particularly preferred under $B^1$, either $L^1$ or $L^2$ representing hydrogen; or $L^1$ and $L^2$ together represent a fused-on benzo group, which is optionally monosubstituted to tetrasubstituted in an identical or different manner, possible substituents being the phenyl substituents mentioned above as preferred and particularly preferred under $B^1$.

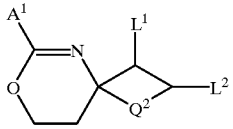

(Ia-13)

in which $A^1$ represents the abovementioned general, preferred and particularly preferred meanings and $Q^2$ represents the groupings —$CH_2CH_2$— or —$CH_2O$— and $L^1$ and $L^2$ together represent a fused-on benzo group, which is optionally monosubstituted to tetrasubstituted in an identical or different manner, possible substituents being the phenyl substituents mentioned above as preferred and particularly preferred under ($B^1$).

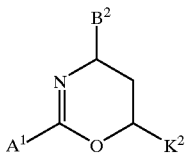

(Ia-14)

in which $A^1$ represents the abovementioned general, preferred and particularly preferred meanings and $B^2$ and $K^2$ are identical or different and represent phenyl which is monosubstituted to tetrasubstituted in an identical or different manner, possible substituents being the phenyl substituents mentioned above as preferred and particularly preferred under $B^1$.

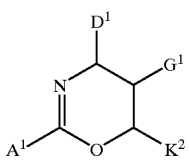

(Ia-15)

in which $A^1$, $D^1$ and $G^1$ represent the abovementioned general, preferred and particularly preferred meanings and $K^2$ represents phenyl which is monosubstituted to tetrasubstituted in an identical or different manner, possible substituents being the phenyl substituents mentioned above as preferred and particularly preferred under $B^1$.

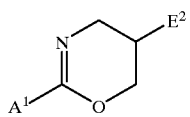

(Ia-16)

in which $A^1$ represents the abovementioned general, preferred and particularly preferred meanings and $E^2$ represents phenyl which is monosubstituted to tetrasubstituted in an identical or different manner, possible substituents being the phenyl substituents mentioned above as preferred and particularly preferred under $B^1$.

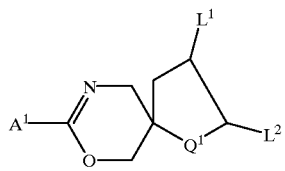

(Ia-17)

in which $A^1$ represents the abovementioned general, preferred and particularly preferred meanings, $Q^1$ represents the groupings —$CH_2CH_2$—, —$CH_2O$— or —$CH_2$— and $L^1$ and $L^2$ represent hydrogen and phenyl, which is optionally monosubstituted to tetrasubstituted in an identical or different manner, possible substituents being the phenyl substituents mentioned above as preferred and particularly preferred under $B^1$, either $L^1$ or $L^2$ representing hydrogen; or $L^1$ and $L^2$ together represent a fused-on benzo group, which is optionally monosubstituted to tetrasubstituted in an identical or different manner, possible substituents being the phenyl substituents mentioned above as preferred and particularly preferred under Other preferred compounds according to the invention are substance groups of the formulae (Ia-2) to (Ia-17) in which $A^1$ represents phenyl which is monosubstituted to pentasubstituted in an identical or different manner, possible substituents being the phenyl substituents mentioned above as preferred and particularly preferred under $A^1$.

Preferred compounds according to the invention are likewise substance groups of the formulae (Ia-18) to (Ia-29):

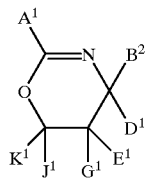

(Ia-18)

in which $A^1$ represents the abovementioned general, preferred and particularly preferred meanings and $B^2$ represents phenyl which is monosubstituted to tetrasubstituted in an identical or different manner, possible substituents being the phenyl substituents mentioned above as preferred and particularly preferred under $B^1$; and $D^1$, $E_1$, $G^1$, $J^1$ and $K^1$ are identical or different and represent hydrogen or methyl, but at least one substituent represents methyl.

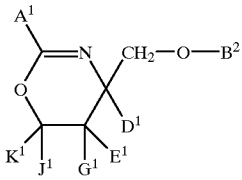
(Ia-19)

in which $A^1$ represents the abovementioned general, preferred and particularly preferred meanings and $B^2$ represents phenyl which is monosubstituted to tetra-substituted in an identical or different manner, possible substituents being the phenyl substituents mentioned above as preferred and particularly preferred under $B^1$; and $D^1$, $E^1$, $G^1$, $J^1$ and $K^1$ are identical or different and represent hydrogen or methyl, but at least one substituent represents methyl.

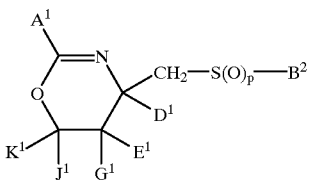
(Ia-20)

in which $A^1$ represents the abovementioned general, preferred and particularly preferred meanings, p represents 0, 1 or 2, $B^2$ represents phenyl which is monosubstituted to tetra-substituted in an identical or different manner, possible substituents being the phenyl substituents mentioned above as preferred and particularly preferred under $B^1$; and $D^1$, $E^1$, $G^1$, $J^1$ and $K^1$ are identical or different and represent hydrogen or methyl, but at least one substituent represents methyl.

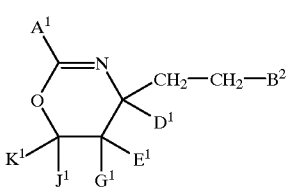
(Ia-21)

in which $A^1$ represents the abovementioned general, preferred and particularly preferred meanings and $B^2$ represents phenyl which is monosubstituted to tetra-substituted in an identical or different manner, possible substituents being the phenyl substituents mentioned above as preferred and particularly preferred under $B^1$; and $D^1$, $E^1$, $G^1$, $J^1$ and $K^1$ are identical or different and represent hydrogen or methyl, but at least one substituent represents methyl.

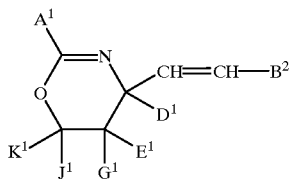
(Ia-22)

in which $A^1$ represents the abovementioned general, preferred and particularly preferred meanings and $B^2$ represents phenyl which is monosubstituted to tetra-substituted in an identical or different manner, possible substituents being the phenyl substituents mentioned above as preferred and particularly preferred under $B^1$; and $D^1$, $E^1$, $G^1$, $J^1$ and $K^1$ are identical or different and represent hydrogen or methyl, but at least one substituent represents methyl.

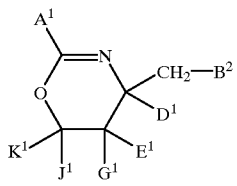
(Ia-23)

in which $A^1$ represents the abovementioned general, preferred and particularly preferred meanings and $B^2$ represents phenyl which is monosubstituted to tetra-substituted in an identical or different manner, possible substituents being the phenyl substituents mentioned above as preferred and particularly preferred under $B^1$; and $D^1$, $E^1$, $G^1$, $J^1$ and $K^1$ are identical or different and represent hydrogen or methyl, but at least one substituent represents methyl.

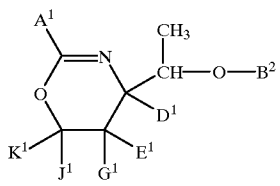
(Ia-24)

in which $A^1$ represents the abovementioned general, preferred and particularly preferred meanings and $B^2$ represents phenyl which is monosubstituted to tetra-substituted in an identical or different manner, possible substituents being the phenyl substituents mentioned above as preferred and particularly preferred under $B^1$; and $D^1$, $E^1$, $G^1$, $J^1$ and $K^1$ are identical or different and represent hydrogen or methyl, but at least one substituent represents methyl.

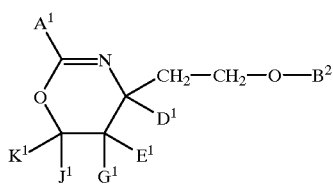
(Ia-25)

in which

A$^1$ represents the abovementioned general, preferred and particularly preferred meanings and B$^2$ represents phenyl which is monosubstituted to tetrasubstituted in an identical or different manner, possible substituents being the phenyl substituents mentioned above as preferred and particularly preferred under B$^1$; and D$^1$, E$^1$, G$^1$, J$^1$ and K$^1$ are identical or different and represent hydrogen or methyl, but at least one substituent represents methyl.

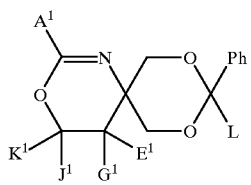
(Ia-26)

in which

A$^1$ represents the abovementioned general, preferred and particularly preferred meanings, L represents hydrogen or methyl and Ph represents phenyl which is optionally monosubstituted to tetrasubstituted in an identical or different manner, possible substituents being the phenyl substituents mentioned above as preferred and particularly preferred under B$^1$; and E$^1$, G$^1$, J$^1$ and K$^1$ are identical or different and represent hydrogen or methyl, but at least one substituent represents methyl.

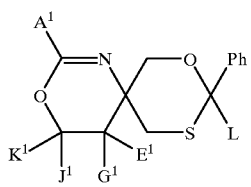
(Ia-27)

in which

A$^1$ represents the abovementioned general, preferred and particularly preferred meanings, L represents hydrogen or methyl and Ph represents phenyl which is optionally monosubstituted to tetrasubstituted in an identical or different manner, possible substituents being the phenyl substituents mentioned above as preferred and particularly preferred under B$^1$; and E$^1$, G$^1$, J$^1$ and K$^1$ are identical or different and represent hydrogen or methyl, but at least one substituent represents methyl.

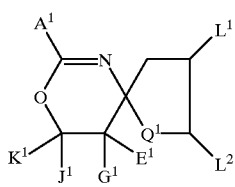
(Ia-28)

in which

A$^1$ represents the abovementioned general, preferred and particularly preferred meanings, Q$^1$ represents the groupings —CH$_2$CH$_2$—, —CH$_2$O— or —CH$_2$— and L$^1$ and L$^2$ represent hydrogen and phenyl, which is optionally monosubstituted to tetrasubstituted in an identical or different manner, possible substituents being the phenyl substituents mentioned above as preferred and particularly preferred under B$^1$, either L$^1$ or L$^2$ representing hydrogen; or L$^1$ and L$^2$ together represent a fused-on benzo group, which is optionally monosubstituted to tetrasubstituted in an identical or different manner, possible substituents being the phenyl substituents mentioned above as preferred and particularly preferred under B$^1$; and E$^1$, G$^1$, J$^1$ and K$^1$ are identical or different and represent hydrogen or methyl, but at least one substituent represents methyl.

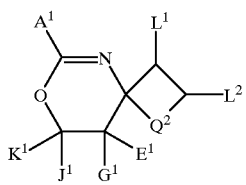
(Ia-29)

in which

A$^1$ represents the abovementioned general, preferred and particularly preferred meanings and Q$^2$ represents the groupings —CH$_2$CH$_2$— or —CH$_2$O— and L$^1$ and L$^2$ together represent a fused-on benzo group, which is optionally monosubstituted to tetrasubstituted in an identical or different manner, possible substituents being the phenyl substituents mentioned above as preferred and particularly preferred under (B$^1$); and E$^1$, G$^1$, J$^1$ and K$^1$ are identical or different and represent hydrogen or methyl, but at least one substituent represents methyl.

Further preferred compounds according to the invention are substance groups of the formulae (Ia-18) to (Ia-29) in which A$^1$ represents phenyl which is monosubstituted to pentasubstituted in an identical or different manner, possible substituents being the phenyl substituents mentioned above as preferred and particularly preferred under A$^1$.

Further preferred compounds according to the invention are described by the formula (Ia-30)

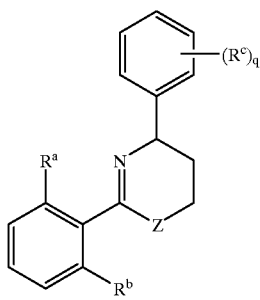

(Ia-30)

in which
R$^a$ represents hydrogen, fluorine or chlorine,
R$^b$ represents fluorine or chlorine,
q represents a number from 0 to 5,
R$^c$ represents $C_1$–$C_{15}$-alkyl, $C_1$–$C_{15}$-alkoxy, $C_1$–$C_{10}$-alkylthio, halogen, lower halogenoalkyl, lower halogenoalkoxy or tri(lower alkyl)silyl, or represents $C_3$–$C_7$-cycloalkyl, which is optionally monosubstituted to trisubstituted by lower alkyl, or represents

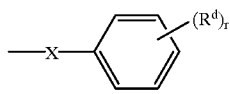

in which
X represents a direct bond, oxygen, lower alkanediyl, lower alkanediyloxy or di(lower alkyl)silyl,
r represents a number from 0 to 5,
R$^d$ represents $C_1$–$C_{12}$-alkyl, $C_1$–$C_{12}$-alkoxy, halogen, lower halogenoalkyl, lower halogenoalkoxy or tri(lower alkyl)silyl and
Z represents oxygen or sulfur.

Further preferred compounds according to the invention are described by the formula (Ia-30), in which R$^a$, R$^b$, R$^c$ and q have the abovementioned meaning and Z represents oxygen.

For q>1, the radicals R$^c$ can be identical or different.
For r>1, the radicals R$^d$ can be identical or different.

The hydrocarbon radicals, such as alkyl, mentioned above in the definition of the compounds according to the invention are—also in combination with hetero atoms, such as alkoxy—in each case straight-chain or branched, where possible.

In the definition of the compounds of the formula (Ia-30), the term "lower" means that the number of carbon atoms in the group in question is one to six, preferably one to four.

In the definition of the compounds of the formula (Ia-30), the term "alkyl", by itself or in combination with other groups, denotes a straight-chain or branched, saturated aliphatic hydrocarbon radical. Examples which may be mentioned are methyl, ethyl, n-propyl, isopropyl, n-butyl, isobutyl, sec-butyl, tert-butyl, n-pentyl, isoamyl, neopentyl, n-hexyl, n-heptyl, 1,1-dimethylpentyl, n-octyl, 1-methylheptyl, 1,1-dimethyl-4-methylpentyl, n-nonyl, 1,1-dimethylheptyl, n-decyl, n-undecyl, 4,8-dimethylnonyl, n-dodecyl, n-tridecyl, n-tetradecyl and n-pentadecyl.

Examples of halogenoalkyl groups which may be mentioned are chloromethyl, difluoromethyl, bromodifluoromethyl, trifluoromethyl, fluoroethyl, trifluoroethyl and perfluoroethyl.

In the tri(lower alkyl)silyl groups, the alkyl radicals can be identical or different. Examples which may be mentioned are the groups trimethylsilyl, ethyldimethylsilyl, n-propyldimethylsilyl, tert-butyldimethylsilyl, triethylsilyl and methyldiethylsilyl.

Examples which may be mentioned of $C_3$–$C_7$-cycloalkyl optionally substituted by lower alkyl are cyclopropyl, cyclobutyl, cyclopentyl, cyclohexyl, cycloheptyl, 4-methylcyclohexyl, 4-ethylcyclohexyl and 4-tert-butylcyclohexyl.

Examples which may be mentioned for lower alkanediyl, by itself or in combination with other groups, are the radicals

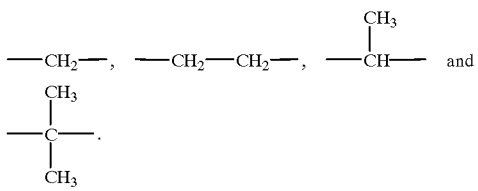

In di(lower alkyl)silyl, the alkyl radicals can be identical or different. Examples which may be mentioned are dimethylsilyl and diethylsilyl.

Examples of the novel compounds according to the invention are listed in Tables 1–1944.

TABLE 1

(Ia-31)

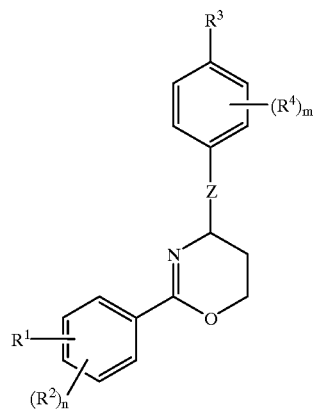

Compounds of Table 1 correspond to the general formula (Ia-31), in which R$^1$ = 2-F; (R$^2$)$_n$ = 6-F; (R$^4$)$_n$ = H; Z = a direct bond and R$^3$ = as listed in the following.

| Compound No. | R$^3$ |
|---|---|
| 1 | Cl |
| 2 | F |
| 3 | —C$_4$H$_9$-t |
| 4 | —C$_6$H$_{13}$-n |
| 5 | —C$_{12}$H$_{25}$-n |
| 6 | —C$_{10}$H$_{21}$-n |
| 7 | —C$_8$H$_{17}$-n |
| 8 | —C$_9$H$_{19}$-n |
| 9 | CF$_3$ |
| 10 | —CF$_2$CHF$_2$ |
| 11 | —CF$_6$H$_{13}$-n |
| 12 | —OC$_8$H$_{17}$-n |
| 13 | —OC$_{12}$H$_{25}$-n |
| 14 | —OCF$_3$ |
| 15 | —OCF$_2$CHF$_2$ |
| 16 | —OCH$_2$CF$_3$ |
| 17 | —OCF$_2$CHFCH$_3$ |
| 18 | —O(CH$_2$)$_8$Cl |
| 19 | —OCF$_2$CHFCF$_3$ |
| 20 | —CH$_2$CH$_2$—O—C$_2$H |

TABLE 1-continued (Ia-31)

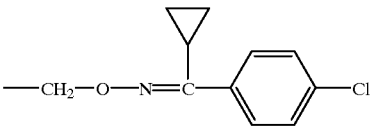

Compounds of Table 1 correspond to the general formula (Ia-31), in which $R^1$ = 2-F; $(R^2)_n$ = 6-F; $(R^4)_n$ = H; Z = a direct bond and $R^3$ = as listed in the following.

| Compound No. | $R^3$ |
|---|---|
| 21 | —CH$_2$CH$_2$—O—C$_4$H$_7$-n |
| 22 | —CH$_2$CH$_2$O—C$_6$H$_{13}$-n |
| 23 |  |
| 24 | —SC$_4$H$_9$-n |
| 25 | —SC$_6$H$_{13}$-n |
| 26 | —SC$_8$H$_{17}$-n |
| 27 | —SC$_{12}$H$_{25}$-n |
| 28 | —SCF$_3$ |
| 29 | —SCF$_2$CHF$_2$ |
| 30 | —SCF$_2$CHFCF$_3$ |
| 31 | —S(CH$_2$)$_5$Cl |
| 32 | 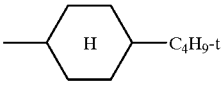 |
| 33 | 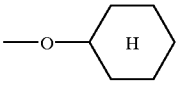 |
| 34 | 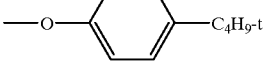 |
| 35 | 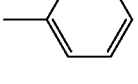 |
| 36 | 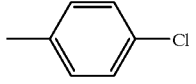 |

TABLE 1-continued (Ia-31)

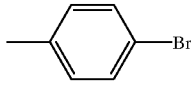

Compounds of Table 1 correspond to the general formula (Ia-31), in which $R^1$ = 2-F; $(R^2)_n$ = 6-F; $(R^4)_n$ = H; Z = a direct bond and $R^3$ = as listed in the following.

| Compound No. | $R^3$ |
|---|---|
| 37 | 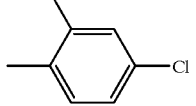 |
| 38 | 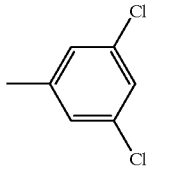 |
| 39 | 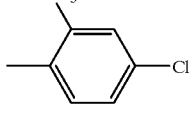 |
| 40 | 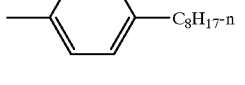 |
| 41 | 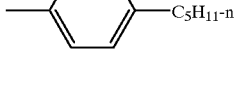 |
| 42 | 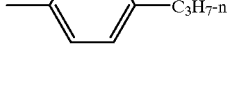 |
| 43 |  |
| 44 |  |

TABLE 1-continued

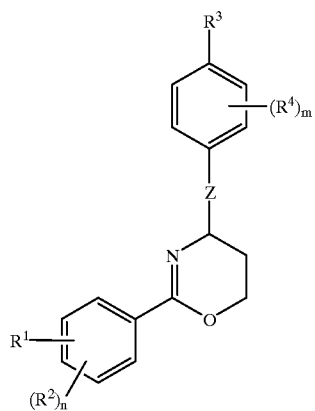

(Ia-31)

Compounds of Table 1 correspond to the general formula (Ia-31), in which $R^1$ = 2-F; $(R^2)_n$ = 6-F; $(R^4)_n$ = H; Z = a direct bond and $R^3$ = as listed in the following.

| Compound No. | $R^3$ |
|---|---|
| 45 | —⟨C₆H₄⟩—C₆H₁₃-n |
| 46 | —⟨C₆H₄⟩—C₄H₉-n |
| 47 | —⟨C₆H₄⟩—C₄H₉-i |
| 48 | —⟨C₆H₄⟩—C₄H₉-s |
| 49 | —⟨C₆H₃(2-Cl)⟩—CH₃ |
| 50 | —⟨C₆H₃(2-Cl)⟩—C₃H₇-n |
| 51 | —⟨C₆H₄⟩—OC₂H₅ |
| 52 | —⟨C₆H₄⟩—CF₃ |
| 53 | —⟨C₆H₃(2-Cl)⟩—CF₃ |
| 54 | —⟨C₆H₃(2-CH₃)⟩—CF₃ |
| 55 | —⟨C₆H₃(2-OCH₃)⟩—CF₃ |
| 56 | —⟨C₆H₄⟩—OCF₃ |
| 57 | —⟨C₆H₄⟩—OCHF₂ |
| 58 | —⟨C₆H₂(2,6-Cl₂)⟩—CF₃ |
| 59 | —⟨C₆H₂(2,6-(CH₃)₂)⟩—CF₃ |

TABLE 1-continued (Ia-31)

Compounds of Table 1 correspond to the general formula (Ia-31), in which $R^1$ = 2-F; $(R^2)_n$ = 6-F; $(R^4)_n$ = H; Z = a direct bond and $R^3$ = as listed in the following.

| Compound No. | $R^3$ |
|---|---|
| 60 | —CH$_2$—C$_6$H$_5$ |
| 61 | —CH$_2$—C$_6$H$_4$—F (4-) |
| 62 | —CH$_2$—C$_6$H$_4$—Cl (4-) |
| 63 | —CH$_2$—C$_6$H$_4$—Br (4-) |
| 64 | —CH$_2$—C$_6$H$_4$—C$_4$H$_9$-t (4-) |
| 65 | —CH$_2$—C$_6$H$_4$—C$_6$H$_{13}$-n (4-) |
| 66 | —CH$_2$—C$_6$H$_4$—C$_{12}$H$_{25}$-n (4-) |
| 67 | —CH$_2$—C$_6$H$_4$—OC$_2$H$_5$ (4-) |
| 68 | —CH$_2$—C$_6$H$_4$—CF$_3$ (4-) |
| 69 | —CH$_2$—C$_6$H$_4$—OCF$_3$ (4-) |
| 70 | —O—C$_6$H$_5$ |
| 71 | —O—C$_6$H$_4$—Cl (4-) |
| 72 | —O—C$_6$H$_4$—Br (4-) |
| 73 | —O—C$_6$H$_4$—CH$_3$ (4-) |
| 74 | —O—C$_6$H$_4$—C$_3$H$_7$-n (4-) |
| 75 | —O—C$_6$H$_4$—C$_3$H$_7$-i (4-) |
| 76 | —O—C$_6$H$_4$—OC$_2$H$_5$ (4-) |
| 77 | —O—C$_6$H$_3$(CH$_3$)(OCH$_3$) (2-CH$_3$, 4-OCH$_3$) |

TABLE 1-continued (Ia-31)

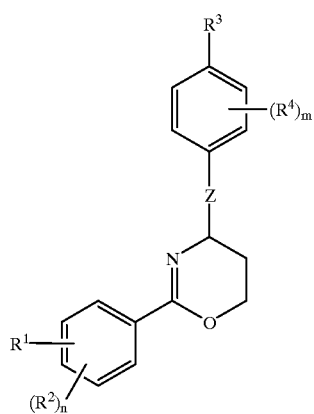

Compounds of Table 1 correspond to the general formula (Ia-31), in which $R^1$ = 2-F; $(R^2)_n$ = 6-F; $(R^4)_m$ = H; Z = a direct bond and $R^3$ = as listed in the following.

| Compound No. | $R^3$ |
|---|---|
| 78 | —O—⟨C6H3(Cl)⟩—OC2H5 |
| 79 | —O—⟨C6H3(Cl)⟩—OCH3 |
| 80 | —O—⟨C6H3(CH3)⟩—Cl |
| 81 | —O—⟨C6H2(Cl)2⟩—OCH3 |
| 82 | —O—⟨C6H4⟩—CH2CH2OC2H5 |
| 83 | —O—⟨C6H4⟩—CF3 |
| 84 | —O—⟨C6H3(CH3)⟩—CF3 |

TABLE 1-continued (Ia-31)

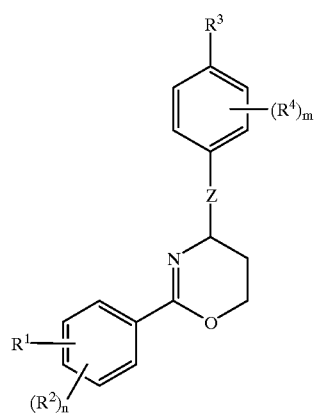

Compounds of Table 1 correspond to the general formula (Ia-31), in which $R^1$ = 2-F; $(R^2)_n$ = 6-F; $(R^4)_m$ = H; Z = a direct bond and $R^3$ = as listed in the following.

| Compound No. | $R^3$ |
|---|---|
| 85 | —O—⟨C6H3(OCH3)⟩—CF3 |
| 86 | —O—⟨C6H3(Cl)⟩—CF3 |
| 87 | —O—⟨C6H3(CH3)⟩—CF3 |
| 88 | —O—⟨C6H4⟩—OCF3 |
| 89 | —O—⟨C6H4⟩—OCHF2 |
| 90 | —O—⟨C6H4⟩—OCH2CF3 |
| 91 | —O—⟨C6H4⟩—OCH2CHF2 |
| 92 | —O—⟨C6H4⟩—OCF2CHClF |

TABLE 1-continued (Ia-31)

Compounds of Table 1 correspond to the general formula (Ia-31), in which $R^1$ = 2-F; $(R^2)_n$ = 6-F; $(R^4)_m$ = H; Z = a direct bond and $R^3$ = as listed in the following.

| Compound No. | $R^3$ |
|---|---|
| 93 | —O—C$_6$H$_4$—OCF$_2$CHFCF$_3$ |
| 94 | —O—C$_6$H$_4$—O(CH$_2$)$_4$Cl |
| 95 | —O—(2,6-Cl$_2$-4-CF$_3$-C$_6$H$_2$) |
| 96 | —O—(2,6-(CH$_3$)$_2$-4-CF$_3$-C$_6$H$_2$) |
| 97 | —O—(2,6-Cl$_2$-4-OCH$_3$-C$_6$H$_2$) |
| 98 | —O—(2,6-(CH$_3$)$_2$-4-OCH$_3$-C$_6$H$_2$) |
| 99 | —O—C$_6$H$_4$—SCF$_3$ |
| 100 | —O—C$_6$H$_4$—SCHF$_2$ |
| 101 | —O—C$_6$H$_4$—SCF$_2$CHF$_2$ |
| 102 | —O—C$_6$H$_4$—S(CH$_2$)$_4$Cl |
| 103 | —O—C$_6$H$_4$—SCH$_3$ |
| 104 | —O—(2-Cl-4-SCH$_3$-C$_6$H$_3$) |
| 105 | —OCH$_2$—C$_6$H$_4$—Cl |
| 106 | —OCH$_2$—C$_6$H$_4$—Br |

TABLE 1-continued (Ia-31)

Compounds of Table 1 correspond to the general formula (Ia-31), in which $R^1$ = 2-F; $(R^2)_n$ = 6-F; $(R^4)_n$ = H; Z = a direct bond and $R^3$ = as listed in the following.

| Compound No. | $R^3$ |
|---|---|
| 107 | —OCH$_2$—(2-Cl, 4-Cl-phenyl) |
| 108 | —OCH$_2$—(4-C$_4$H$_9$-t-phenyl) |
| 109 | —OCH$_2$—(4-CF$_3$-phenyl) |
| 110 | —OCH$_2$—(4-OCF$_3$-phenyl) |
| 111 | —OCH$_2$—(2-Cl, 4-CF$_3$-phenyl) |
| 112 | —OCH$_2$—(2-Cl, 4-OCF$_3$-phenyl) |
| 113 | —S—(phenyl) |
| 114 | —S—(4-Cl-phenyl) |
| 115 | —S—(4-Br-phenyl) |
| 116 | —S—(4-CF$_3$-phenyl) |
| 117 | —S—(4-OCF$_3$-phenyl) |
| 118 | —O—(3-Cl, 5-CF$_3$-pyridin-2-yl) |
| 119 | H |

Table 2

Table 2 contains the compounds of the general formula (Ia-31), in which $R^1$=2-F; $(R^2)_n$=6-F; $(R^4)_m$=2-Cl; Z=a direct bond and $R^3$ is as listed in Table 1.

Table 3

Table 3 contains the compounds of the general formula (Ia-31), in which $R^1$=2-F; $(R^2)_n$=6-F; $(R^4)_m$=2-CH$_3$; Z=a direct bond and $R^3$ is as listed in Table 1.

Table 4

Table 4 contains the compounds of the general formula (Ia-31), in which $R^1$=2-F; $(R^2)_n$=6-F; $(R^4)_m$=2-OCH$_3$; Z=a direct bond and $R^3$ is as listed in Table 1.

Table 5

Table 5 contains the compounds of the general formula (Ia-31), in which $R^1$=2-F; $(R^2)_n$=6-F; $(R^4)_m$=2-OC$_2$H$_5$; Z=a direct bond and $R^3$ is as listed in Table 1.

Table 6

Table 6 contains the compounds of the general formula (Ia-31), in which $R^1$=2-F; $(R^2)_n$=6-F; $(R^4)_m$=2,6-$Cl_2$; Z=a direct bond and $R^3$ is as listed in Table 1.

Table 7

Table 7 contains the compounds of the general formula (Ia-31), in which $R^1$=2-F; $(R^2)_n$=6-F; $(R^4)_m$=3,5-$Cl_2$; Z=a direct bond and $R^3$ is as listed in Table 1.

Table 8

Table 8 contains the compounds of the general formula (Ia-31), in which $R^1$=2-F; $(R^2)_n$=6-F; $(R^4)_m$=2-F; Z=a direct bond and $R^3$ is as listed in Table 1.

Table 9

Table 9 contains the compounds of the general formula (Ia-31), in which $R^1$=2-F; $(R^2)_n$=6-F; $(R^4)_m$=3,5-$F_2$; Z=a direct bond and $R^3$ is as listed in Table 1.

Table 10

Table 10 contains the compounds of the general formula (Ia-31), in which $R^1$=2-F; $(R^2)_n$=6-F; $(R^4)_m$=2,5-$Cl_2$; Z=a direct bond and $R^3$ is as listed in Table 1.

Table 11

Table 11 contains the compounds of the general formula (Ia-31), in which $R^1$=2-F; $(R^2)_n$=6-F; $(R^4)_m$=3-Cl; Z=a direct bond and $R^3$ is as listed in Table 1.

Table 12

Table 12 contains the compounds of the general formula (Ia-31), in which $R^1$=2-F; $(R^2)_n$=6-F; $(R^4)_m$=3-$CH_3$; Z=a direct bond and $R^3$ is as listed in Table 1.

Table 13

Table 13 contains the compounds of the general formula (Ia-31), in which $R^1$=2-F; $(R^2)_n$=6-F; $(R^4)_m$=3,5-$(CH_3)_2$; Z=a direct bond and $R^3$ is as listed in Table 1.

Table 14

Table 14 contains the compounds of the general formula (Ia-31), in which $R^1$=2-F; $(R^2)_n$=6-F; $(R^4)_m$=3-O—$C_6H_5$; Z=a direct bond and $R^3$ is as listed in Table 1.

Table 15

Table 15 contains the compounds of the general formula (Ia-31), in which $R^1$=2-F; $(R^2)_n$=6-F; $(R^4)_m$=3,5-$Cl_2$; 2F; Z=a direct bond and $R^3$ is as listed in Table 1.

Table 16

Table 16 contains the compounds of the general formula (Ia-31), in which $R^1$=2-F; $(R^2)_n$=6-F; $(R^4)_m$=2,3-$F_2$; Z=a direct bond and $R^3$ is as listed in Table 1.

Table 17

Table 17 contains the compounds of the general formula (Ia-31), in which $R^1$=2-F; $(R^2)_n$=6-F; $(R^4)_m$=2,5-$F_2$; Z=a direct bond and $R^3$ is as listed in Table 1.

Table 18

Table 18 contains the compounds of the general formula (Ia-31), in which $R^1$=2-F; $(R^2)_n$=6-F; Z=a direct bond and $R^3$ and $(R^4)_m$ together represent 3,4-$OCF_2$— or 3,4-$OCF_2CF_2O$—.

Tables 19 to 36

Each of Tables 19 to 36 contains the compounds of the general formula (Ia-31), in which $R^3$, $(R^4)_m$ and Z represent the meanings of Tables 1 to 18 and $R^1$=2-F; $(R^2)_n$=6-Cl.

Tables 37 to 54

Each of Tables 37 to 54 contains the compounds of the general formula (Ia-31), in which $R^3$, $(R^4)_m$ and Z represent the meanings of Tables 1 to 18 and $R^1$=2-Cl; $(R^2)_n$=6-Cl.

Tables 55 to 72

Each of Tables 55 to 72 contains the compounds of the general formula (Ia-31,) in which $R^3$, $(R^4)_m$ and Z represent the meanings of Tables 1 to 18 and $R^1$=2-F; $(R^2)_n$=4-F.

Tables 73 to 90

Each of Tables 73 to 90 contains the compounds of the general formula (Ia-31), in which $R^3$, $(R^4)_m$ and Z represent the meanings of Tables 1 to 18 and $R^1$=2-Cl; $(R^2)_n$=H.

Tables 91 to 108

Each of Tables 91 to 108 contains the compounds of the general formula (Ia-31), in which $R^3$, $(R^4)_m$ and Z represent the meanings of Tables 1 to 18 and $R^1$=2-F; $(R^2)_n$=H.

Tables 109 to 126

Each of Tables 109 to 126 contains the compounds of the general formula (Ia-31), in which $R^3$, $(R^4)_m$ and Z represent the meanings of Tables 1 to 18 and $R^1$=2-Cl; $(R^2)_n$=4-F.

Tables 127 to 144

Each of Tables 127 to 144 contains the compounds of the general formula (Ia-31), in which $R^3$, $(R^4)_m$ and Z represent the meanings of Tables 1 to 18 and $R^1$=2-F; $(R^2)_n$=4-Cl.

Tables 145 to 162

Each of Tables 145 to 162 contains the compounds of the general formula (Ia-31), in which $R^3$, $(R^4)_m$ and Z represent the meanings of Tables 1 to 18 and $R^1$=2-F; $(R^2)_n$=4,5-$F_2$.

Tables 163 to 180

Each of Tables 163 to 180 contains the compounds of the general formula (Ia-31), in which $R^3$, $(R^4)_m$ and Z represent the meanings of Tables 1 to 18 and $R^1$=2-$CH_3$; $(R^2)_n$=6-Cl.

Tables 181 to 198

Each of Tables 181 to 198 contains the compounds of the general formula (Ia-31), in which $R^3_1$ $(R^4)_m$ and Z represent the meanings of Tables 1 to 18 and $R^1$=2-Cl; $(R^2)_n$=3-Cl.

Tables 199 to 216

Each of Tables 199 to 216 contains the compounds of the general formula (Ia-31), in which $R^3$, $(R^4)_m$ and Z represent the meanings of Tables 1 to 18 and $R^1$=2F; $(R^2)_n$=4-$OCHF_2$.

Tables 217 to 234

Each of Tables 217 to 234 contains the compounds of the general formula (Ia-31), in which $R^3$, $(R^4)_m$ and Z represent the meanings of Tables 1 to 18 and $R^1$=2-F; $(R^2)_n$=4-$OCF_3$.

Tables 235 to 252

Each of Tables 235 to 252 contains the compounds of the general formula (Ia-31), in which $R^3$, $(R^4)_m$ and Z represent the meanings of Tables 1 to 18 and $R^1$=2-F; $(R^2)_n$=3,5,6-$F_3$.

Tables 252 to 270

Each of Tables 252 to 270 contains the compounds of the general formula (Ia-31), in which $R^3$, $(R^4)_m$ and Z represent the meanings of Tables 1 to 18 and $R^1$=2-F; $(R^2)_n$=5-F.

Tables 271 to 288

Each of Tables 271 to 288 contains the compounds of the general formula (Ia-31), in which $R^3$, $(R^4)_m$ and Z represent the meanings of Tables 1 to 18 and $R^1$=2-F; $(R^2)_n$=3,4,5-$F_3$.

Tables 289 to 306

Each of Tables 289 to 306 contains the compounds of the general formula (Ia-31), in which $R^3$, $(R^4)_m$ and Z represent the meanings of Tables 1 to 18 and $R^1$=2-F; $(R^2)_n$=4-$CF_3$.

Tables 307 to 324

Each of Tables 307 to 324 contains the compounds of the general formula (Ia-31), in which $R^3$, $(R^4)_m$ and Z represent the meanings of Tables 1 to 18 and $R^1$=2-F; $(R^2)_n$=4,6-$F_2$.

Tables 325 to 648

Each of Tables 325 to 648 contains the compounds of the general formula (Ia-31,) in which $R^1$, $(R^2)_n$, $R^3$ and $(R^4)_m$ represent the meanings of Tables 1 to 324 and Z denotes —$CH_2O$— (wherein O in bonded to the phenyl ring).

Tables 649 to 1296

Tables 649 to 1296 contain the compounds of tables 1 to 648, differing in that the substituent

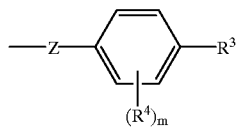

is in the 5-position of the oxazine ring.

Tables 1297 to 1944

Tables 1297 to 1944 contain the compounds of tables 1 to 648, differing in that the substituent

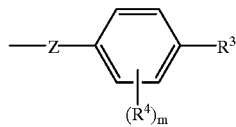

is in the 6-position of the oxazine ring.

If, for example, 3-amino-3-(4-fluorophenyl)-1-propanol and 2-chloro-4-fluoro-benzoic acid are used for carrying out process (a) according to the invention, the course of the reaction can be outlined by the following equation:

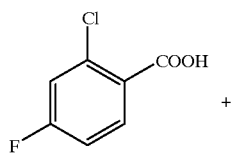

+

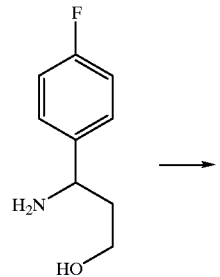

→

-continued

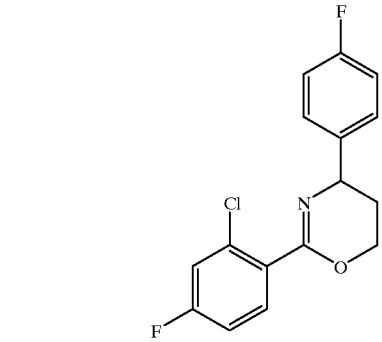

If, for example, N-(3-hydroxy-1-(2-methoxyphenyl)propyl)-2,5-difluorobenzamide is used as the starting compound and polyphosphoric acid (PPA) is used as the dehydrating agent for carrying out process (b) according to the invention, the course of the reaction can be outlined by the following equation:

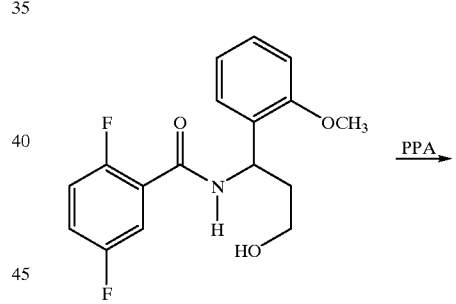

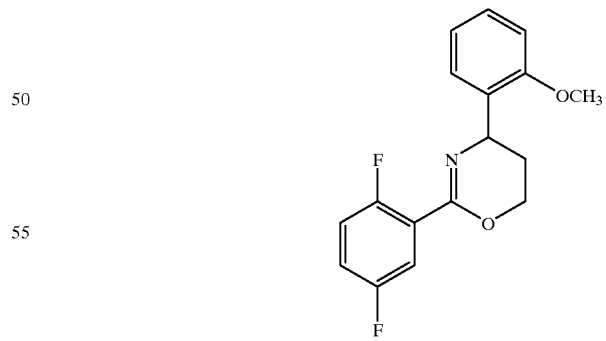

If, for example, N-(1-benzyl-3-chloro-2-methylpropyl)-2,3-difluoro-benzamide is used as the starting compound and triethylamine is used as the base for carrying out process (c) according to the invention, the course of the reaction can be outlined by the following equation:

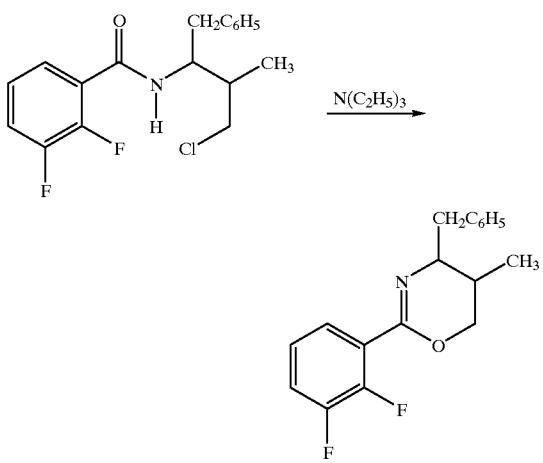

If, for example, N-(3-hydroxy-1-phenoxymethylpropyl)-2-chloro-6-fluoro-benzamide is used as the starting compound and phosphorus(V) sulfide is used as the thienylating agent for carrying out process (d) according to the invention, the course of the reaction can be outlined by the following equation:

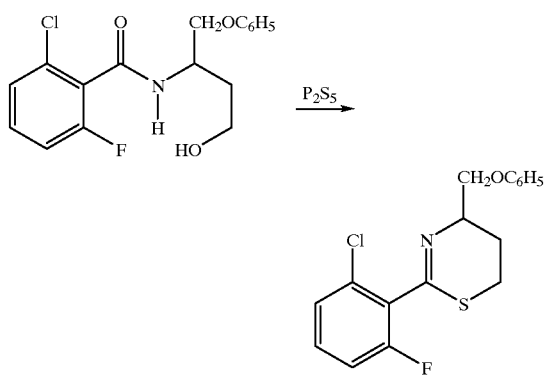

Formula (II) provides a general definition of the aminoalcohols to be used as starting substances in process (a) according to the invention for preparation of compounds of the formula (Ia). In formula (II), $B^1$, $D^1$, $E^1$, $G^1$, $J^1$ and $K^1$ preferably or in particular have those meanings which have already been mentioned above as preferred or as particularly preferred for $B^1$, $D^1$, $E^1$, $G^1$, $J^1$ and $K^1$ in connection with the description of the compounds of the formula (Ia).

The starting substances of the formula (II) are known and/or can be prepared by processes which are known per se (compare Heterocycles 9 (1978), 1277–1285; J. Org. Chem. 43 (1978), 2539–2541; Liebigs Ann. Chem. 1980, 122–139; Tetrahedron Lett. 26 (1985), 4971–4974).

The aminoalcohols of the formula (II) are obtained, for example, when suitable methoximinopropionic acid esters are reacted with reducing agents, such as, for example, lithiumaluminum hydride, if appropriate in the presence of a diluent, such as, for example, 1,2-dimethoxyethane, at temperatures between −20° C. and +100° C. (compare J. Org. Chem. 43 (1978), 2539–2541 and the Preparation Examples).

The methoximinopropionic acid esters required here as precursors can be obtained in the customary manner from corresponding keto esters and O-methyl-hydroxylamine or the hydrochloride thereof (compare the Preparation Examples).

Formula (III) provides a general definition of the carboxylic acids furthermore to be used as starting substances in process (a) according to the invention for preparation of compounds of the formula (Ia). In formula (III), $A^1$ preferably or in particular has that meaning which has already been given above as preferred or as particularly preferred for $A^1$ in connection with the description of the compounds of the formula (Ia).

The starting substances of the formula (III) are known organic synthesis chemicals.

Processes (a) and (b) according to the invention are carried out using a dehydrating agent. The dehydrating agents customary in organic chemistry can be employed. Sulfuric acid, polyphosphoric acid (PPA), phosphorus(V) oxide, dicyclohexylcarbodiimide (DCC), phosphorus(V) sulfide and the system triphenylphosphine/triethylamine/carbon tetrachloride can preferably be used.

Possible diluents for carrying out processes (a) to (d) according to the invention are the customary organic solvents. Solvents which can preferably be used are aliphatic, cycloaliphatic or aromatic, optionally halogenated hydrocarbons, such as, for example, benzine, benzene, toluene, xylene, chlorobenzene, dichlorobenzene, petroleum ether, hexane, cyclohexane, methylene chloride, chloroform or carbon tetrachloride; ethers, such as diethyl ether, diisopropyl ether, dioxane, tetrahydrofuran or ethylene glycol dimethyl or diethyl ether; ketones, such as acetone, butanone or methyl isobutyl ketone; nitriles, such as acetonitrile, propionitrile or benzonitrile; amides, such as N,N-dimethylformamide and N,N-dimethylacetamide, N-methyl-pyrrolidone or hexamethylphosphoric acid triamide; esters, such as methyl acetate or ethyl acetate, and sulfoxides, such as dimethyl sulfoxide, and if appropriate also alcohols, such as methanol or ethanol.

The reaction temperatures can be varied within a substantial range in carrying out process (a) according to the invention. The reaction is in general carried out at temperatures between 0° C. and 150° C., preferably at temperatures between 10° C. and 100° C.

Process (a) according to the invention is in general carried out under normal pressure. However, it is also possible to carry out the process under increased or reduced pressure—in general between 0.1 bar and 10 bar.

For carrying out process (a) according to the invention, the particular starting substances required are in general employed in approximately equimolar amounts. However, it is also possible for one of the two particular components employed to be used in a relatively large excess. The reactions are in general carried out in a suitable diluent in the presence of a dehydrating agent, and the reaction mixture is stirred at the particular temperature required for several hours. Working up in the processes according to the invention is in each case carried out by customary methods (compare the Preparation Examples).

In a particular embodiment of process (a) according to the invention, corresponding nitriles can also be employed instead of carboxylic acids of the formula (III), in which case a catalyst, such as, for example, zinc(II) chloride, is then preferably used instead of a dehydrating agent.

Formulae (IVa) and (IVb) provide general definitions of the amide-alcohols to be used as starting substances in processes (b) and (d) according to the invention for preparation of compounds of the formula (Ia). In formulae (IVa) and (IVb), $A^1$, $B^1$, $D^1$, $E^1$, $G^1$, $J^1$ and $K^1$ preferably or in particular have those meanings which have already been given above as preferred or as particularly preferred for $A^1$, $B^1$, $D^1$, $E^1$, $G^1$, $J^1$ and $K^1$ in connection with the description of the compounds of the formula (Ia).

The starting substances of the formulae (IVa) and (IVb) are known and/or can be prepared by processes which are known per se.

The amide-alcohols of the formulae (IVa) and (IVb) are obtained, for example, when acid chlorides derived from the carboxylic acids of the formula (III) are reacted with aminoalcohols of the formula (II) in the presence of an acid-binding agent, such as, for example, triethylamine, pyridine, potassium carbonate, sodium hydroxide or potassium t-butylate, and in the presence of a diluent, such as, for example, toluene, chlorobenzene, acetone or acetonitrile, at temperatures between 0° C. and 100° C. (compare the Preparation Examples).

The reaction temperatures can be varied within a substantial range in carrying out process (b) according to the invention. The reaction is in general carried out at temperatures between −20° C. and +150° C., preferably at temperatures between 0° C. and 100° C.

Process (b) according to the invention is in general carried out under normal pressure. However, it is also possible to carry out the process under increased or reduced pressure—in general between 0.1 bar and 10 bar.

For carrying out process (b) according to the invention for preparation of compounds of the formula (Ia), in general 1 to 20 mol, preferably 1 to 5 mol, of dehydrating agent are employed per mole of amide-alcohol of the formula (IVa) or (IVb).

In a preferred embodiment of process (b) according to the invention, the amide-alcohol of the formula (IVa) or (IVb) is initially introduced in a diluent and the dehydrating agent is then metered in. The reaction mixture is stirred at the required temperature until the reaction has ended and is then worked up in the customary manner (compare the Preparation Examples).

Formulae (Va) and (Vb) provide general definitions of the amide derivatives to be used as starting substances in process (c) according to the invention for preparation of compounds of the formula (Ia). In formulae (Va) and (Vb), $A^1, B^1, D^1, E^1, G^1, J^1$ and $K^1$ preferably or in particular have those meanings which have already been given above as preferred or as particularly preferred for $A^1, B^1, D^1, E^1, G^1, J^1$ and $K^1$ in connection with the description of the compounds of the formula (Ia); X preferably represents fluorine, chlorine, bromine, iodine, $C_1$–$C_4$-alkyl-sulfonyloxy, phenylsulfonyloxy or tolylsulfonyloxy, in particular chlorine, bromine, methylsulfonyloxy or tolylsulfonyloxy.

The starting substances of the formulae (Va) and (Vb) are known and/or can be prepared by processes which are known per se.

The amide derivative of the formulae (Va) or (Vb) are obtained when corresponding amide-alcohols of the formulae (IVa) or (IVb) are reacted with halogenating agents, such as, for example, thionyl chloride, phosphorus tribromide, phosphorus trichloride or phosphorus(V) chloride, if appropriate in the presence of a diluent, or with sulfonylating agents, such as, for example, methanesulfonyl chloride or p-toluenesulfonyl chloride, if appropriate in the presence of a diluent and a base.

Possible diluents for the halogenation are, for example, aromatic hydrocarbons, such as, for example, benzene, toluene and xylene, and halogenated hydrocarbons, such as, for example, methylene chloride, chloroform, carbon tetrachloride and dichloroethane. The halogenating agent can be employed in up to a five-fold excess.

The reaction temperature can be varied within a substantial range during the halogenation. The reaction is in general carried out between 0° C. and the boiling point of the diluent.

Possible diluents for the sulfonylation are, in addition to those described above as suitable for the halogenation reaction, are furthermore also, for example, ethers, such as, for example, diethyl ether or tetrahydrofuran.

Organic bases, such as, for example, triethylamine, N,N-dimethylaniline, pyridine and 4-N,N-dimethylaminopyridine, are preferably employed as the base for the sulfonylation.

In general 0.8 to 1.5 mol of base are employed per mole of compound to be sulfonylated.

The sulfonylation agent is in general employed in at least equimolar amounts.

Process (c) according to the invention is carried out in the presence of a base. All the customary inorganic or organic bases are suitable for this. Bases which can preferably be used are alkali metal or alkaline earth metal hydrides, hydroxides, amides, alcoholates, acetates, carbonates or bicarbonates, such as, for example, sodium hydride, sodium amide, sodium methylate, sodium ethylate, potassium tert-butylate, sodium hydroxide, potassium hydroxide, ammonium hydroxide, sodium acetate, potassium acetate, calcium acetate, ammonium acetate, sodium carbonate, potassium carbonate, potassium bicarbonate, sodium bicarbonate or ammonium carbonate, as well as tertiary amines, such as trimethylamine, triethylamine, tributylamine, N,N-dimethylaniline, pyridine, N-methylpiperidine, N,N-dimethylaminopyridine, diazabicyclooctane (DABCO), diazabicyclononene (DBN) or diazabicycloundecene (DBU).

The reaction temperatures can be varied within a substantial range in carrying out process (c) according to the invention. The reaction is in general carried out at temperatures between −20° C. and +150° C., preferably at temperatures between 0° C. and 100° C.

Process (c) according to the invention is in general carried out under normal pressure. However, it is also possible to carry out the process under increased or reduced pressure—in general between 0.1 bar and 10 bar.

For carrying out process (c) according to the invention for preparation of compounds of the formula (Ia), in general 1 to 3 mol, preferably 1.0 to 1.5 mol of a base are employed per mole of amide derivative of the formula (Va) or (Vb).

In a preferred embodiment of process (c) according to the invention, the amide derivative of the formula (Va) or (Vb) and a base are mixed in a suitable diluent; the mixture is stirred at the required temperature until the reaction has ended and is then worked up in the customary manner.

Process (d) according to the invention is carried out using a thienylating agent. Possible thienylating agents are the customary reagents suitable for conversion of organic oxygen compounds into corresponding sulfur compounds. Reagents which can preferably be used are phosphorus(V) sulfide, hydrogen sulfide and alkali metal salts thereof and so-called Lawesson's reagent.

The reaction temperatures can be varied within a substantial range in carrying out process (d) according to the invention. The reaction is in general carried out at temperatures between −20° C. and +150° C., preferably at temperatures between 0° C. and 100° C.

Process (d) according to the invention is in general carried out under normal pressure. However, it is also possible to carry out the process under increased or reduced pressure—in general between 0.1 bar and 10 bar.

For carrying out process (d) according to the invention for preparation of compounds of the formula (Ia), in general 1 to 5 mol, preferably 1.0 to 2.5 mol, of a thienylating agent are employed per mole of amide-alcohol of the formula (IVa) or (IVb).

In a preferred embodiment of process (d) according to the invention, the amide-alcohol of the formula (IVa) or (IVb) is initially introduced in a diluent and the thienylating agent is then metered in. The reaction mixture is then stirred at the suitable reaction temperature until the reaction has ended and is then worked up in the customary manner.

The active compounds which can be used according to the invention are suitable for combating animal pests, preferably arthropods and nematodes, in particular insects and arachnids, which occur in agriculture, in forests, in the protection of stored products and of materials, and in the hygiene sector. They are active against normally sensitive and resistant species and against all or individual development stages. The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and Scutigera spec.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blattella germanica, Acheta domeaticus,* Gryllotalpa spp., *Locusta migratoria migratorioides, Melanoplus differentialis* and *Schistocerca gregaria.*

From the order of the Dermaptera, for example, *Forficula auricularia.*

From the order of the Ioptera, for example, Reticulitermes spp..

From the order of the Anoplura, for example, *Phylloxera vastatrix,* Pemphigus spp., *Pediculus humanus corporis,* Haematopinus spp. and Linognathus spp.

From the order of the Mallophaga, for example, Trichodectes spp. and Damalinea spp.

From the order of the Thysanoptera, for example, *Hercino-thrips femoralis* and *Thrips tabaci.*

From the order of the Heteroptera, for example, Eurygaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Spodoptera exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.*

From the order of the Coleoptera, for example, *Anobium punctatum, Rhizopertha dominica, Acanthoscelides obtectus, Bruchidius obtectus, Hylotrupes bajulus, Agelastica alni, Leptinotarsa decemlineata, Phaedon cochleariae,* Diabrotica Bpp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica.*

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppoboaca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.*

From the order of the Siphonaptera, for example, *Xenopsylla cheopis* and Ceratophyllus spp..

From the order of the Arachnida, for example, *Scorpio maurus* and *Lactrodectus mactans.*

From the order of the Acarina, for example, *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp..

From the order of Blattaria, for example, *Periplaneta japonica, Periplaneta americana* and *Blattella germanica.*

The plant-parasitic nematodes include Pratylenchus spp., *Radopholus similis, Ditylenchus dipsaci, Tylenchulus semipenetrans,* Heterodera spp., Meloidogyne spp., Aphelenchoides spp., Longidorus spp., Xiphinema spp. and Trichodorus spp.

There may furthermore be mentioned *Myzus persicae, Lipaphis erysimi, Aphis citrocola, Nippolachnus piri, Nezara antennata, Cletus punctiger* and *Riptortus clavatus; Scirtothrips dorsalis, Thrips palmi* and *Ponticulothrips diospyrosi; Oxya yezoensis* and *Locusta migratoria; Anomala cuprea, Oulema oryzae, Lissorhoptrus oryzophilus* and *Epilachna vigintioctomaculata; Musca domestica* and *Culex pipiens; Plutella xylostella, Spodoptera litura* and *Chilo suppressalis; Tetranychus urticae, Tetranychus kanzawai, Panonychus ulmi, Panonychus citri, Dermatophagoides farinae, Tyrophagus putrescentiae, Polyphagotarsonemus latus, ornithonyssus bacoti, Ixodes ovatus* and *Haemaphysalis longicornis; Pthirus pubis; Pulex irritans* and *Ctenocephalides canis; Peticulitermes speratus* and *Coptotermes formosanus.*

The active compounds can be converted into the customary formulations, such as solutions, emulsions, wettable powders, suspensions, powders, dusts, free-flowing compositions, pastes, soluble powders, granules, suspension/emulsion concentrates, natural and synthetic materials impregnated with active compound, very fine capsules in polymeric substances and in coating compositions for seed, and furthermore into formulations used with burning equipment, such as fumigating cartridges, fumigating cans, fumigating coils, poisonous baits and the like, as well as ULV cold mist and warm mist formulations.

These formulations are produced in a known manner, for example by mixing the active compounds with extenders, that is, liquid solvents and/or solid carriers, optionally with the use of surface-active agents, that is, emulsifying agents and/or dispersing agents, and/or foam-forming agents and/or stabilizers.

In the case of the use of water as an extender, organic solvents can, for example, also be used as auxiliary solvents. As liquid solvents, there are suitable in the main: aromatics, such as xylene, toluene, trimethylbenzene or alkylnaphthalenes, chlorinated aromatics or chlorinated aliphatic hydrocarbons, such as chlorobenzenes, dichloroethane, trichloroethane, chloroethylenes or methylene chloride, aliphatic hydrocarbons, such as cyclohexane, hexane or paraffins, for example mineral oil fractions, mineral and vegetable oils, such as soy bean and olive oil, alcohols, such as butanol, methanol, phenoxyethanol or glycol as well as their ethers and esters, ketones, such as acetone, methyl ethyl ketone, methyl isobutyl ketone or cyclohexanone, ethers, such as diethyl ether, tetrahydrofuran or dioxane, nitriles, such as acetonitrile, esters, such as ethyl acetate, strongly polar solvents, such as dimethylformamide and dimethyl sulfoxide, as well as water; by liquefied gaseous extenders or carriers are meant those liquids which are gaseous at ambient temperature and under atmospheric pressure, for example aerosol propellants, such as halogenated hydrocarbons as well as butane, propane, nitrogen and carbon dioxide; as solid carriers there are suitable:

for example ammonium salts and ground natural minerals, such as kaolins, clays, talc, chalk, quartz, attapulgite; montmorillonite or diatomaceous earth, and ground synthetic minerals, such as highly-disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as starches, sawdust, soy bean flour, fish meal, wheat flour, coconut shells, maize cobs and tobacco stalks; as emulsifying and/or foam-forming agents there are suitable: for example nonionic and anionic emulsifiers, such as polyoxy alkylene alkyl ethers, polyoxyalkylene alkylaryl ethers, polyoxyethylene fatty acid esters, polyoxyethylene fatty alcohol ethers, for example alkylaryl polyglycol ether, alkylsulfonates, alkyl sulfates, arylsulfonates, alkylarylsulfonates, polyoxyalkylenealkylarylsulfonates as well as albumen hydrolysis products; as dispersing agents and adhesion promoters there are suitable: for example lignin-sulfite waste liquors, methylcellulose, naphthalenesulfonic acid/formalin condensates, starches, montmorillonite, synthetic water-soluble macromolecules, carboxymethylcellulose and natural and synthetic polymers in the form of powders, granules or latices, such as gum arabic, polyvinyl alcohol and polygumvinyl acetate, as well as natural phospholipids, such as cephalins and lecithins, and synthetic phospholipids. Other additives can be mineral and vegetable oils.

Stabilizers which may be mentioned are, for example, phosphoric acid esters, glycols, nonionic surface-active agents, aromatic diamines, vegetable oils and epoxidized oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.01 and 95 percent by weight of active compound, preferably between 0.5 and 90%.

These values can also vary within a substantial range, depending on the formulation used. For example, in the case of emulsions, wettable powders, free-flowing compositions and the like, the formulations can contain the active compounds in a concentration of 0.01 to 50% by weight, preferably 0.1 to 20% by weight, and in the case of powders, granules and the like, they can contain the active compounds in a concentration of 0.01 to 20% by weight, preferably 0.1 to 10% by weight.

The amount of compounds of the formula (I) applied depends on the nature of the active compound, the use form and the magnitude of pest infestation.

In agriculture, in general 1 to 10,000 g, preferably 10 to 1000 g per hectare are used. In the case of the abovementioned emulsions, wettable powders, free-flowing compositions and the like, these can usually be diluted 1000- to 10,000-fold and used in an amount of 1000 to 10,000 liters per hectare.

In the case of powders, granules and the like, in general 2 to 40 kg are used per hectare.

In the hygiene sector and against insects, the compositions are used such that 0.005 to 100 g, preferably 0.01 to 50 g, of active compound are applied per $m^2$.

The active compounds according to the invention can be present in their commercially available formulations and in the use forms, prepared from the formulations, as a mixture with other active compounds, such as insecticides, attractants, sterilizing agents, acaricides, nematicides, fungicides, growth-regulating substances or herbicides. The insecticides include, for example, phosphates, carbamates, carboxylates, chlorinated hydrocarbons, phenylureas, substances produced by microorganisms and the like.

The following compounds may be mentioned:

acrinathrin, alphamethrin, betacyfluthrin, bifenthrin, brofenprox, cis-resmethrin, clocythrin, cycloprothrin, cyfluthrin, cyhalothrin, cypermethrin, deltamethrin, esfenvalerate, etofenprox, fenpropathrin, fenvalerate, flucythrinate, fluvalinate, lambda-cyhalothrin, permethrin, pyresmethrin, pyrethrum, silafluofen, tralomethrin, zetamethrin, alanycarb, bendiocarb, benfuracarb, bufencarb, butocarboxim, carbaryl, cartap, ethiofencarb, fenobucarb, fenoxycarb, isoprocarb, methiocarb, methomyl, metolcarb, oxamyl, pirimicarb, promecarb, propoxur, terbam, thiodicarb, thiofanox, trimethacarb, XMC, xylylcarb, acephate, azinphos A, azinphos M, bromophos A, cadusafos, carbophenothion, chlorfenvinphos, chlormephos, chlorpyrifos, chlorpyrifos M, cyanophos, demeton M, demeton-S-methyl, demeton S, diazinon, dichlorvos, dicliphos, dichlorfenthion, dicrotophos, dimethoate, dimethylvinphos, dioxathion, disulfoton, edifenphos, ethion, etrimphos, fenitrothion, fenthion, fonophos, formothion, heptenophos, iprobenfos, isazophos, isoxathion, phorate, malathion, mecarbam, mervinphos, mesulfenphos, methacrifos, methamidophoo, naled, omethoate, oxydemeton M, oxydeprofos, parathion A, parathion M, phenthoate, phorate, phosalone, phosmet, phosphamdon, phoxim, pirimiphos A, pirimiphos M, propaphos, prothiophos, prothoate, pyraclophos, pyridaphenthion, quinalphos, salithion, sebufos, sulfotep, sulprofos, tetrachlorvinphos, temephos, thiomethon, thionazin, trichlorfon, triazophos, vamidothion, DMTP (O,O-dimethyl S-[5-methoxy-1,3,4-thiadiazol-2(3H)-onyl-(3)-methyl]dithiophosphate), DDVP (dimethyl 2,2-dichlorovinyl phosphate), CYAP (O,O-dimethyl O-4-cyanophenyl thiophosphate), buprofezin, chlorfluazuron, diflubenzuron, flucycloxuron, flufenoxuron, hexaflumuron, pyriproxifen, tebufenozide, teflubenzuron, triflumuron, imidacloprid, nitenpyram, N-[(6-chloro-3-pyridinyl) methyl]-N'-cyano-N-methylethaneimide-amide (NI-25), abamectin, amitrazin, avermectin, azadirachtin, bensultap, Bacillus thuringiensis, cyromazine, diafenthiuron, emamectin, ethofenprox, fenpyrad, fipronil, flufenprox, lufenuron, metaldehyde, milbemectin, pymetrozine, tebufenpyrad, triazuron, aldicarb, bendiocarb, benfuracarb, carbofuran, carbosulfan, chlorethoxyfos, cloethocarb, disulfoton, ethophrophos, etrimphos, fenamiphos, fipronil, fonofos, fosthiazate, furathiocarb, HCH, isazophos, isofenphos, methiocarb, monocrotophos, nitenpyram, oxamyl, phorate, phoxim, prothiofos, pyrachlofos, sebufos, silafluofen, tebupirimphos, tefluthrin, terbufos, thiodicarb, thiafenox, azocyclotin, butylpyridaben, clofentezine, cyhexatin, difenthiuron, diethion, emamectin, fenazaquin, fenbutatin oxide, fenothiocarb, fenpropathrin, fenpyrad, fenpyroximate, fluazinam, fluazuron, flucycloxuron, flufenoxuron, fluvalinate, fubfenprox, hexythiazox, ivemectin, methidathion, monocrotophos, moxidectin, naled, phosalone, profenofos, pyraclofos, pyridaben, pyrimidifen, tebufenpyrad, thuringiensin, triarathene and also 4-bromo-2-(4-chlorophenyl)-1-(ethoxymethyl)-5-(trifluoromethyl)-1H-pyrrole-3-carbonitrile (AC 303630), dicotol, chlorobenzilate, bromopropylate, chlorofenson, BPPS.

Particularly favorable mixing partners are furthermore, for example, the following:

Fungicides:

2-aminobutane; 2-anilino-4-methyl-6-cyclopropyl-pyrimidine; 2',6'-dibromo-2-methyl-4'-trifluoromethoxy-4'-trifluoro-methyl-1,3-thiazole-5-carboxanilide; 2,6-dichloro-N-(4-trifluoromethylbenzyl)-benzamide; (E)-2-methoxyimino-N-methyl-2-(2-phenoxyphenyl)-acetamide; 8-hydroxyquinoline sulfate; methyl (E)-2-{2-[6-(2-cyanophenoxy)-pyrimidin-4-yloxy]-phenyl}-3-methoxyacrylate; methyl (E)-methoximino[alpha-(o-tolyloxy)-o-tolyl]acetate; 2-phenylphenol (OPP), aldimorph, ampropylfos, anilazine, azaconazole, benalaxyl, benodanil, benomyl, binapacryl, biphenyl, bitertanol, blasticidin-S, bromuconazole, bupirimate, buthiobate, calcium polysulfide, captafol, captan, carbendazime, carboxine, chinomethionate (quinomethionate), chloroneb, chloropicrin, chlorothalonil, chlozolinate, cufraneb, cymoxanil, cyproconazole, cyprofuram, dichlorophen, diclobutrazole, diclofluanid, diclomezin, dicloran, diethofencarb, difenoconazole, dimethirimol, dimethomorph, diniconazole, dinocap, diphenylamine, dipyrithione, ditalimfos, dithianon, dodine, drazoxolon, edifenphos, epoxyconazole, ethirimol, etridiazole, fenarimol, fenbuconazole, fenfuram, fenitropan, fenpiclonil, fenpropidin, fenpropimorph, fentin acetate, fentin hydroxide, ferbam, ferimzone, fluazinam, fludioxonil, fluoromide, fluquinconazole, flusilazole, flusulfamide, flutolanil, flutriafol, folpet, fosetyl-aluminum, fthalide, fuberidazole, furalaxyl, furmecyclox, guazatine, hexachlorobenzene, hexaconazole, hymexazole, imazalil, imibenconazole, iminoctadin, iprobenfos (IBP), iprodione, isoprothiolan, kasugamycin, copper formulations, such as: copper hydroxide, copper naphthenate, copper oxychloride, copper sulfate, copper oxide, oxine-copper and Bordeaux mixture, mancopper, mancozeb, maneb, mepanipyrim, mepronil, metalaxyl, metconazole, methasulfocarb, methfuroxam, metiram, metsulfovax, myclobutanil, nickel dimethyldithiocarbamate, nitrothal-isopropyl, nuarimol, ofurace, oxadixyl, oxamocarb, oxycarboxin, pefurazoate, penconazole, pencycuron, phosdiphen, phthalide, pimaricin, piperalin, polycarbamate, polyoxin, probenazole, prochloraz, procymidon, propamocarb, propiconazole, propineb, pyrazophos, pyrifenox, pyrimethanil, pyroquilon, quintozen (PCNB), sulfur and sulfur formulations, tebuconazole, tecloftalam, tecnazen, tetraconazole, thiabendazole, thicyofen, thiophanate-methyl, thiram, tolclophos-methyl, tolylfluanid, triadimefon, triadimenol, triazoxide, trichlamid, tricyclazole, tridemorph, triflumizole, triforin, triticonazole, validamycin A, vinclozolin, zineb, ziram.

Bactericides:

Bronopol, dichlorophen, nitrapyrin, nickel dimethyldithiocarbamate, kasugamycin, octhilinon, furancarboxylic acid, oxytetracycline, probenazole, streptomycin, tecloftalam, copper sulfate and other copper formulations.

Attractants which may be mentioned are, for example, benzoic acid, 4-allyl-2-methoxyphenol and 4-(p-acetoxyphenyl)-2-butanone.

The active compounds which can be used according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

The active compounds which can be used according to the invention are not only active against plant, hygiene and stored product pests, but also, in the veterinary medicine sector, against animal parasites (ectoparasites and endoparasites), such as scaly ticks, Argasidae, scab mites, Trombidae, flies (stinging and sucking), parasitic fly larvae, lice, hair lice, bird lice, fleas and endoparasitic worms. For example, they show an outstanding activity against ticks, such as, for example, Boophilus microplus.

The active compounds of the formula (I) which can be used according to the invention are also suitable for combating arthropods which attack agricultural livestock, such as, for example, cattle, sheep, goats, horses, pigs, donkeys, camels, buffalo, rabbits, chickens, turkeys, ducks, geese, honey bees, other domestic animals such as, for example, dogs, cats, cage birds, aquarium fish and so-called experimental animals, such as, for example, hamsters, guinea pigs, rats and mice. By combating these arthropods, it is intended to reduce deaths and reduced performance (with regard to meat, milk, wool, hides, eggs, honey and the like), so that more economical and simpler animal keeping is possible by using the active compounds according to the invention.

In the veterinary sector, the active compounds according to the invention are administered in a known manner by enteral administration in the form of, for example, tablets, capsules, drinks, drenches, granules, pastes, boli, the feed-through method, suppositories, by parenteral administration, such as, for example, by injection (intramuscular, subcutaneous, intravenous, intraperitoneal and the like), implants, by nasal administration, by dermal administration, for example in the form of dipping or bathing, spraying, pouring-on and spotting-on, washing, dusting, and with the aid of shaped articles containing active compound, such as collars, ear tags, tail tags, limb bands, halters, marking devices and the like.

When used on livestock, poultry, domestic animals and the like, the active compounds of the formula (I) can be used as formulations (for example powders, emulsions, free-flowing compositions) which contain the active compounds in an amount of 1 to 80% by weight directly or after 100- to 10,000-fold dilution, or they can be used as a chemical bath.

The preparation and use of the substances according to the invention is illustrated by the following Examples.

PREPARATION EXAMPLES

Example 1

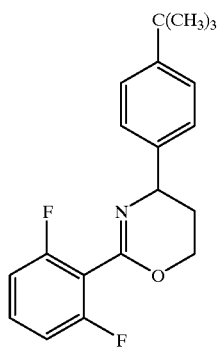

4.5 g (82% pure material: 10.6 mmol) of N-[3-hydroxy-1-(4-t-butyl-phenyl)-propyl]-2,6-difluoro-benzamide are dissolved in 65 ml of toluene, and thionyl chloride (4.5 g, 37.8 mmol) is added. The reaction mixture is subsequently stirred for 3 hours at 80° C. and then concentrated. The residue is taken up in 65 ml of methanol, and a solution of sodium hydroxide (1.55 g, 38.8 mmol) in 8.5 ml of water is added at 60° C. in the course of 15 minutes. The mixture is stirred at 60° C. for 1 hour and then cooled, diluted with water and extracted with methylene chloride. The crude product thus obtained is chromatographed on silica gel using the mobile phase cyclohexane/ethyl acetate 3:1.

1.7 g (49% of theory) of 4-(4-t-butylphenyl)-2-(2,6-difluorophenyl)-5,6-dihydro-4H-1,3-oxazine are obtained as a yellow oil of refractive index $n_D^{22}=1.5405$.

Example 2

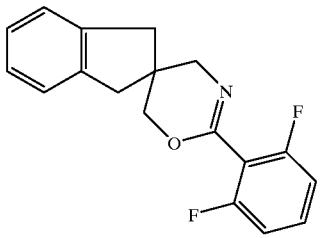

5.5 g (11.6 mmol) of 83% pure 2-(2,6-difluorobenzamido) methyl-2-mesyloxymethylindane are dissolved in 120 ml of dry tetrahydrofuran, and 1.87 g (16.7 mmol) of potassium tert-butylate are introduced at 0° C. The mixture is stirred at 0° C. for 15 minutes and then at room temperature for one hour. Thereafter, the mixture is evaporated and the residue is partitioned between a mixture of 370 ml of water and 700 ml of diethyl ether. The organic phase is separated off and the aqueous phase is subsequently extracted twice more with ether. The combined extracts are dried with $Na_2SO_4$ and evaporated. For purification, the residue is chromatographed over silica gel using methylene chloride/ethyl acetate (98:2 v/v). Yield: 0.94 g, melting point 68° C.

The following azines of the formula (I) are obtained in a corresponding manner and in accordance with the general preparation data:

| Ex. No. | Compound | Physical Constants |
|---|---|---|
| 3 | ![structure] | m.p. 112–116° C. |
| 4 | ![structure] | m.p. 60° C. |

-continued

| Ex. No. | Compound | Physical Constants |
|---|---|---|
| 5 | 2-(2,6-difluorophenyl)-5-methyl-6-(4-chlorophenyl)-5,6-dihydro-4H-1,3-oxazine | Oil |
| 6 | 2-(2,6-difluorophenyl)-5-(4-chlorophenyl)-5,6-dihydro-4H-1,3-oxazine | m.p. 88° C. |
| 7 | 2-(2,6-difluorophenyl)-4-(4-methoxyphenyl)-6-phenyl-5,6-dihydro-4H-1,3-oxazine | Oil |
| 8 | 2-(2,6-difluorophenyl)-5-(2-chlorophenyl)-5,6-dihydro-4H-1,3-oxazine | Oil |
| 9 | 2-(2,6-difluorophenyl)-4-methyl-6-phenyl-5,6-dihydro-4H-1,3-oxazine | Oil |
| 10 | 2-(2,6-difluorophenyl)-5,5-diethyl-5,6-dihydro-4H-1,3-oxazine | Oil |

-continued
| Ex. No. | Compound | Physical Constants |
|---|---|---|
| 11 | 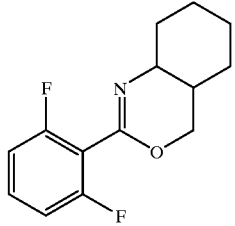 | Oil |
| 12 | 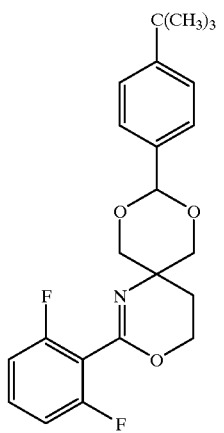 | m.p. 138° C. |
| 13 | 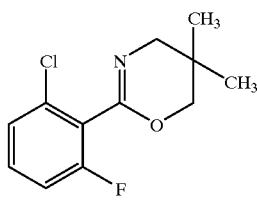 | m.p. 72° C. |
| 14 | 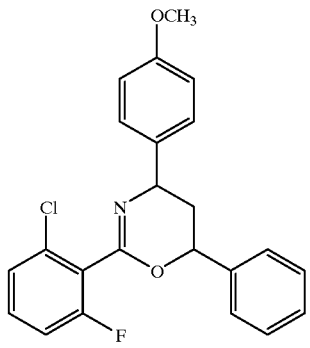 | log p*** 4.29 |

-continued

| Ex. No. | Compound | Physical Constants |
|---|---|---|
| 15 | 4-([1,1'-biphenyl]-4-yl)-2-(2,4-difluorophenyl)-5,6-dihydro-4H-1,3-oxazine | m.p. 105–106° C. |
| 16 | 4-([1,1'-biphenyl]-4-yl)-2-(2,4,5-trifluorophenyl)-5,6-dihydro-4H-1,3-oxazine | m.p. 130–131° C. |
| 17 | 2-(2-chloro-4-fluorophenyl)-4-(2-fluorophenyl)-5,6-dihydro-4H-1,3-oxazine | $n_D^{20}$ 1.572 |
| 18 | 4-{[(4-tert-butylphenyl)sulfonyl]methyl}-2-(2,6-difluorophenyl)-5,6-dihydro-4H-1,3-oxazine | log P 3.69 |

-continued

| Ex. No. | Compound | Physical Constants |
|---|---|---|
| 19 | 2-(2,6-difluorophenyl)-4-{[(4-(2,2-dimethylpropoxy)phenyl)thio]methyl}-5,6-dihydro-4H-1,3-oxazine (aryl = 4-OCH₂C(CH₃)₃-phenyl) | log P 5.25 |
| 20 | 2-(2,6-difluorophenyl)-4-{[(4-methoxyphenyl)thio]methyl}-5,6-dihydro-4H-1,3-oxazine (aryl = 4-OCH₃-phenyl) | log P 3.44 |
| 21 | 2-(2,6-difluorophenyl)-4-{[(4-tert-butylphenyl)thio]methyl}-5,6-dihydro-4H-1,3-oxazine (aryl = 4-C(CH₃)₃-phenyl) | log P 4.89 |
| 22 | 2-(2,6-difluorophenyl)-4-{[(4-fluorophenyl)thio]methyl}-5,6-dihydro-4H-1,3-oxazine (aryl = 4-F-phenyl) | log P 3.59 |

-continued

| Ex. No. | Compound | Physical Constants |
|---|---|---|
| 23 | (2-(2,6-difluorophenyl)-4-{[(4-(SCH₂C(CH₃)₃)phenyl)thio]methyl}-5,6-dihydro-4H-1,3-oxazine) | log P 5.43 |
| 24 | 2-(2,6-difluorophenyl)-4-(4'-bromobiphenyl-4-yl)-5,6-dihydro-4H-1,3-oxazine | m.p. 134–138° C. |
| 25 | 2-(2,6-difluorophenyl)-4-(4-methoxybenzyl)-5,6-dihydro-4H-1,3-oxazine | δ[ppm]*<br>H-4 3.75<br>H-5 1.7; 1.9<br>H-6 4.25<br>H-α 2.6; 3.2 |

-continued
| Ex. No. | Compound | Physical Constants |
|---|---|---|
| 26 | 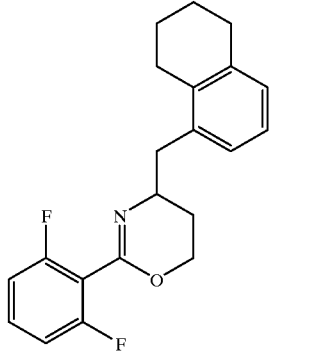 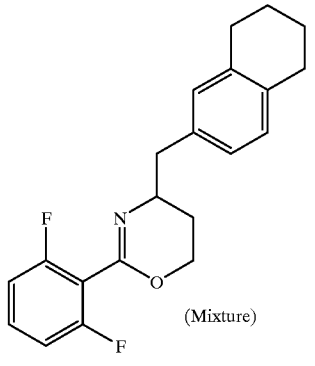 (Mixture) | δ[ppm]<br>H-4 3.75<br>H-5 1.7; 1.9<br>H-6 4.3–4.4<br>H-α 2.60; 3.2 |
| 27 | 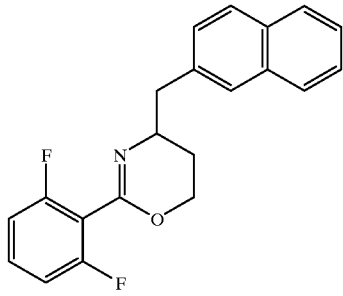 | δ[ppm]<br>H-4 3.75<br>H-5 1.65; 1.75<br>H-6 4.15<br>H-α 2.75; 3.3 |
| 28 |  | δ[ppm]<br>H-4 3.75<br>H-5 1.7; 1.9<br>H-6 4.3<br>H-α 2.6; 3.2 |

-continued
| Ex. No. | Compound | Physical Constants |
|---|---|---|
| 29 | 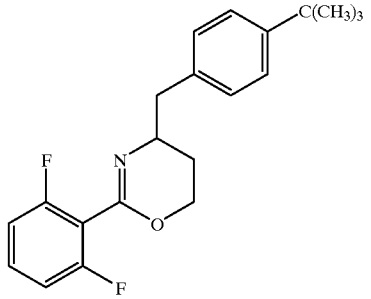 | m.p. 73° C. |
| 30 | 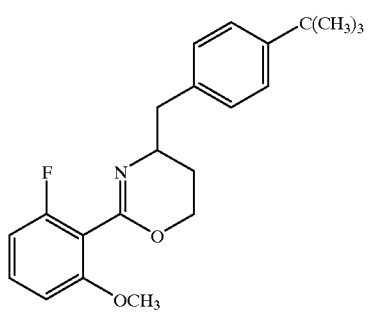 | δ[ppm]<br>H-4 3.65<br>H-5 1.6; 1.85<br>H-6 4.2<br>H-α 2.60; 2.85<br>(DMSO—d$_6$) |
| 31 | 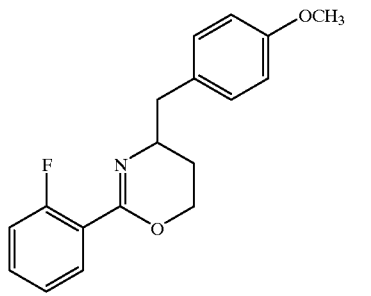 | δ[ppm]<br>H-4 3.7<br>H-5 1.7; 1.9<br>H-6 4.2–4.3<br>H-α 2.65; 3.15 |
| 32 | 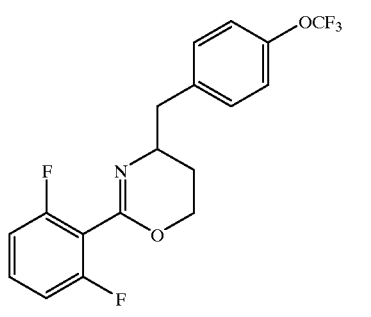 | δ[ppm]<br>H-4 3.75<br>H-5 1.75; 1.9<br>H-6 4.3<br>H-α 2.7; 3.15 |

Compounds of the formula (Ia-30)
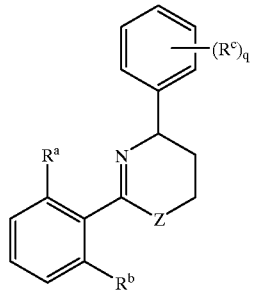
(Ia-30)
| Ex. No. | Z | $R^a$ | $R^b$ | $(R^c)_q$ | m.p. or $n_D^{25}$ |
|---|---|---|---|---|---|
| 33 | O | H | F | H | 1.5856 |
| 34 | O | H | Cl | H | 1.5872 |
| 35 | O | F | F | H | 1.5566 |
| 36 | O | Cl | F | H | 1.5764 |
| 37 | O | Cl | Cl | H | 1.5978 |
| 38 | S | H | F | H | 1.5940 |
| 39 | S | H | Cl | H | 1.5946 |
| 40 | O | H | Cl | 2-F | 1.5806 |
| 41 | O | F | F | 2-F | 1.5451 |
| 42 | O | Cl | F | 2-F | 1.5516 |
| 43 | O | F | F | 3-F | 1.5437 |
| 44 | O | Cl | F | 3-F | 1.5616 |
| 45 | O | H | Cl | 4-F | 1.5874 |
| 46 | O | F | F | 4-F | 1.5784 |
| 47 | O | Cl | F | 4-F | 1.5650 |
| 48 | O | F | F | 2-F, 4-F | 1.5396 |
| 49 | O | Cl | F | 2-F, 4-F | 1.5540 |
| 50 | O | F | F | 2-F, 4-Cl | 1.5782 |
| 51 | O | F | F | 2-F, 4-$(CH_2)_4CH_3$ | 1.5282 |
| 52 | O | F | F | 2-F, 4-$(CH_2)_5CH_3$ | 1.5281 |
| 53 | O | F | F | 2-F, 4-$(CH_2)_6CH_3$ | 1.5238 |
| 54 | O | F | F | 2-F, 4-$(CH_2)_7CH_3$ | 1.5211 |
| 55 | O | Cl | F | 2-F, 4-$(CH_2)_7CH_3$ | 1.5318 |
| 56 | O | Cl | F | 2-F, 4-$OCH_2CH_3$ | 1.5612 |
| 57 | O | F | F | 2-F, 4-$O(CH_2)_3CH_3$ | 1.5355 |
| 58 | O | F | F | 2-F, 4—(phenyl) | 1.5732 |
| 59 | O | F | F | 2-F, 4—(4-Cl-phenyl) | 1.5538 |
| 60 | O | F | F | 2-F, 4—(4-$CH_2CH_3$-phenyl) | 1.5852 |
| 61 | O | Cl | F | 2-F, 4—(4-$CH_2CH_3$-phenyl) | 1.5926 |
| 62 | O | F | F | 2-F, 4—(4-$CH_2CH_2CH_3$-phenyl) | 1.5790 |

| | | | | | |
|---|---|---|---|---|---|
| 63 | O | F | F | 2-F, 4-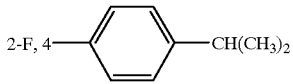—CH(CH₃)₂ | 1.5858 |
| 64 | O | F | F | 2-F, 4-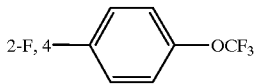—OCF₃ | 1.5650 |
| 65 | O | Cl | F | 2-F, 4-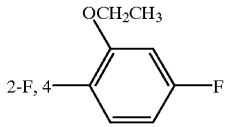—F (OCH₂CH₃) | 1.5617 |
| 66 | O | F | F | 2-F, 4-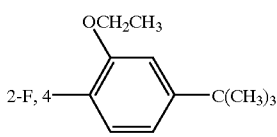—C(CH₃)₃ (OCH₂CH₃) | 1.5702 |
| 67 | O | F | F | 2-F, 5-F | 1.5436 |
| 68 | O | F | F | 2-F, 5-Cl | 1.5527 |
| 69 | O | F | F | 2-F, 6-F | 1.5542 |
| 70 | O | F | F | 3-F, 4-F | 1.5612 |
| 71 | O | F | F | 3-F, 4-Cl | 1.5637 |
| 72 | O | Cl | F | 3-F, 4-Cl | 1.5753 |
| 73 | O | F | F | 3-F, 4-(CH₂)₅CH₃ | 1.5218 |
| 74 | O | F | F | 3-F, 4-OCH₃ | 1.5538 |
| 75 | O | Cl | F | 3-F, 4-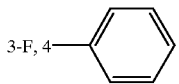 | 1.5846 |
| 76 | O | F | F | 3-F, 4-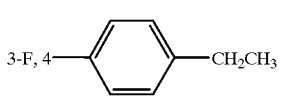—CH₂CH₃ | 1.5827 |
| 77 | O | F | F | 3-F, 5-F | 1.5381 |
| 78 | O | Cl | Cl | 3-F, 5-F | 1.5674 |
| 79 | O | H | F | 2-Cl | 1.5628 |
| 80 | O | F | F | 2-Cl | 1.5640 |
| 81 | O | Cl | F | 2-Cl | 1.5820 |
| 82 | O | F | F | 3-Cl | 1.5660 |
| 83 | O | Cl | F | 3-Cl | 1.5812 |
| 84 | O | H | Cl | 4-Cl | 1.5986 |
| 85 | O | F | F | 4-Cl | 1.5505 |
| 86 | O | Cl | F | 4-Cl | 1.5831 |
| 87 | O | Cl | Cl | 4-Cl | 1.5928 |
| 88 | O | F | F | 2-Cl, 3-Cl | 1.5764 |
| 89 | O | Cl | F | 2-Cl, 3-Cl | 101–102° C. |
| 90 | O | F | F | 2-Cl, 4-F | 1.6086 |
| 91 | O | H | Cl | 2-Cl, 4-Cl | 1.6076 |
| 92 | O | F | F | 2-Cl, 4-Cl | 109–112° C. |
| 93 | O | Cl | F | 2-Cl, 4-Cl | 1.5907 |
| 94 | O | F | F | 2-Cl, 4-CH₃ | 1.5680 |
| 95 | O | F | F | 2-Cl, 4-CH₂CH₃ | 1.5591 |
| 96 | O | F | F | 2-Cl, 4-CH₂CH₂CH₃ | 1.5568 |
| 97 | O | F | F | 2-Cl, 4-(CH₂)₃CH₃ | 1.5471 |
| 98 | O | F | F | 2-Cl, 4-CH₂CH(CH₃)₂ | 1.5506 |
| 99 | O | F | F | 2-Cl, 4-C(CH₃)₃ | 1.5537 |
| 100 | O | Cl | F | 2-Cl, 4-C(CH₃)₃ | 1.1648 |
| 101 | O | F | F | 2-Cl, 4-(CH₂)₄CH₃ | 1.5451 |
| 102 | O | F | F | 2-Cl, 4-(CH₂)₅CH₃ | 1.5444 |
| 103 | O | F | F | 2-Cl, 4-(CH₂)₆CH₃ | 1.5386 |
| 104 | O | F | F | 2-Cl, 4-(CH₂)₇CH₃ | 1.5377 |
| 105 | O | Cl | F | 2-Cl, 4-(CH₂)₇CH₃ | 1.5436 |
| 106 | O | F | F | 2-Cl, 4-(CH₂)₉CH₃ | 1.5214 |
| 107 | O | F | F | 2-Cl, 4-(CH₂)₁₁CH₃ | 1.5262 |

| | | | | | |
|---|---|---|---|---|---|
| 108 | O | F | F | 2-Cl, 4-OCH$_2$CH$_2$CH$_3$ | 1.5548 |
| 109 | O | Cl | F | 2-Cl, 4-OCH$_2$CH$_2$CH$_3$ | 1.5682 |
| 110 | O | F | F | 2-Cl, 4-O(CH$_2$)$_4$CH$_3$ | 1.5501 |
| 111 | O | F | F | 2-Cl, 4-O(CH$_2$)$_8$CH$_3$ | 1.5420 |
| 112 | O | F | F | 2-Cl, 4—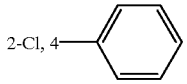 | 1.5764 |
| 113 | O | F | F | 2-Cl, 4—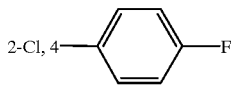—F | 1.6024 |
| 114 | O | F | F | 2-Cl, 4—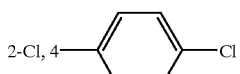—Cl | 1.6048 |
| 115 | O | F | F | 2-Cl, 4—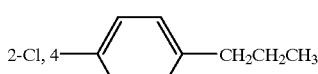—CH$_2$CH$_2$CH$_3$ | 1.5996 |
| 116 | O | Cl | F | 2-Cl, 4—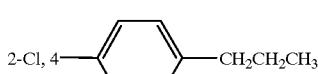—CH$_2$CH$_2$CH$_3$ | 1.6097 |
| 117 | O | F | F | 2-Cl, 4—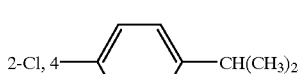—CH(CH$_3$)$_2$ | 1.6020 |
| 118 | O | F | F | 2-Cl, 4—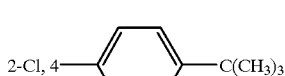—C(CH$_3$)$_3$ | 1.5930 |
| 119 | O | F | F | 2-Cl, 4—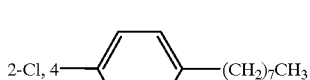—(CH$_2$)$_7$CH$_3$ | 1.5896 |
| 120 | O | F | F | 2-Cl, 4—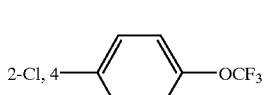—OCF$_3$ | 1.5682 |
| 121 | O | F | F | 2-Cl, 5-Cl | 1.5724 |
| 122 | O | F | F | 2-Cl, 5-CF$_3$ | 1.5254 |
| 123 | O | F | F | 3-Cl, 4-F | 1.5626 |
| 124 | O | Cl | F | 3-Cl, 4-F | 1.5719 |
| 125 | O | H | Cl | 3-Cl, 4-Cl | 1.6042 |
| 126 | O | F | F | 3-Cl, 4-Cl | 1.5648 |
| 127 | O | F | F | 3-Cl, 4-CH$_3$ | 1.5668 |
| 128 | O | F | F | 3-Cl, 4-CH$_2$CH$_2$CH$_3$ | 1.5625 |
| 129 | O | F | F | 3-Cl, 4-(CH$_2$)$_5$CH$_3$ | 1.5428 |
| 130 | O | F | F | 3-Cl, 4-OCH$_2$CH$_3$ | 1.5623 |
| 131 | O | F | F | 3-Cl, 4—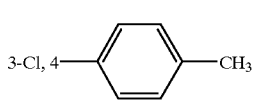—CH$_3$ | 1.5612 |
| 132 | O | F | F | 3-Cl, 4—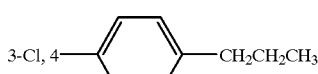—CH$_2$CH$_2$CH$_3$ | 1.5578 |

-continued

| No | X | R1 | R2 | Substituents | Value |
|---|---|---|---|---|---|
| 133 | O | Cl | F | 3-Cl, 4-(phenyl-CH₂CH₂CH₃) | 1.5695 |
| 134 | O | Cl | F | 3-Cl, 4-O-(phenyl-Cl) | 1.6102 |
| 135 | O | F | F | 3-Cl, 5-Cl | 1.5731 |
| 136 | O | H | F | 2-Br | 1.6063 |
| 137 | O | F | F | 4-Br | 1.5790 |
| 138 | O | Cl | F | 4-Br | 1.5894 |
| 139 | O | F | F | 2-$CH_3$ | 90–91° C. |
| 140 | S | F | F | 2-$CH_3$ | 127–128° C. |
| 141 | O | H | Cl | 3-$CH_3$ | 1.5864 |
| 142 | O | F | F | 3-$CH_3$ | 1.5559 |
| 143 | S | F | F | 3-$CH_3$ | 1.5916 |
| 144 | O | F | F | 4-$CH_3$ | 1.5548 |
| 145 | O | F | F | 2-$CH_3$, 4-F | 1.5538 |
| 146 | O | F | F | 2-$CH_3$, 4-Cl | 1.5652 |
| 147 | O | Cl | Cl | 2-$CH_3$, 4-Cl | 1.5851 |
| 148 | O | F | F | 2-$CH_3$, 4-$(CH_2)_7CH_3$ | 1.5352 |
| 149 | O | F | F | 2-$CH_3$, 4-$OCH_2CH_2CH_3$ | 1.5498 |
| 150 | O | Cl | F | 2-$CH_3$, 4-$OCH_2CH_2CH_3$ | 1.5584 |
| 151 | O | F | F | 2-$CH_3$, 4-(phenyl-Cl) | 1.5601 |
| 152 | O | F | F | 2-$CH_3$, 4-(phenyl-$CH_2CH_3$) | 1,5486 |
| 153 | O | F | F | 2-$CH_3$, 4-(phenyl-$C(CH_3)_3$) | 1.5923 |
| 154 | O | F | F | 2-$CH_3$, 4-(phenyl-$OCF_3$) | 1.5571 |
| 155 | O | Cl | F | 2-$CH_3$, 4-(phenyl-$OCF_3$) | 1.5589 |
| 156 | O | F | F | 2-$CH_3$, 4-O-(phenyl-Cl) | 1.5262 |
| 157 | O | F | F | 2-$CH_3$, 4-O-(phenyl-$(CH_2)_5CH_3$) | 1.5406 |
| 158 | O | F | F | 2-$CH_3$, 4-O-(phenyl-$CF_3$) | 1.5272 |
| 159 | O | Cl | F | 2-$CH_3$, 4-O-(phenyl-$OCF_3$) | 1.5164 |

-continued

| | | | | | |
|---|---|---|---|---|---|
| 160 | O | F | F | 2-CH₃, 5-CH₃ | 1.5624 |
| 161 | O | F | F | 2-CH₃, 5-CH(CH₃)₂ | 1.5473 |
| 162 | O | Cl | Cl | 2-CH₃, 5-C(CH₃)₃ | 119–121° C. |
| 163 | O | F | F | 3-CH₃, 4-CH₃ | 1.5626 |
| 164 | O | F | F | 3-CH₃, 4—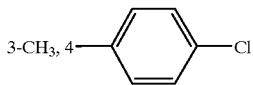—Cl | 1.5902 |
| 165 | O | Cl | F | 3-CH₃, 4-O—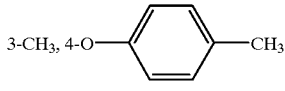—CH₃ | 1.5874 |
| 166 | O | F | F | 3-CH₃, 4-OCH₂—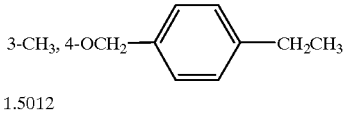—CH₂CH₃  1.5012 | |
| 167 | O | F | F | 2-CH₂CH₃ | 1.5508 |
| 168 | O | F | F | 3-CH₂CH₃ | 1.5499 |
| 169 | O | F | F | 4-CH₂CH₃ | 1.5512 |
| 170 | O | F | F | 2-CH₂CH₃, 4—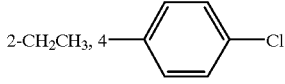—Cl | 1.5562 |
| 171 | O | F | F | 2-CH₂CH₃, 4—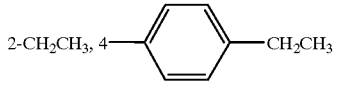—CH₂CH₃ | 1.5501 |
| 172 | O | F | F | 2-CH₂CH₃, 4—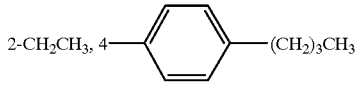—(CH₂)₃CH₃ | 1.5446 |
| 173 | O | F | F | 2-CH₂CH₃, 4—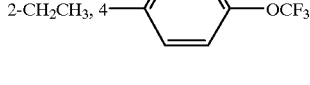—OCF₃ | 1.5602 |
| 174 | O | Cl | F | 2-CH₂CH₃, 4—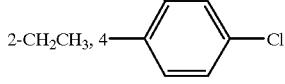 | 1.5602 |
| 175 | O | F | F | 2-CH₂CH₃, 4-O—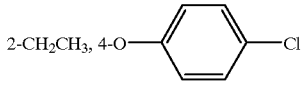—Cl | 1.5236 |
| 176 | O | F | F | 2-CH₂CH₃, 4-O—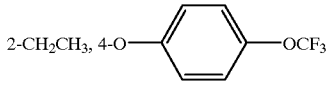—OCF₃ | 1.5161 |
| 177 | O | F | F | 2-CH₂CH₃, 5-Cl | 1.5502 |
| 178 | O | F | F | 2-CH₂CH₂CH₃ | 1.5432 |
| 179 | O | F | F | 3-CH₂CH₂CH₃ | 1.5438 |
| 180 | O | F | F | 4-CH₂CH₂CH₃ | 1.5446 |
| 181 | O | Cl | F | 4-CH₂CH₂CH₃ | 1.5621 |
| 182 | O | F | F | 2-CH₂CH₂CH₃, 4-Cl | 1.5648 |
| 183 | O | F | F | 3-CH(CH₃)₂ | 1.5452 |
| 184 | O | F | F | 4-CH(CH₃)₂ | 1.5467 |
| 185 | O | Cl | F | 4-CH(CH₃)₂ | 1.5614 |
| 186 | O | F | F | 3-(CH₂)₃CH₃ | 1.5417 |
| 187 | O | F | F | 4-(CH₂)₃CH₃ | 1.5420 |

-continued

| | | | | | |
|---|---|---|---|---|---|
| 188 | S | F | F | 4-(CH$_2$)$_3$CH$_3$ | 1.5729 |
| 189 | O | F | F | 3-CH$_2$CH(CH$_3$)$_2$ | 1.5706 |
| 190 | O | F | F | 4-CH$_2$CH(CH$_3$)$_2$ | 1.5456 |
| 191 | O | F | F | 4-CH(CH$_3$)CH$_2$CH$_2$ | 1.5976 |
| 192 | O | H | Cl | 3-C(CH$_3$)$_3$ | 1.5648 |
| 193 | O | F | F | 3-C(CH$_3$)$_3$ | 1.5352 |
| 194 | O | H | F | 4-C(CH$_3$)$_3$ | 1.5576 |
| 195 | O | Cl | F | 4-C(CH$_3$)$_3$ | 1.5530 |
| 196 | O | Cl | Cl | 4-C(CH$_3$)$_3$ | 1.5594 |
| 197 | S | F | F | 4-C(CH$_3$)$_3$ | 91.0–91.5° C. |
| 198 | O | F | F | 3-(CH$_2$)$_4$CH$_3$ | 1.5376 |
| 199 | O | F | F | 4-(CH$_2$)$_4$CH$_3$ | 1.5392 |
| 200 | O | F | F | 3-(CH$_2$)$_2$CH(CH$_3$)$_2$ | 1.5582 |
| 201 | O | F | F | 4-(CH$_2$)$_2$CH(CH$_3$)$_2$ | 1.5402 |
| 202 | O | F | F | 3-C(CH$_3$)$_2$CH$_2$CH$_3$ | 1.5628 |
| 203 | O | F | F | 4-C(CH$_3$)$_2$CH$_2$CH$_3$ | 1.5456 |
| 204 | O | F | F | 3-CH$_2$C(CH$_3$)$_3$ | 1.5580 |
| 205 | O | F | F | 4-CH$_2$C(CH$_3$)$_3$ | 1.5391 |
| 206 | S | F | F | 4-(CH$_2$)$_4$CH$_3$ | 1.5684 |
| 207 | S | F | F | 4-(CH$_2$)$_2$CH(CH$_3$)$_2$ | 1.5695 |
| 208 | O | F | F | 3-(CH$_2$)$_5$CH$_3$ | 1.5322 |
| 209 | O | Cl | F | 3-(CH$_2$)$_5$CH$_3$ | 1.5449 |
| 210 | O | F | F | 4-(CH$_2$)$_5$CH$_3$ | 1.5354 |
| 211 | O | F | F | 3-(CH$_2$)$_3$CH(CH$_3$)$_2$ | 1.5356 |
| 212 | O | F | F | 4-(CH$_2$)$_3$CH(CH$_3$)$_2$ | 1.5376 |
| 213 | O | F | F | 3-(CH$_2$)$_6$CH$_3$ | 1.5296 |
| 214 | O | Cl | F | 3-(CH$_2$)$_6$CH$_3$ | 1.5415 |
| 215 | O | F | F | 4-(CH$_2$)$_6$CH$_3$ | 1.5319 |
| 216 | O | F | F | 3-(CH$_2$)$_7$CH$_3$ | 1.5253 |
| 217 | O | F | F | 4-(CH$_2$)$_7$CH$_3$ | 1.5304 |
| 218 | S | F | F | 4-(CH$_2$)$_7$CH$_3$ | 127–128° C. |
| 219 | O | F | F | 3-(CH$_2$)$_8$CH$_3$ | 1.5281 |
| 220 | O | Cl | Cl | 3-(CH$_2$)$_8$CH$_3$ | 1.5525 |
| 221 | O | F | F | 4-(CH$_2$)$_8$CH$_3$ | 1.5267 |
| 222 | O | F | F | 3-(CH$_2$)$_9$CH$_3$ | 1.5280 |
| 223 | O | F | F | 4-(CH$_2$)9CH$_3$ | 1.5238 |
| 224 | O | F | F | 3-(CH$_2$)$_{10}$CH$_3$ | 1.5250 |
| 225 | O | F | F | 4-(CH$_2$)$_{11}$CH$_3$ | 1.5192 |
| 226 | O | F | F | 4-(CH$_2$)$_{14}$CH$_3$ | 51.5–52° C. |
| 227 | O | F | F | 3-OCH$_3$ | 1.5576 |
| 228 | O | Cl | F | 3-OCH$_3$ | 1.5729 |
| 229 | O | F | F | 4-OCH$_3$ | 78–79° C. |
| 230 | O | F | F | 2-OCH$_3$, 4-C(CH$_3$)$_3$ | 1.5468 |
| 231 | O | F | F | 2-OCH$_3$, 4-(CH$_2$)$_7$CH$_3$ | 1.5767 |
| 232 | O | F | F | 2-OCH$_3$, 4-(CH$_2$)$_8$CH$_3$ | 1.5340 |
| 233 | O | F | F | 2-OCH$_3$, 4-CF$_3$ | 74–75° C. |
| 234 | O | F | F | 2-OCH$_3$, 4-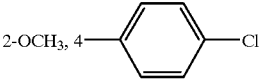-Cl | 1.5618 |
| 235 | O | F | F | 2-OCH$_3$, 4-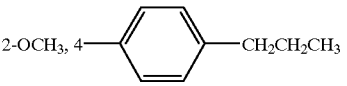-CH$_2$CH$_2$CH$_3$ | 1.5874 |
| 236 | O | Cl | F | 2-OCH$_3$, 4-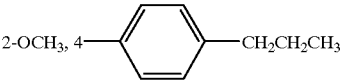-CH$_2$CH$_2$CH$_3$ | 1.5946 |
| 237 | O | F | F | 2-OCH$_3$, 4-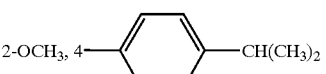-CH(CH$_3$)$_2$ | 1.5931 |
| 238 | O | F | F | 2-OCH$_3$, 4-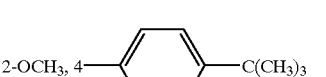-C(CH$_3$)$_3$ | 1.5918 |

-continued

| | | | | | |
|---|---|---|---|---|---|
| 239 | O | F | F | 2-OCH₃, 4-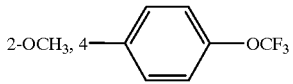 | 124–126° C. |
| 240 | O | F | F | 2-OCH₃, 5-Cl | 1.5600 |
| 241 | O | F | F | 2-OCH₃, 5-C(CH₃)₃ | 1.5468 |
| 242 | O | F | F | 2-OCH₃, 5-(CH₂)₆CH₃ | 1.5316 |
| 243 | O | F | F | 2-OCH₂CH₃ | 87–88° C. |
| 244 | O | Cl | F | 2-OCH₂CH₃ | 1.5647 |
| 245 | O | F | F | 3-OCH₂CH₃ | 1.5606 |
| 246 | O | F | F | 4-OCH₂CH₃ | 1.5574 |
| 247 | O | F | F | 2-OCH₂CH₃, 4-F | 1.5423 |
| 248 | O | H | Cl | 2-OCH₂CH₃, 4-Cl | 1.5961 |
| 249 | O | F | F | 2-OCH₂CH₃, 4-Cl | 1.5635 |
| 250 | O | F | F | 2-OCH₂CH₃, 4-CH₃, | 1.5497 |
| 251 | O | F | F | 2-OCH₂CH₃, 4-CH(CH₃)₂ | 1.5398 |
| 252 | O | F | F | 2-OCH₂CH₃, 4-C(CH₃)₃ | 134–135° C. |
| 253 | O | F | F | 2-OCH₂CH₃, 4-Si(CH₃)₃ | 1.5440 |
| 254 | O | Cl | F | 2-OCH₂CH₃, 4-Si(CH₃)₃ | 1.5542 |
| 255 | O | F | F | 2-OCH₂CH₃, 4-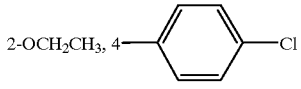 | 1.5564 |
| 256 | O | F | F | 2-OCH₂CH₃, 4-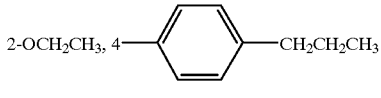 | 1.5818 |
| 257 | O | Cl | F | 2-OCH₂CH₃, 4-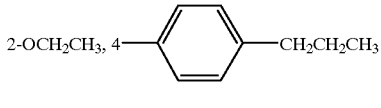 | 1.5929 |
| 258 | O | F | F | 2-OCH₂CH₃, 4-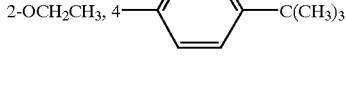 | 1.5681 |
| 259 | O | F | F | 2-OCH₂CH₃, 4-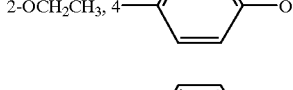 | 1.5435 |
| 260 | O | Cl | F | 2-OCH₂CH₃, 4-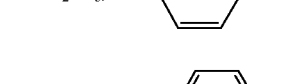 | 1.5659 |
| 261 | O | F | F | 2-OCH₂CH₃, 4-O-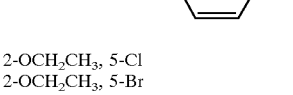 | 1.5542 |
| 262 | O | F | F | 2-OCH₂CH₃, 5-Cl | 1.5564 |
| 263 | O | F | F | 2-OCH₂CH₃, 5-Br | 1.5700 |
| 264 | O | F | F | 2-OCH₂CH₃, 5-C(CH₃)₃ | 1.5374 |
| 265 | O | F | F | 3-OCH₂CH₂CH₃ | 1.5535 |
| 266 | O | F | F | 4-OCH₂CH₂CH₃ | 1.5522 |
| 267 | O | F | F | 2-OCH₂CH₂CH₃, 4-F | 1.5392 |
| 268 | O | Cl | F | 2-OCH₂CH₂CH₃, 4-F | 1.5441 |
| 269 | O | F | F | 2-OCH₂CH₂CH₃, 4-Cl | 87–87.5° C. |
| 270 | O | F | F | 2-OCH₂CH₂CH₃, 4-CH₃ | 1.5451 |
| 271 | O | F | F | 2-OCH₂CH₂CH₃, 4-CH(CH₃)₂ | 1.5368 |
| 272 | O | F | F | 2-OCH₂CH₂CH₃, 5-(CH₂)₆CH₃ | 1.5328 |
| 273 | O | F | F | 3-OCH(CH₃)₂ | 1.5510 |
| 274 | O | F | F | 4-OCH(CH₃)₂ | 1.5535 |
| 275 | O | Cl | F | 4-OCH(CH₃)₂ | 1.5637 |
| 276 | O | F | F | 4-OCH₂CH(CH₃)₂ | 1.5452 |
| 277 | O | F | F | 4-OCH(CH₃)CH₂CH₃ | 1.5421 |

| | | | | -continued | |
|---|---|---|---|---|---|
| 278 | O | F | F | 3-O(CH$_2$)$_4$CH$_3$ | 1.5347 |
| 279 | O | F | F | 4-O(CH$_2$)$_4$CH$_3$ | 1.5344 |
| 280 | O | F | F | 4-O(CH$_2$)$_2$CH(CH$_3$)$_2$ | 1.5352 |
| 281 | O | F | F | 3-O(CH$_2$)$_5$CH$_3$ | 1.5331 |
| 282 | O | F | F | 4-O(CH$_2$)$_5$CH$_3$ | 1.5338 |
| 283 | O | Cl | F | 4-O(CH$_2$)$_5$CH$_3$ | 1.5388 |
| 284 | O | F | F | 3-O(CH$_2$)$_6$CH$_3$ | 1.5316 |
| 285 | O | F | F | 4-O(CH$_2$)$_6$CH$_3$ | 1.5311 |
| 286 | O | F | F | 3-O(CH$_2$)$_7$CH$_3$ | 1.5284 |
| 287 | O | F | F | 4-O(CH$_2$)$_7$CH$_3$ | 1.5281 |
| 288 | O | Cl | F | 4-O(CH$_2$)$_7$CH$_3$ | 1.5401 |
| 289 | O | F | F | 4-O(CH$_2$)$_8$CH$_3$ | 1.5264 |
| 290 | O | F | F | 4-O(CH$_2$)$_9$CH$_3$ | 1.5233 |
| 291 | O | F | F | 4-O(CH$_2$)$_{10}$CH$_3$ | 1.5254 |
| 292 | O | F | F | 4-O(CH$_2$)$_{11}$CH$_3$ | 50–51° C. |
| 293 | O | F | F | 3-O(CH$_2$)$_{14}$CH$_3$ | 1.5092 |
| 294 | O | F | F | 4-SCH$_3$ | 1.5893 |
| 295 | O | F | F | 4-SCH(CH$_3$)$_2$ | 1.5762 |
| 296 | O | F | F | 4-S(CH$_2$)$_8$CH$_3$ | 1.5508 |
| 297 | O | F | F | 2-CF$_3$ | 1.5144 |
| 298 | O | F | F | 3-CF$_3$ | 1.5136 |
| 299 | O | Cl | F | 3-CF$_3$ | 1.5286 |
| 300 | O | F | F | 4-CF$_3$ | 1.5290 |
| 301 | S | Cl | F | 4-CF$_3$ | 1.5631 |
| 302 | O | F | F | 3-OCF$_3$ | 1.5051 |
| 303 | O | F | F | 4-OCF$_3$ | 1.5087 |
| 304 | O | F | F | 3-OCH$_2$CF$_3$ | 1.5381 |
| 305 | O | Cl | F | 4-OCH$_2$CF$_3$ | 1.5476 |
| 306 | O | F | F | 3-Si(CH$_3$)$_3$ | 1.5396 |
| 307 | O | F | F | 4-Si(CH$_3$)$_3$ | 1.5441 |
| 308 | O | Cl | F | 4-Si(CH$_3$)$_3$ | 1.5552 |
| 309 | O | F | F | 4-Si(CH$_2$CH$_3$)$_3$ | 1.5440 |
| 310 | O | Cl | F | 4-Si(CH$_2$CH$_3$)$_3$ | 1.5493 |
| 311 | O | F | F | 4-Si[C(CH$_3$)$_3$, (CH$_3$)$_2$] | 1.5410 |
| 312 | O | F | F | 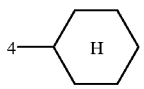 | 1.5592 |
| 313 | O | Cl | F | 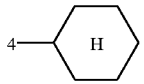 | 1.5651 |
| 314 | O | F | F | 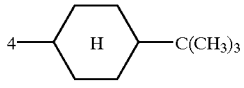 | 1.5421 |
| 315 | O | Cl | F | 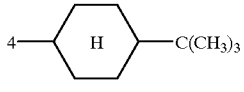 | 1.5516 |
| 316 | O | F | F | 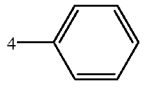 | 92–96° C. |
| 317 | O | F | F | 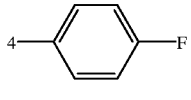 | 1.5954 |
| 318 | O | Cl | F | 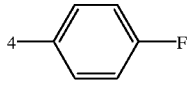 | 1.6052 |

-continued
| | | | | | |
|---|---|---|---|---|---|
| 319 | O | F | F | 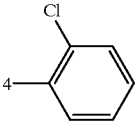 | 1.6116 |
| 320 | O | F | F | 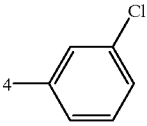 | 1.6187 |
| 321 | O | F | F | 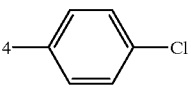 | 126–129° C. |
| 322 | O | F | F | 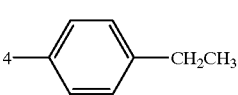 | 1.6126 |
| 323 | O | F | F | 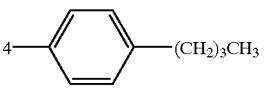 | 98–99° C. |
| 324 | O | F | F | 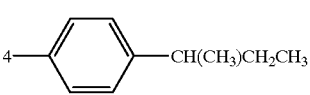 | 1.5942 |
| 325 | O | F | F | 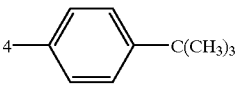 | 1.5476 |
| 326 | O | F | F | 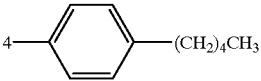 | 68–69° C. |
| 327 | O | F | F | 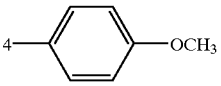 | 124–125° C. |
| 328 | O | F | F | 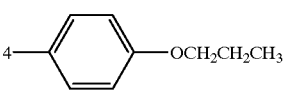 | 1.5962 |
| 329 | O | F | F | 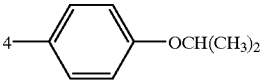 | 1.5755 |
| 330 | O | F | F | 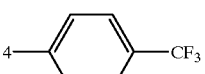 | 108–113° C. |
| 331 | O | F | Cl | 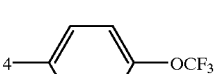 | 1.5804 |

-continued
| | | | | | |
|---|---|---|---|---|---|
| 332 | O | F | F | 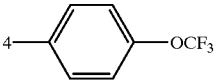 4—⟨⟩—OCF₃ | 105–106° C. |
| 333 | O | F | F | 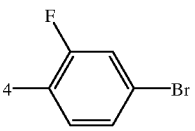 4—⟨F⟩—Br | 101–103° C. |
| 334 | O | Cl | F | 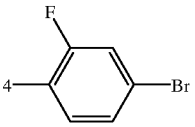 4—⟨F⟩—Br | 1.6113 |
| 335 | O | F | F | 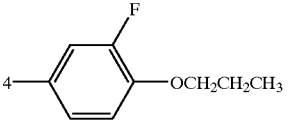 4—⟨F⟩—OCH₂CH₂CH₃ | 1.5922 |
| 336 | O | F | F | 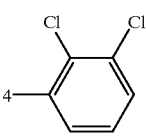 4—⟨Cl,Cl⟩ | 1.6154 |
| 337 | O | H | Cl | 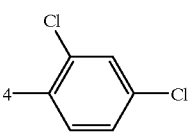 4—⟨Cl⟩—Cl | 1.6461 |
| 338 | O | F | F | 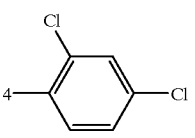 4—⟨Cl⟩—Cl | 117–119° C. |
| 339 | O | F | F | 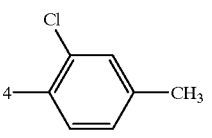 4—⟨Cl⟩—CH₃ | 1.6082 |
| 340 | O | F | F | 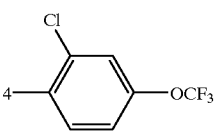 4—⟨Cl⟩—OCF₃ | 1.5695 |
| 341 | O | F | F | 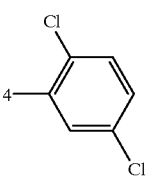 4—⟨Cl⟩—Cl | 1.6114 |

-continued
| | | | | | |
|---|---|---|---|---|---|
| 342 | O | F | F | 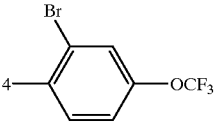 | 1.5856 |
| 343 | O | F | F | 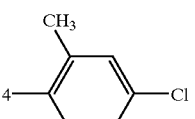 | 1.6071 |
| 344 | O | F | F | 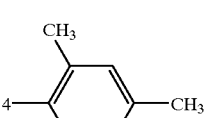 | 1.5961 |
| 345 | O | F | F | 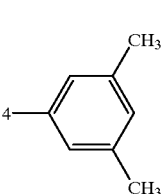 | 1.6068 |
| 346 | O | F | F | 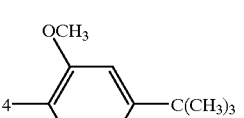 | 1.5830 |
| 347 | O | F | F | 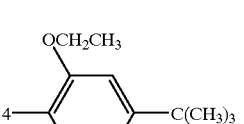 | 1.5804 |
| 348 | O | F | F | 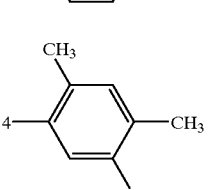 | 1.5946 |
| 349 | O | F | F | 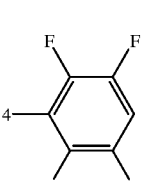 | 1.5631 |
| 350 | O | Cl | F | 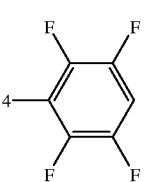 | 1.5718 |
| 351 | O | Cl | F | 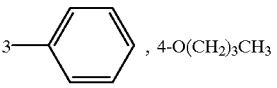, 4-O(CH$_2$)$_3$CH$_3$ | 1.5963 |

-continued
| | | | | | |
|---|---|---|---|---|---|
| 352 | O | F | F | 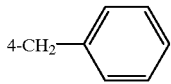 4-CH$_2$—C$_6$H$_5$ | 1.5894 |
| 353 | O | F | F | 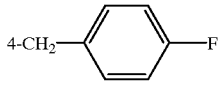 4-CH$_2$—C$_6$H$_4$—F | 1.5763 |
| 354 | O | Cl | F | 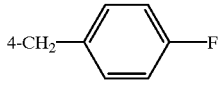 4-CH$_2$—C$_6$H$_4$—F | 1.5878 |
| 355 | O | F | F | 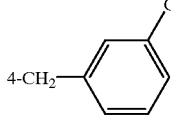 4-CH$_2$—(3-Cl-C$_6$H$_4$) | 1.5954 |
| 356 | O | F | F | 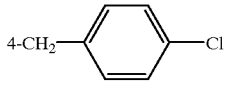 4-CH$_2$—C$_6$H$_4$—Cl | 1.5928 |
| 357 | O | F | F | 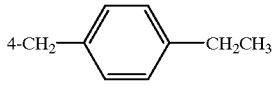 4-CH$_2$—C$_6$H$_4$—CH$_2$CH$_3$ | 1.5800 |
| 358 | O | F | F | 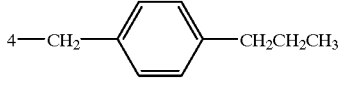 4—CH$_2$—C$_6$H$_4$—CH$_2$CH$_2$CH$_3$ | 1.5741 |
| 359 | O | F | F | 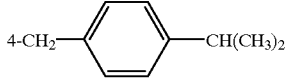 4-CH$_2$—C$_6$H$_4$—CH(CH$_3$)$_2$ | 1.5821 |
| 360 | O | F | F | 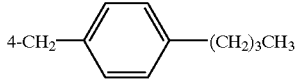 4-CH$_2$—C$_6$H$_4$—(CH$_2$)$_3$CH$_3$ | 1.5688 |
| 361 | O | Cl | F | 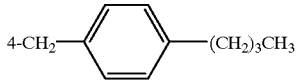 4-CH$_2$—C$_6$H$_4$—(CH$_2$)$_3$CH$_3$ | 1.5753 |
| 362 | O | F | F | 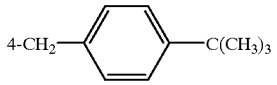 4-CH$_2$—C$_6$H$_4$—C(CH$_3$)$_3$ | 1.5738 |
| 363 | O | F | F | 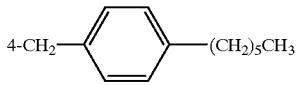 4-CH$_2$—C$_6$H$_4$—(CH$_2$)$_5$CH$_3$ | 1.5586 |
| 364 | O | F | F | 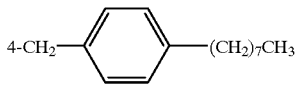 4-CH$_2$—C$_6$H$_4$—(CH$_2$)$_7$CH$_3$ | 1.5530 |
| 365 | O | F | F |  4-CH$_2$—C$_6$H$_4$—OCH$_3$ | 1.5846 |

-continued
| | | | | | |
|---|---|---|---|---|---|
| 366 | O | F | F | 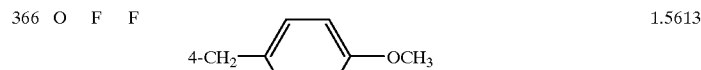 | 1.5613 |
| 367 | O | Cl | F | 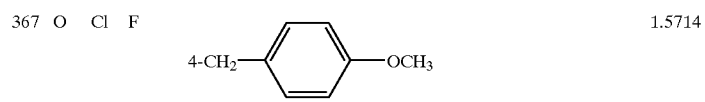 | 1.5714 |
| 368 | O | F | F | 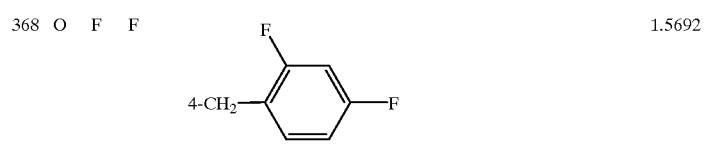 | 1.5692 |
| 369 | O | F | F | 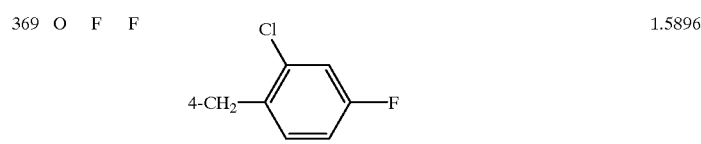 | 1.5896 |
| 370 | O | F | F | 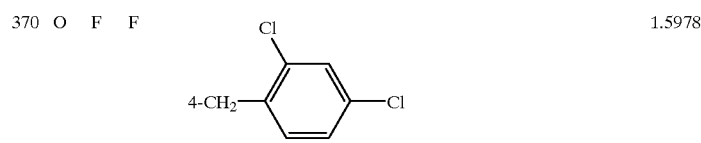 | 1.5978 |
| 371 | O | F | F | 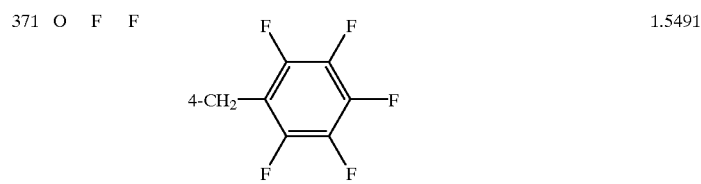 | 1.5491 |
| 372 | O | F | F | 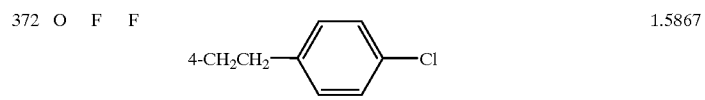 | 1.5867 |
| 373 | O | F | F | 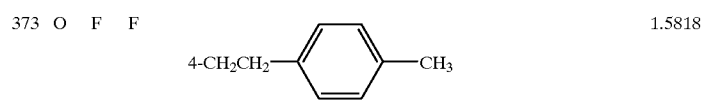 | 1.5818 |
| 374 | O | F | F | 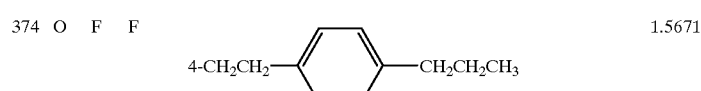 | 1.5671 |
| 375 | O | F | F | 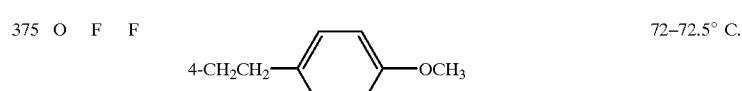 | 72–72.5° C. |
| 376 | O | F | F | 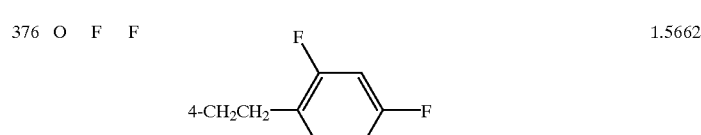 | 1.5662 |

-continued
| | | | | | |
|---|---|---|---|---|---|
| 377 | O | F | F | 4-CH₂CH₂— 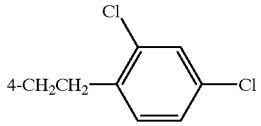 (2,4-dichlorophenyl) | 1.5904 |
| 378 | O | F | F | 4-CH₂CH₂CH₂— 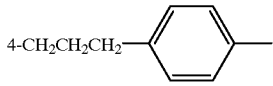 —F | 1.5654 |
| 379 | O | F | F | 4-CH₂CH₂CH₂— 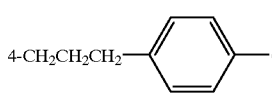 —Cl | 1.5813 |
| 380 | O | Cl | F | 4-CH₂CH₂CH₂— 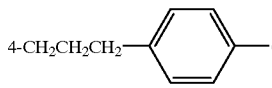 —Cl | 1.5911 |
| 381 | O | F | F | 4-OCH₂— 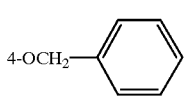 | 1.5791 |
| 382 | O | F | F | 4-OCH₂— 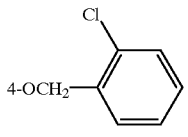 (2-chlorophenyl) | 1.5940 |
| 383 | O | F | F | 4-OCH₂— 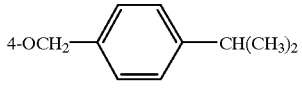 —CH(CH₃)₂ | 1.5746 |
| 384 | O | F | F | 4-OCH₂—  —C(CH₃)₃ | 1.5671 |
| 385 | O | F | F | 4-OCH₃— 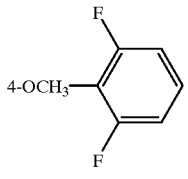 (2,6-difluorophenyl) | 1.5651 |
| 386 | O | F | F | 3-O— 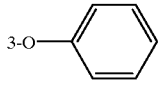 | 1.5847 |
| 387 | O | Cl | F | 3-O— 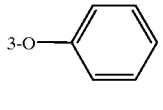 | 1.5984 |
| 388 | S | F | F | 3-O— 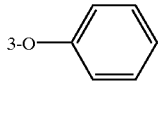 | 1.6150 |
| 389 | O | F | F | 4-O— 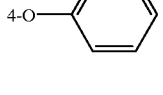 | 1.5920 |

-continued
| | | | | | |
|---|---|---|---|---|---|
| 390 | O | F | F | 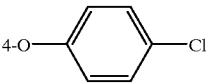 4-O—⟨⟩—Cl | 77–78° C. |
| 391 | O | F | F | 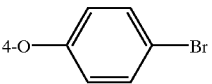 4-O—⟨⟩—Br | 83–85° C. |
| 392 | S | Cl | F | 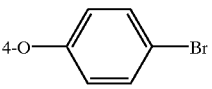 4-O—⟨⟩—Br | 1.6341 |
| 393 | O | F | F | 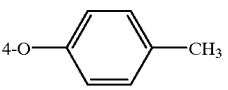 4-O—⟨⟩—CH₃ | 1.5864 |
| 394 | O | F | F | 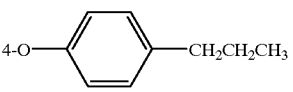 4-O—⟨⟩—CH₂CH₂CH₃ | 1.5758 |
| 395 | O | F | F | 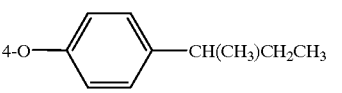 4-O—⟨⟩—CH(CH₃)CH₂CH₃ | 1.5713 |
| 396 | O | F | F | 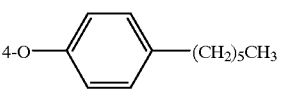 4-O—⟨⟩—(CH₂)₅CH₃ | 1.5617 |
| 397 | O | F | F | 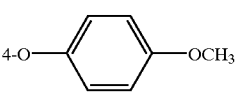 4-O—⟨⟩—OCH₃ | 1.5887 |
| 398 | O | F | F | 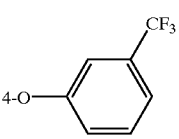 4-O—⟨⟩—CF₃ | 1.5504 |
| 399 | O | Cl | F | 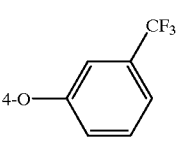 4-O—⟨⟩—CF₃ | 1.5688 |
| 400 | O | F | F | 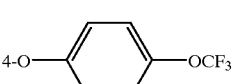 4-O—⟨⟩—OCF₃ | 1.5419 |
| 401 | O | Cl | F | 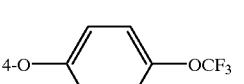 4-O—⟨⟩—OCF₃ | 1.5538 |
| 402 | O | F | F | 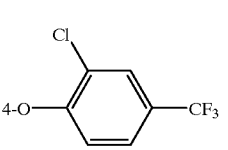 4-O—⟨⟩(Cl)—CF₃ | 1.5842 |

-continued
| | | | | | |
|---|---|---|---|---|---|
| 403 | O | Cl | F | 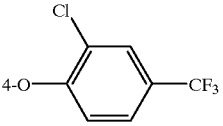 | 1.5914 |
| 404 | O | F | F | 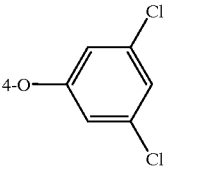 | 1.6017 |
| 405 | O | F | F | 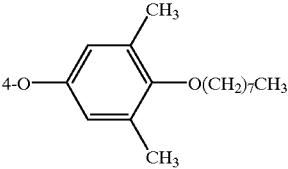 | 1.5502 |
| 406 | O | F | F | 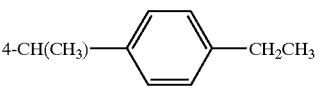 | 1.5712 |
| 407 | O | F | F | 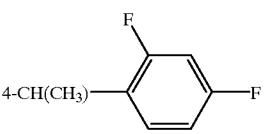 | 1.5654 |
| 408 | O | Cl | F | 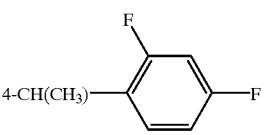 | 1.5750 |
| 409 | O | F | F | 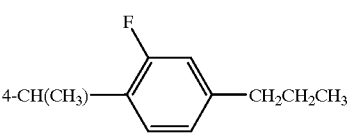 | 1.5694 |
| 410 | O | F | F | 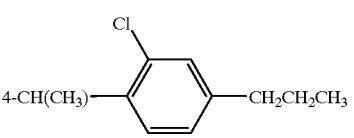 | 1.5797 |
| 411 | O | F | F | 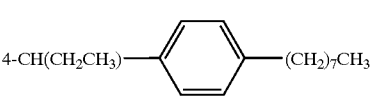 | 1.5428 |
| 412 | O | F | F | 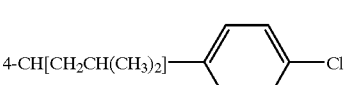 | 1.5773 |
| 413 | O | F | F | 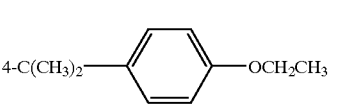 | 1.5698 |

-continued

| | | | | | |
|---|---|---|---|---|---|
| 414 | O | F | F | 4-CH(CH₃)CH₂—⌬—CH₂CH₃ | 1.5687 |
| 415 | O | F | F | 4-Si(CH₃)₂—⌬ | 1.6792 |
| 416 | O | Cl | F | 4-Si(CH₃)₂—⌬ | 1.5892 |
| 417 | O | F | F | 2-Cl, 3-Cl, 4-(CH₂)₄CH₃ | 1.5586 |
| 418 | O | Cl | F | 2-Cl, 4-CH₃, 5-Br | 1.5807 |
| 419 | O | F | F | 3-Cl, 4-OCH₂CH₃, 5-Cl | 1.5645 |
| 420 | O | Cl | Cl | 3-Cl, 4-OCH₂CH₃, 5-Cl | 1.5657 |
| 421 | O | Cl | F | 2-OCH₂CF₃, 4-Cl, 5-F | 1.5536 |
| 422 | O | F | F | 2-OCH₂CH₃, 4-Cl, 5-Br | 1.5676 |
| 423 | O | F | F | 2-OCH₂CH₂CH₃, 4-Cl, 5-Br | 1.5594 |
| 424 | O | F | F | 2-OCH₂CH₂CH₃, 4-Cl, 5-CH₂CH₃ | 1.5498 |
| 425 | O | Cl | F | 2-OCH₂CH₂CH₃, 4-Cl, 5-CH₂CH₃ | 1.5594 |
| 426 | O | Cl | F | 3-CH₂CH₃, 4-Cl, 5-CH₂CH₃ | 1.5546 |
| 427 | O | F | F | 2-OCH₃, 4-CH₃, 5-Cl | 106–109° C. |
| 428 | O | F | F | 2-OCH₂CH₃, 3-CH₃, 5-Cl | 1.5577 |
| 429 | O | F | F | 2-CH₃, 4-CH₃, 5-CH₃ | 1.5551 |
| 430 | O | F | F | 3-CH₃, 4-OCH(CH₃)₂, 5-CH₃ | 1.5418 |
| 431 | O | F | F | 3-CH₃, 4-O(CH₂)₂CH(CH₃)₂, 5-CH₃ | 1.5352 |
| 432 | O | Cl | F | 3-CH₃, 4-O(CH₂)₂CH(CH₃)₂, 5-CH₃ | 1.5382 |
| 433 | O | F | F | 2-OCH₃, 3-C(CH₃)₃, 5-CH₃ | 1.5461 |
| 434 | O | F | F | 2-CH₃, 3-CH₃, 4-CH₃, 5-CH₃ | 1.5648 |
| 435 | O | F | F | 2-OCH₃, 3-CH(CH₃)₂, 5-CH₂CH₃ | 1.5471 |
| 436 | O | Cl | F | 3-C(CH₃)₃, 4-OCH₃, 5-C(CH₃)₃ | 1.5320 |
| 437 | O | F | F | 2-F, 4-(CH₂)₆CH₃, 6-F | 1.5426 |
| 438 | O | F | F | 2-Cl, 3-F, 5-F | 1.5504 |
| 439 | O | Cl | F | 2-Cl, 3-F, 5-F | 1.5611 |
| 440 | O | H | F | 2-OCH₂CH₂CH₃, 4-F, 5-F | 1.5420 |
| 441 | O | F | F | 2-OCH₂CH₂CH₃, 4-F, 5-F | 1.5219 |
| 442 | O | Cl | F | 2-OCH₂CH₂CH₃, 4-F, 5-Br, 6-F | 1.5391 |
| 443 | O | F | F | 2-F, 3-F, 4-O(CH₂)₃CH₃, 5-F, 6-F | 1.5128 |
| 444 | O | F | F | 2-OCH₂CH₃, 3-C(CH₃)₃ | 1.5340 |
| 445 | O | F | F | 3-⌬ | 119–120° C. |
| 446 | O | Cl | F | 3-⌬ | 113–115° C. |
| 447 | O | F | F | 2-OCH₂CH₂CH₃, 3-Cl | 1.5472 |
| 448 | O | Cl | F | 2-OCH₂CH₂CH₃, 3-Cl | 1.5368 |

| Ex. No. | Compound | Physical Constant |
|---|---|---|
| 449 | 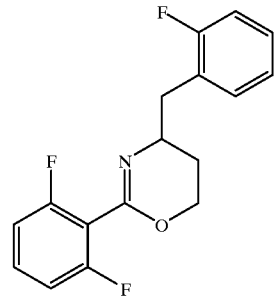 | δ[ppm]<br>H-4 3.85<br>H-5 1.75; 1.95<br>H-6 4.3<br>H-α 2.8; 3.2 |

-continued
| | | |
|---|---|---|
| 450 | 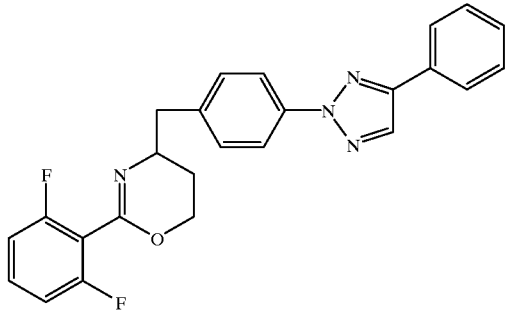 | δ[ppm]<br>H-4 3.85<br>H-5 1.75;<br>1.9<br>H-6 4.3<br>H-α 2.75;<br>3.25 |
| 451 | 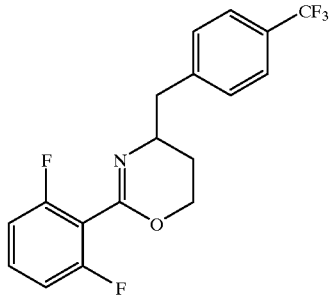 | δ[ppm]<br>H-4 3.8<br>H-5 1.75;<br>1.95<br>H-6 4.3<br>H-α 2.8;<br>3.2 |
| 452 | 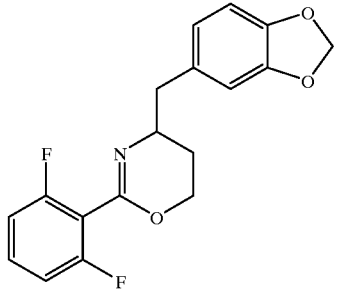 | δ[ppm]<br>H-4 3.7<br>H-5 1.75;<br>1.95<br>H-6 4.3<br>H-α 2.6;<br>3.15 |
| 453 | 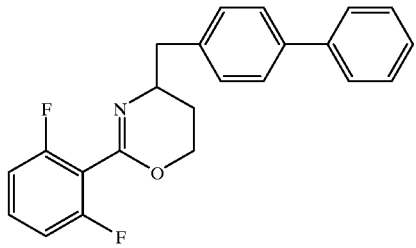 | δ[ppm]<br>H-4 3.7<br>H-5 1.75;<br>1.95<br>H-6 4.3<br>H-α 2.75;<br>3.25 |
| 454 | 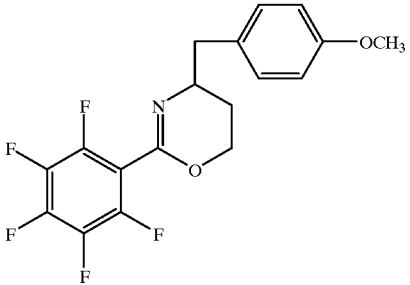 | δ[ppm]<br>H-4 3.7–3.8<br>H-5 1.7;<br>1.9<br>H-6 4.3<br>H-α 2.6;<br>3.2 |

-continued
| | | |
|---|---|---|
| 455 | 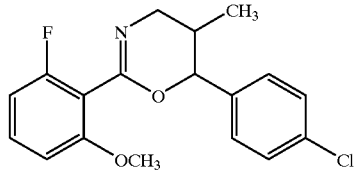 | log P 3.43 |
| 456 | 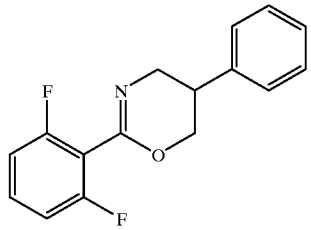 | m.p. 62° C. |
| 457 | 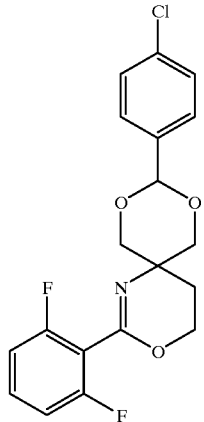 | m.p. 128° C. |
| 458 | 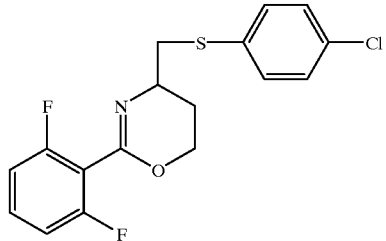 | log P 4.03 |
| 459 | 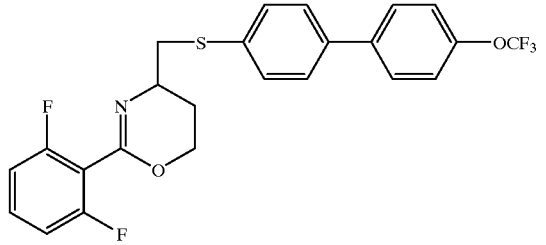 | log P 5.21 |

-continued
| | | |
|---|---|---|
| 460 | 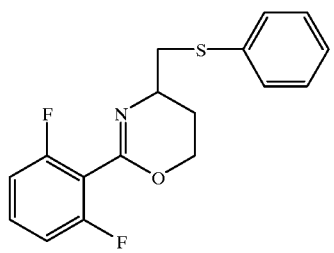 | log P 3.51 |
| 461 | 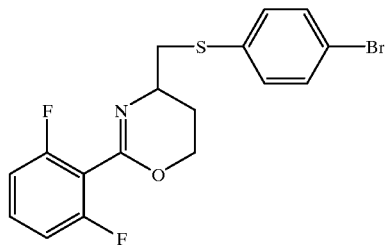 | log P 4.14 |
| 462 | 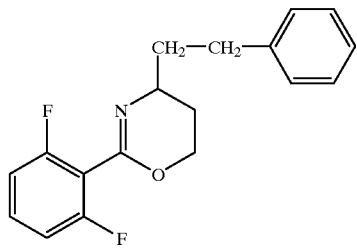 | MS**<br>M: 301<br>main peaks:<br>197; 141;<br>others:<br>210; 182; 169;<br>113; 105; 91 |
| 462 | 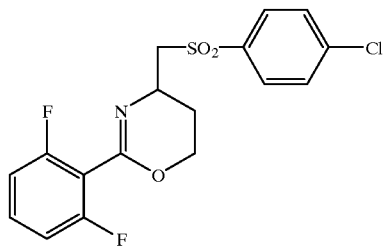 | MS<br>388 (1.3)<br>386 (3.7)<br>141 (100) |
| 464 | 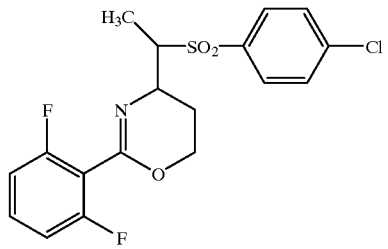 | MS 400 MH*<br>main peaks:<br>43, 113, 141, 224<br>others: 210, 284<br>372, 380 |
| 465 | 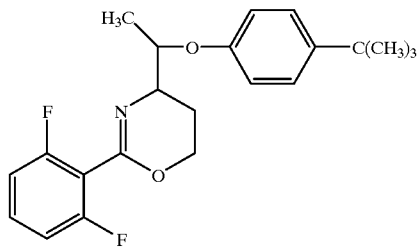 | lop P 4.91 |

-continued
| | | |
|---|---|---|
| 466 | 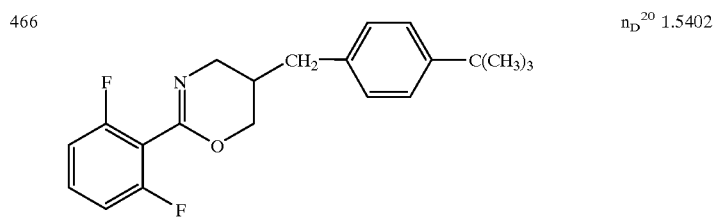 | $n_D^{20}$ 1.5402 |
| 467 | 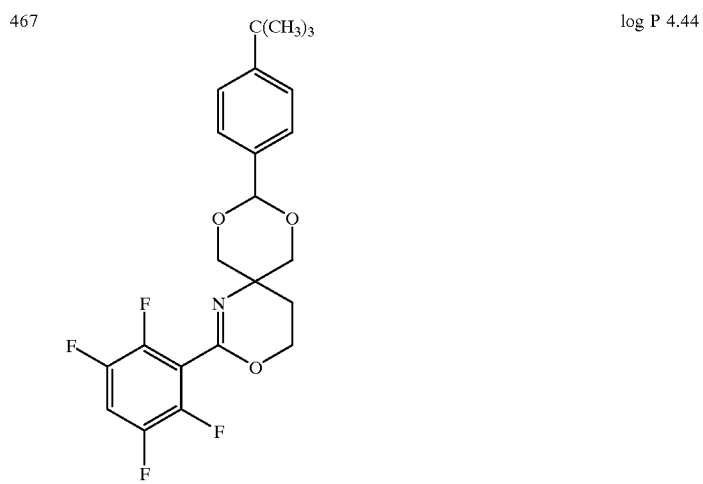 | log P 4.44 |
| 468 | 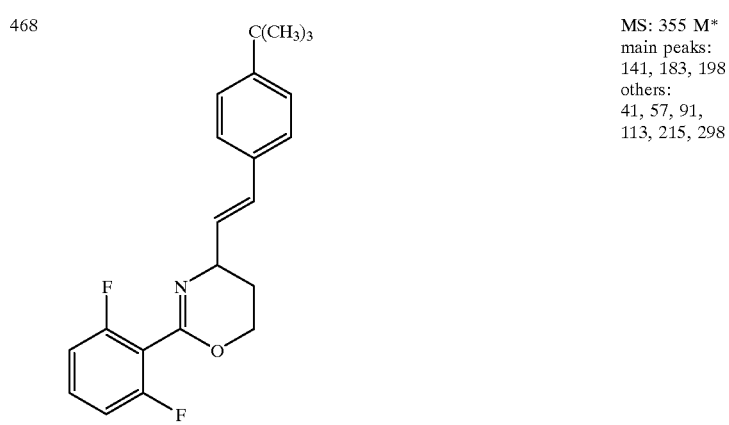 | MS: 355 M*<br>main peaks:<br>141, 183, 198<br>others:<br>41, 57, 91,<br>113, 215, 298 |
| 469 | 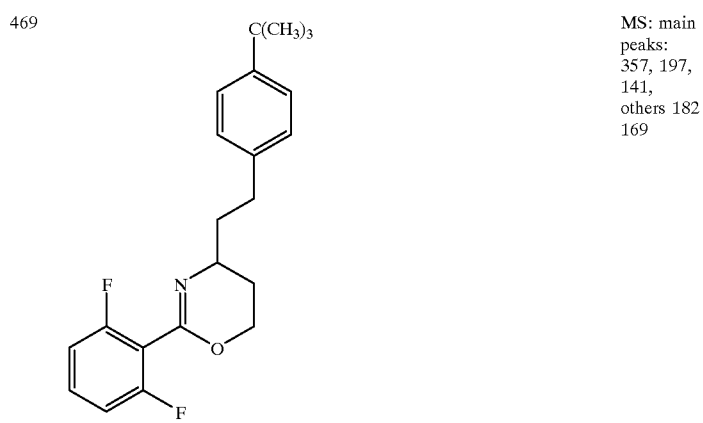 | MS: main<br>peaks:<br>357, 197,<br>141,<br>others 182<br>169 |

| | | | | -continued | |
|---|---|---|---|---|---|
| 470 | 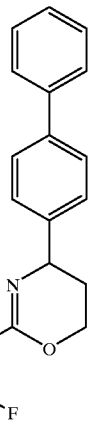 | | | | m.p. 96–98° C. |

*δ [ppm] = chemical shift in ppm; ¹H—NMR spectra measured in CDCl₃ with TMS (tetramethylsilane) as the standard, allocation of the protons in each case as in the formula of Example 25
**MS = Mass spectrum
***log P = negative common logarithm of the alkane/water partition coefficient determined by HPLC analysis with H₂O/CH₃CN as the mobile phase on 125 × 4.0 mm Kromasil 120 C 18 (5 μm); flow rate: 1.5 ml/minute compounds of formula

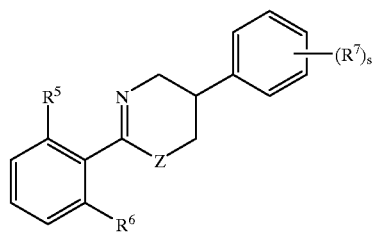

| Ex.No. | Z | R⁵ | R⁶ | (R⁷)ₛ | $n_{20}^D$ or m-p. |
|---|---|---|---|---|---|
| 471 | O | H | F | H | |
| 472 | O | H | Cl | H | |
| 473 | O | F | F | H | 67–69 |
| 474 | O | Cl | F | H | |
| 475 | O | Cl | Cl | H | |
| 476 | S | H | F | H | |
| 477 | S | H | Cl | H | |
| 478 | O | H | Cl | 2-F | |
| 479 | O | F | F | 2-F | 1.5180 |
| 480 | O | Cl | F | 2-F | 1.5336 |
| 481 | O | F | F | 3-F | 67–69 |
| 482 | O | Cl | F | 3-F | 60–64 |
| 483 | O | H | Cl | 4-F | |
| 484 | O | F | F | 4-F | 87–89 |
| 485 | O | Cl | F | 4-F | 113–115 |
| 486 | O | F | F | 2-F, 4-F | |
| 487 | O | Cl | F | 2-F, 4-F | |
| 488 | O | F | F | 2-F, 4-Cl | |
| 489 | O | F | F | 2-F, 4-(CH₂)₄CH₃ | |
| 490 | O | F | F | 2-F, 4-(CH₂)₅CH₃ | |
| 491 | O | F | F | 2-F, 4-(CH₂)₆CH₃ | |
| 492 | O | F | F | 2-F, 4-(CH₂)₇CH₃ | |
| 493 | O | Cl | F | 2-F, 4-(CH₂)₇CH₃ | |
| 494 | O | Cl | F | 2-F, 4-OCH₂CH₃ | |
| 495 | O | F | F | 2-F, 4-O(CH₂)₃CH₃ | |

-continued
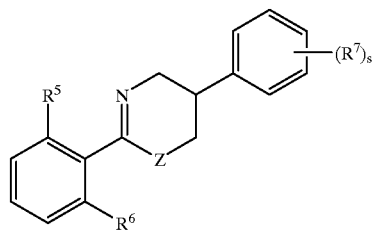
| Ex.No. | Z | R⁵ | R⁶ | (R⁷)ₛ | $n_{20}^D$ or m-p. |
|---|---|---|---|---|---|
| 496 | O | F | F | 2-F, 4-(phenyl) | |
| 497 | O | F | F | 2-F, 4-(4-Cl-phenyl) | |
| 498 | O | F | F | 2-F, 4-(4-CH₂CH₃-phenyl) | |
| 499 | O | Cl | F | 2-F, 4-(4-CH₂CH₃-phenyl) | |
| 500 | O | F | F | 2-F, 4-(4-CH₂CH₂CH₃-phenyl) | |
| 501 | O | F | F | 2-F, 4-(4-CH(CH₃)₂-phenyl) | |
| 502 | O | F | F | 2-F, 4-(4-OCF₃-phenyl) | |
| 503 | O | Cl | F | 2-F, 4-(3-OCH₂CH₃-4-F-phenyl) | |
| 504 | O | F | F | 2-F, 4-(3-OCH₂CH₃-4-C(CH₃)₃-phenyl) | |
| 505 | O | F | F | 2-F, 5-F | |
| 506 | O | F | F | 2-F, 5-Cl | |
| 507 | O | F | F | 2-F, 6-F | 131–133 |
| 508 | O | F | F | 3-F, 4-F | |
| 509 | O | F | F | 3-F, 4-Cl | |
| 510 | O | Cl | F | 3-F, 4-Cl | |
| 511 | O | F | F | 3-F, 4-(CH₂)₅CH₃ | |
| 512 | O | F | F | 3-F, 4-OCH₃ | |

-continued

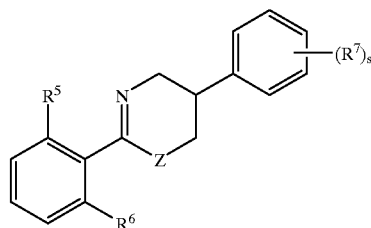

| Ex.No. | Z | R⁵ | R⁶ | (R⁷)ₛ | n₂₀ᴰ or m-p. |
|---|---|---|---|---|---|
| 513 | O | F | F | 3-F, 4-[phenyl] | 173–175 |
| 514 | O | Cl | F | 3-F, 4-[phenyl] | |
| 515 | O | F | F | 3-F, 4-[phenyl]-CH₂CH₃ | |
| 516 | O | F | F | 3-F, 5-F | |
| 517 | O | Cl | Cl | 8-F, 5-F | |
| 518 | O | H | F | 2-Cl | |
| 519 | O | F | F | 2-Cl | 1.5522 |
| 520 | O | Cl | F | 2-Cl | 79–81 |
| 521 | O | F | F | 3-Cl | 1.5685 |
| 522 | O | Cl | F | 3-Cl | 1.5716 |
| 523 | O | H | Cl | 4-Cl | 87–89 |
| 524 | O | H | F | 4-Cl | 95–96 |
| 525 | O | F | F | 4-Cl | 95–97 |
| 526 | O | Cl | F | 4-Cl | 124–128 |
| 527 | O | Cl | Cl | 4-Cl | |
| 528 | O | F | F | 2-Cl, 3-Cl | 127–128 |
| 529 | O | Cl | F | 2-Cl, 3-Cl | |
| 530 | O | F | F | 2-Cl, 4-F | |
| 531 | O | H | Cl | 2-Cl, 4-Cl | |
| 532 | O | F | F | 2-Cl, 4-Cl | 98–100 |
| 533 | O | Cl | F | 2-Cl, 4-Cl | |
| 534 | O | F | F | 2-Cl, 4-CH₃ | |
| 535 | O | F | F | 2-Cl, 4-CH₂CH₃ | |
| 536 | O | F | F | 2-Cl, 4-CH₂CH₂CH₃ | |
| 537 | O | F | F | 2-Cl, 4-(CH₂)₃CH₃ | |
| 538 | O | F | F | 2-Cl, 4-CH₂CH(CH₃)₂ | |
| 539 | O | F | F | 2-Cl, 4-C(CH₃)₃ | |
| 540 | O | Cl | F | 2-Cl, 4-C(CH₃)₃ | |
| 541 | O | F | F | 2-Cl, 4-(CH₂)₄CH₃ | |
| 542 | O | F | F | 2-Cl, 4-(CH₂)₅CH₃ | |
| 543 | O | F | F | 2-Cl, 4-(CH₂)₆CH₃ | |
| 544 | O | F | F | 2-Cl, 4-(CH₂)₇CH₃ | |
| 545 | O | Cl | F | 2-Cl, 4-(CH₂)₇CH₃ | |
| 546 | O | F | F | 2-Cl, 4-(CH₂)₉CH₃ | |
| 547 | O | F | F | 2-Cl, 4-(CH₂)₉CH₃ | |
| 548 | O | F | F | 2-Cl, 4-OCH₂CH₂CH₃ | |
| 549 | O | Cl | F | 2-Cl, 4-OCH₂CH₂CH₃ | |
| 550 | O | F | F | 2-Cl, 4-O(CH₂)₄CH₃ | |
| 551 | O | F | F | 2-Cl, 4-O(CH₂)₅CH₃ | |
| 552 | O | F | F | 2-Cl, 4-[phenyl] | |
| 553 | O | F | F | 2-Cl, 4-[phenyl]-F | |

-continued

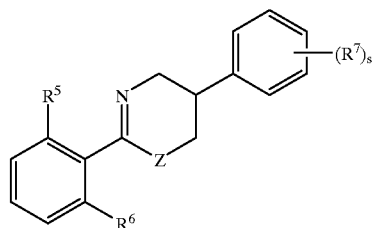

| Ex.No. | Z | R$^5$ | R$^6$ | (R$^7$)$_s$ | n$_{20}$$^D$ or m-p. |
|---|---|---|---|---|---|
| 554 | O | F | F | 2-Cl, 4-C$_6$H$_4$-Cl | |
| 555 | O | F | F | 2-Cl, 4-C$_6$H$_4$-CH$_2$CH$_2$CH$_3$ | |
| 556 | O | Cl | F | 2-Cl, 4-C$_6$H$_4$-CH$_2$CH$_2$CH$_3$ | |
| 557 | O | F | F | 2-Cl, 4-C$_6$H$_4$-CH(CH$_3$)$_2$ | |
| 558 | O | F | F | 2-Cl, 4-C$_6$H$_4$-C(CH$_3$)$_3$ | |
| 559 | O | F | F | 2-Cl, 4-C$_6$H$_4$-(CH$_2$)$_7$CH$_3$ | |
| 560 | O | F | F | 2-Cl, 4-C$_6$H$_4$-OCF$_3$ | |
| 561 | O | F | F | 2-Cl, 5-Cl | 104–105 |
| 562 | O | F | F | 2-Cl, 6-F | 107–110 |
| 563 | O | F | F | 2-Cl, 6-Cl | |
| 564 | O | F | F | 2-Cl, 5-CF$_3$ | |
| 565 | O | F | F | 3-Cl, 4-F | |
| 566 | O | Cl | F | 3-Cl, 4-F | |
| 567 | O | H | Cl | 3-Cl, 4-Cl | |
| 568 | O | F | F | 3-Cl, 4-Cl | 101–103 |
| 569 | O | F | F | 3-Cl, 4-CH$_3$ | |
| 570 | O | F | F | 3-Cl, 4-CH$_2$CH$_2$CH$_3$ | |
| 571 | O | F | F | 3-Cl, 4-(CH$_2$)$_5$CH$_3$ | |
| 572 | O | F | F | 3-Cl, 4-OCH$_2$CH$_3$ | |
| 573 | O | F | F | 3-Cl, 4-C$_6$H$_5$ | 142–143 |
| 574 | O | F | F | 3-Cl, 4-C$_6$H$_4$-CH$_3$ | |

-continued

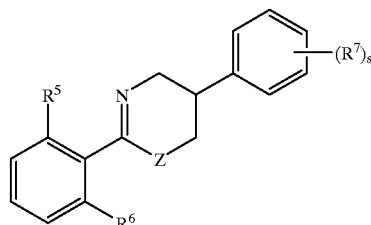

| Ex.No. | Z | R⁵ | R⁶ | (R⁷)ₛ | $n_{20}^D$ or m-p. |
|---|---|---|---|---|---|
| 575 | O | F | F | 3-Cl, 4-(C₆H₄)-CH₂CH₂CH₃ | |
| 576 | O | Cl | F | 3-Cl, 4-(C₆H₄)-CH₂CH₂CH₃ | |
| 577 | O | Cl | F | 3-Cl, 4-O-(C₆H₄)-Cl | |
| 578 | O | F | F | 3-Cl, 5-Cl | 114-14 117 |
| 579 | O | H | F | 2-Br | |
| 580 | O | F | F | 4-Br | |
| 581 | O | Cl | F | 4-Br | |
| 582 | O | F | F | 2-CH₃ | 115–117 |
| 583 | O | Cl | F | 2-CH₃ | 106–108 |
| 584 | S | F | F | 2-CH₃ | |
| 585 | O | H | Cl | 3-CH₃ | |
| 586 | O | F | F | 3-CH₃ | 1.5530 |
| 587 | O | Cl | F | 3-CH₃ | 1.5660 |
| 588 | S | F | F | 3-CH₃ | |
| 589 | O | F | F | 4-CH₃ | 115–118 |
| 590 | O | Cl | O | 4-CH₃ | 124–128 |
| 591 | O | F | F | 2-CH₃, 4-F | |
| 592 | O | F | F | 2-CH₃, 5-CH(CH₃)₂ | |
| 593 | O | Cl | Cl | 2-CH₃, 5-C(CH₃)₃ | |
| 594 | O | F | F | 3-CH₃, 4-CH₃ | |
| 595 | O | F | F | 3-CH₃, 4-(C₆H₄)-Cl | |
| 596 | O | Cl | F | 3-CH₃, 4-O-(C₆H₄)-CH₃ | |
| 597 | O | F | F | 3-CH₃, 4-OCH₂-(C₆H₄)-CH₂CH₃ | |
| 598 | O | F | F | 2-CH₂CH₃ | 1.5537 |
| 598A | O | F | F | 3-CH₂CH₃ | 1.5481 |
| 599 | O | Cl | F | 3-CH₂CH₃ | 1.5623 |
| 600 | O | F | F | 4-CH₂CH₃ | 83–84 |
| 601 | O | F | F | 2-CH₂CH₉, 4-(C₆H₄)-Cl | |

-continued

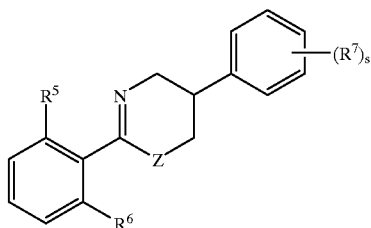

| Ex.No. | Z | R⁵ | R⁶ | (R⁷)ₛ | $n_{20}^D$ or m-p. |
|---|---|---|---|---|---|
| 602 | O | F | F | 2-CH₂CH₉, 4-(C₆H₄)-CH₂CH₃ | |
| 603 | O | F | F | 2-CH₂CH₃, 4-(C₆H₄)-(CH₂)₃CH₃ | |
| 604 | O | F | F | 2-CH₂CH₃, 4-(C₆H₄)-OCF₃ | |
| 605 | O | Cl | F | 2-CH₂CH₃, 4-(2-Cl,4-Cl-C₆H₃) | |
| 606 | O | F | F | 2-CH₂CH₃, 4-O-(C₆H₄)-Cl | |
| 607 | O | F | F | 2-CH₂CH₃, 4-O-(C₆H₄)-OCF₃ | |
| 608 | O | F | F | 2-CH₂CH₃, 5-Cl | |
| 609 | O | F | F | 3-CH₂CH₃, 4-(C₆H₅) | |
| 610 | O | F | F | 2-CH₂CH₂CH₃ | |
| 611 | O | F | F | 3-CH₂CH₂CH₃ | |
| 612 | O | F | F | 4-CH₂CH₂CH₃ | 81–86 |
| 613 | O | Cl | F | 4-CH₂CH₂CH₃ | |
| 614 | O | F | F | 2-CH₂CH₂CH₃, 4-Cl | |
| 615 | O | F | F | 3-CH(CH₃)₂ | 1.5447 |
| 616 | O | F | F | 4-CH(CH₃)₂ | |
| 617 | O | Cl | F | 4-CH(CH₃)₂ | |
| 618 | O | F | F | 3-(CH₂)₃CH₃ | |
| 619 | O | F | F | 4-(CH₂)₃CH₃ | |
| 620 | S | F | F | 4-(CH₂)₃CH₃ | |
| 621 | O | F | F | 3-CH₂CH(CH₃)₂ | |
| 622 | O | F | F | 4-CH₂CH(CH₃)₂ | |
| 623 | O | F | F | 4-CH(CH₃)CH₂CH₃ | |
| 624 | O | H | Cl | 3-C(CH₃)₃ | |
| 625 | O | F | F | 3-C(CH₃)₃ | |
| 626 | O | H | F | 4-C(CH₃)₃ | |
| 627 | O | F | F | 4-C(CH₃)₃ | 128–131 |
| 628 | O | Cl | Cl | 4-C(CH₃)₃ | |
| 629 | S | F | F | 4-C(CH₃)₃ | |
| 630 | O | F | F | 3-(CH₂)₄CH₃ | |
| 631 | O | F | F | 4-(CH₂)₄CH₃ | |

-continued

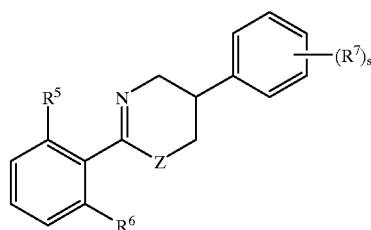

| Ex.No. | Z | R⁵ | R⁶ | (R⁷)ₛ | n₂₀ᴰ or m-p. |
|---|---|---|---|---|---|
| 632 | O | F | F | 3-(CH₂)₂CH(CH₃)₂ | |
| 633 | O | F | F | 4-(CH₂)₂CH(CH₃)₂ | |
| 634 | O | F | F | 3-C(CH₃)₂CH₂CH₃ | |
| 635 | O | F | F | 4-C(CH₃)₂CH₂CH₃ | |
| 636 | O | F | F | 3-CH₂C(CH₃)₃ | |
| 637 | O | F | F | 4-CH₂C(CH₃)₃ | |
| 638 | S | F | F | 4-(CH₂)₄CH₃ | |
| 639 | S | F | F | 4-(CH₂)₂CH(CH₃)₂ | |
| 640 | O | F | F | 3-(CH₂)₅CH₃ | |
| 641 | O | Cl | F | 3-(CH₂)₅CH₃ | |
| 642 | O | F | F | 4-(CH₂)₅CH₃ | |
| 643 | O | F | F | 3-(CH₂)₃CH(CH₃)₂ | |
| 644 | O | F | F | 4-(CH₂)₃CH(CH₃)₂ | |
| 645 | O | F | F | 3-(CH₂)₆CH₃ | |
| 646 | O | Cl | F | 3-(CH₂)₆CH₃ | |
| 647 | O | F | F | 4-(CH₂)₆CH₃ | 78–80 |
| 648 | O | F | F | 3-(CH₂)₇CH₃ | |
| 649 | O | F | F | 4-(CH₂)₇CH₃ | |
| 650 | S | F | F | 4-(CH₂)₇CH₃ | |
| 651 | O | F | F | 3-(CH₂)₈CH₃ | |
| 652 | O | Cl | Cl | 3-(CH₂)₆CH₃ | |
| 653 | O | F | F | 4-(CH₂)₈CH₃ | |
| 654 | O | F | F | 3-(CH₂)₉CH₃ | |
| 655 | O | F | F | 4-(CH₂)₉CH₃ | |
| 656 | O | F | F | 3-(CH₂)₁₀CH₃ | |
| 657 | O | F | F | 4-(CH₂)₁₁CH₃ | |
| 658 | O | F | F | 4-(CH₂)₁₄CH₃ | |
| 659 | O | F | F | 2-OCH₃ | 1.5512 |
| 660 | O | F | F | 3-OCH₃ | 87–88 |
| 661 | O | Cl | F | 3-OCH₃ | |
| 662 | O | F | F | 4-OCH₃ | 101–104 |
| 663 | O | Cl | F | 4-OCH₃ | 123–123 |
| 664 | O | F | F | 2-OCH₃, 4-Cl | 106–108 |
| 665 | O | Cl | F | 2-OCH₃, 4-Cl | 130–133 |
| 666 | O | F | F | 2-OCH₃, 4-C(CH₃)₃ | 119–122 |
| 667 | O | Cl | F | 2-OCH₃, 4-C(CH₃)₃ | 97–101 |
| 668 | O | F | F | 2-OCH₃, 4-(CH₂)₇CH₃ | |
| 669 | O | F | F | 2-OCH₃, 4-(CH₂)₈CH₃ | |
| 670 | O | F | F | 2-OCH₃, 4-CF₃ | |
| 671 | O | F | F | 2-OCH₃, 4-⟨C₆H₄⟩-Cl | |
| 672 | O | F | F | 2-OCH₃, 4-⟨C₆H₄⟩-CH₂CH₂CH₃ | |
| 673 | O | Cl | F | 2-OCH₃, 4-⟨C₆H₄⟩-CH₂CH₂CH₃ | |
| 674 | O | F | F | 2-OCH₃, 4-⟨C₆H₄⟩-CH(CH₃)₂ | |

-continued

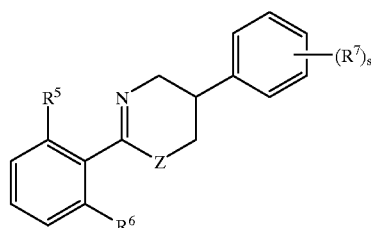

| Ex.No. | Z | R⁵ | R⁶ | (R⁷)ₛ | $n_{20}^D$ or m–p. |
|---|---|---|---|---|---|
| 675 | O | F | F | 2-OCH₃, 4-(C₆H₄)-C(CH₃)₃ | |
| 676 | O | F | F | 2-OCH₃, 4-(C₆H₄)-OCF₃ | |
| 677 | O | F | F | 2-OCH₃, 5-Cl | 68–70 |
| 678 | O | Cl | F | 2-OCH₃, 5-Cl | 1.5745 |
| 679 | O | F | F | 2-OCH₃, 5-C(CH₃)₃ | 124–126 |
| 680 | O | Cl | F | 2-OCH₃, 5-C(CH₃)₃ | 142–144 |
| 681 | O | F | F | 2-OCH₃, 5-(CH₂)₆CH₃ | |
| 682 | O | F | F | 2-OCH₂CH₃ | 58–60 |
| 683 | O | Cl | F | 2-OCH₂CH₃ | 1.5685 |
| 684 | O | F | F | 3-OCH₂CH₃ | 65–68 |
| 685 | O | F | F | 4-OCH₂CH₃ | 107–110 |
| 686 | O | F | F | 2-OCH₂CH₃, 4-F | |
| 687 | O | H | Cl | 2-OCH₂CH₃, 4-Cl | |
| 688 | O | F | F | 2-OCH₂CH₃, 4-Cl | 89–92 |
| 689 | O | Cl | F | 2-OCH₂CH₃, 4-Cl | 89–91 |
| 690 | O | F | F | 2-OCH₂CH₃, 4-CH₃ | |
| 691 | O | F | F | 2-OCH₂CH₃, 4-CH(CH₃)₂ | |
| 692 | O | F | F | 2-OCH₂CH₃, 4-C(CH₃)₃ | |
| 693 | O | Cl | F | 2-OCH₂CH₃, 4-C(CH₃)₃ | |
| 694 | O | F | F | 2-OCH₂CH₃, 4-Si(CH₃)₃ | |
| 695 | O | Cl | F | 2-OCH₂CH₃, 4-Si(CH₃)₃ | |
| 696 | O | F | F | 2-OCH₂CH₃, 4-(C₆H₄)-Cl | |
| 697 | O | F | F | 2-OCH₂CH₃, 4-(C₆H₄)-CH₂CH₂CH₃ | |
| 698 | O | Cl | F | 2-OCH₂CH₃, 4-(C₆H₄)-CH₂CH₂CH₃ | |
| 699 | O | F | F | 2-OCH₂CH₃, 4-(C₆H₄)-C(CH₃)₃ | |
| 700 | O | F | F | 2-OCH₂CH₃, 4-(C₆H₄)-OCF₃ | |
| 701 | O | Cl | F | 2-OCH₂CH₃, 4-(C₆H₄)-OCF₃ | |

-continued

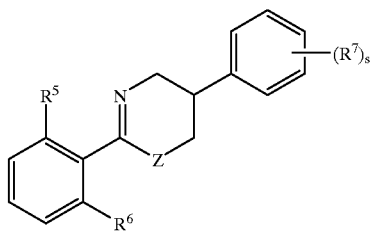

| Ex.No. | Z | $R^5$ | $R^6$ | $(R^7)_s$ | $n_{20}^D$ or m-p. |
|---|---|---|---|---|---|
| 702 | O | F | F | 2-OCH$_2$CH$_3$, 4-O-C$_6$H$_4$-OCF$_3$ | |
| 703 | O | F | F | 2-OCH$_2$CH$_3$, 5-Cl | 81–84 |
| 704 | O | Cl | F | 2-OCH$_2$CH$_3$, 5-Cl | 1.5686 |
| 705 | O | F | F | 2-OCH$_2$CH$_3$, 5-Br | |
| 706 | O | F | F | 2-OCH$_2$CH$_3$, 5-C(CH$_3$)$_3$ | 96–99 |
| 707 | O | F | F | 2-OCH$_2$CH$_2$CH$_3$ | 1.5465 |
| 708 | O | Cl | F | 2-OCH$_2$CH$_2$CH$_3$ | 1.5600 |
| 709 | O | F | F | 3-OCH$_2$CH$_2$CH$_3$ | 1.5496 |
| 710 | O | F | F | 4-OCH$_2$CH$_2$CH$_3$ | 89–92 |
| 711 | O | F | F | 2-OCH$_2$CH$_2$CH$_3$, 4-F | |
| 712 | O | Cl | F | 2-OCH$_2$CH$_2$CH$_3$, 4-F | |
| 713 | O | F | F | 2-OCH$_2$CH$_2$CH$_3$, 4-Cl | 79–81 |
| 714 | O | Cl | F | 2-OCH$_2$CH$_2$CH$_3$, 4-Cl | 1.5608 |
| 715 | O | F | F | 2-OCH$_2$CH$_2$CH$_3$, 4-CH$_3$ | |
| 716 | O | F | F | 2-OCH$_2$CH$_2$CH$_3$, 4-CH(CH$_3$)$_2$ | |
| 717 | O | F | F | 2-OCH$_2$CH$_2$CH$_3$, 5-Cl | 93–94 |
| 718 | O | Cl | F | 2-OCH$_2$CH$_2$CH$_3$, 5-Cl | 1.5655 |
| 719 | O | F | F | 2-OCH$_2$CH$_2$CH$_3$, 5-(CH$_2$)$_6$CH$_3$ | |
| 720 | O | F | F | 3-OCH(CH$_3$)$_2$ | |
| 721 | O | F | F | 4-OCH(CH$_3$)$_2$ | |
| 722 | O | Cl | F | 4-OCH(CH$_3$)$_2$ | |
| 723 | O | F | F | 4-OCH$_2$CH(CH$_3$)$_2$ | 102–105 |
| 724 | O | F | F | 4-OCH(CH$_3$)CH$_2$CH$_3$ | |
| 725 | O | F | F | 2-O(CH$_2$)$_4$CH$_3$ | 1.5346 |
| 726 | O | F | F | 3-O(CH$_2$)$_4$CH$_3$ | |
| 727 | O | F | F | 4-O(CH$_2$)$_4$CH$_3$ | 50–53 |
| 728 | O | F | F | 4-O(CH$_2$)$_2$CH(CH$_3$)$_2$ | |
| 729 | O | F | F | 3-O(CH$_2$)$_5$CH$_3$ | |
| 730 | O | F | F | 4-O(CH$_2$)$_5$CH$_3$ | |
| 731 | O | Cl | F | 4-O(CH$_2$)$_5$CH$_3$ | |
| 732 | O | F | F | 3-O(CH$_2$)$_6$CH$_3$ | |
| 733 | O | F | F | 4-O(CH$_2$)$_6$CH$_3$ | 46–48 |
| 734 | O | F | F | 3-O(CH$_2$)$_7$CH$_3$ | |
| 735 | O | F | F | 4-O(CH$_2$)$_7$CH$_3$ | |
| 736 | O | Cl | F | 4-O(CH$_2$)$_7$CH$_3$ | |
| 737 | O | F | F | 4-O(CH$_2$)$_8$CH$_3$ | |
| 738 | O | F | F | 4-O(CH$_2$)$_8$CH$_3$ | |
| 739 | O | F | F | 4-O(CH$_2$)$_{10}$CH$_3$ | |
| 740 | O | F | F | 4-O(CH$_2$)$_{11}$CH$_3$ | |
| 741 | O | F | F | 4-O(CH$_2$)$_{14}$CH$_3$ | |
| 742 | O | F | F | 4-SCH$_3$ | 124–125 |
| 743 | O | F | F | 4-SCH$_2$CH$_3$ | 70–73 |
| 744 | O | F | F | 4-SCH(CH$_3$)$_2$ | |
| 745 | O | F | F | 4-S(CH$_2$)$_8$CH$_3$ | |
| 746 | O | F | F | 2-CF$_3$ | |
| 747 | O | F | F | 3-CF$_3$ | 1.5180 |
| 748 | O | Cl | F | 3-CF$_3$ | |
| 749 | O | F | F | 4-CF$_3$ | |
| 750 | S | Cl | F | 4-CF$_3$ | |
| 751 | O | F | F | 3-OCF$_3$ | |
| 752 | O | F | F | 4-OCF$_3$ | 124–127 |
| 753 | O | F | F | 4-OCH$_2$CF$_3$ | |
| 754 | O | Cl | F | 4-OCH$_2$CF$_3$ | |
| 755 | O | F | F | 3-Si(CH$_3$)$_3$ | |
| 756 | O | F | F | 4-Si(CH$_3$)$_3$ | |
| 757 | O | Cl | F | 4-Si(CH$_3$)$_3$ | |
| 758 | O | F | F | 4-Si(CH$_2$CH$_3$)$_3$ | |
| 759 | O | Cl | F | 4-Si(CH$_2$CH$_3$)$_3$ | |
| 760 | O | F | F | 4-Si(C(CH$_3$)$_3$, (CH$_3$)$_2$) | |

-continued
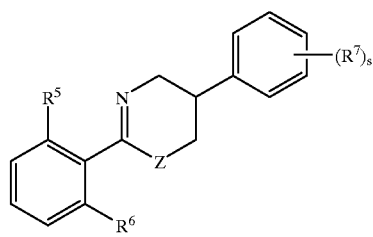
| Ex.No. | Z | R⁵ | R⁶ | (R⁷)ₛ | $n_{20}^D$ or m-p. |
|---|---|---|---|---|---|
| 761 | O | F | F | 4-cyclohexyl (H) | |
| 762 | O | Cl | F | 4-cyclohexyl (H) | |
| 763 | O | F | F | 4-cyclohexyl(H)-C(CH₃)₃ | |
| 764 | O | Cl | F | 4-cyclohexyl(H)-C(CH₃)₃ | |
| 765 | O | F | F | 3-phenyl-4-OCF₃ | 179–181 |
| 766 | O | F | F | 4-phenyl | 144–146 |
| 767 | O | Cl | F | 4-phenyl | |
| 768 | O | F | F | 4-phenyl-4-F | 148–150 |
| 769 | O | Cl | F | 4-phenyl-4-F | 138–140 |
| 770 | O | F | F | 4-phenyl-2-Cl | |
| 771 | O | F | F | 4-phenyl-3-Cl | |

-continued
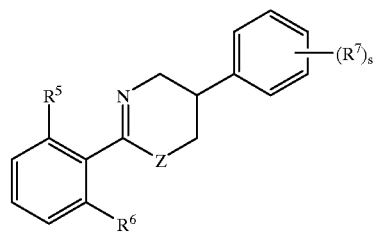
| Ex.No. | Z | R⁵ | R⁶ | (R⁷)ₛ | $n_{20}^D$ or m-p. |
|---|---|---|---|---|---|
| 772 | F | F | F | 4-C₆H₄-Cl | 143–145 |
| 773 | S | F | F | 4-C₆H₄-Cl | 155–158 |
| 774 | O | F | F | 4-C₆H₄-CH₂CH₃ | |
| 775 | O | F | F | 4-C₆H₄-(CH₂)₃CH₃ | |
| 776 | O | F | F | 4-C₆H₄-CH(CH₃)CH₂CH₃ | |
| 777 | O | F | F | 4-C₆H₄-C(CH₃)₃ | |
| 778 | O | F | F | 4-C₆H₄-(CH₂)₄CH₃ | |
| 779 | O | F | F | 4-C₆H₄-OCH₃ | |
| 780 | O | F | F | 4-C₆H₄-OCH₂CH₂CH₃ | |
| 781 | O | F | F | 4-C₆H₄-OCH(CH₃)₂ | |
| 782 | O | F | F | 4-C₆H₄-CF₃ | |

-continued
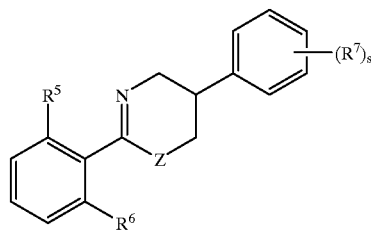
| Ex.No. | Z | R[5] | R[6] | (R[7])$_s$ | $n_{20}^D$ or m-p. |
|---|---|---|---|---|---|
| 783 | O | H | Cl | 4-C$_6$H$_4$-OCF$_3$ | |
| 784 | O | F | F | 4-C$_6$H$_4$-OCF$_3$ | 175–178 |
| 785 | O | F | F | 4-(2-F,4-Br-C$_6$H$_3$) | |
| 786 | O | F | F | 4-CH$_2$CH$_2$-(2,4-F$_2$-C$_6$H$_3$) | |
| 787 | O | F | F | 4-CH$_2$CH$_2$-(2,4-Cl$_2$-C$_6$H$_3$) | |
| 788 | O | F | F | 4-CH$_2$CH$_2$CH$_2$-(4-F-C$_6$H$_4$) | |
| 789 | O | F | F | 4-CH$_2$CH$_2$CH$_2$-(4-Cl-C$_6$H$_4$) | |
| 790 | O | Cl | F | 4-CH$_2$CH$_2$CH$_2$-(4-Cl-C$_6$H$_4$) | |
| 791 | O | F | F | 4-OCH$_2$-C$_6$H$_5$ | |
| 792 | O | F | F | 4-OCH$_2$-(2-Cl-C$_6$H$_4$) | |

-continued
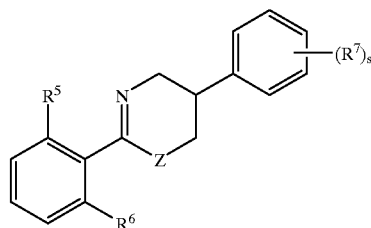
| Ex.No. | Z | $R^5$ | $R^6$ | $(R^7)_s$ | $n_{20}^D$ or m-p. |
|---|---|---|---|---|---|
| 793 | O | F | F | 4-OCH$_2$-C$_6$H$_4$-Cl | 149–152 |
| 794 | O | F | F | 4-OCH$_2$-C$_6$H$_4$-CH(CH$_3$)$_2$ | |
| 795 | O | F | F | 4-OCH$_2$-C$_6$H$_4$-C(CH$_3$)$_3$ | 133–136 |
| 796 | O | F | F | 4-OCH$_2$-(2,6-F$_2$-C$_6$H$_3$) | |
| 797 | O | F | F | 3-O-C$_6$H$_5$ | 1.5859 |
| 798 | O | Cl | F | 3-O-C$_6$H$_5$ | |
| 799 | S | F | F | 3-O-C$_6$H$_5$ | |
| 800 | O | F | F | 4-O-C$_6$H$_5$ | 129–132 |
| 801 | O | F | F | 4-O-C$_6$H$_4$-Cl | 146–148 |
| 802 | O | Cl | F | 4-O-C$_6$H$_4$-Cl | 112–113 |
| 803 | O | F | F | 4-O-C$_6$H$_4$-Br | |

-continued
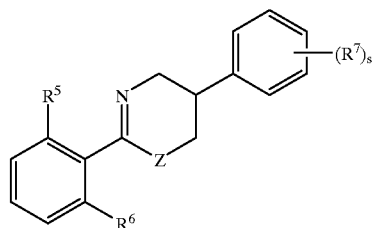
| Ex.No. | Z | R⁵ | R⁶ | (R⁷)ₛ | n₂₀ᴰ or m-p. |
|---|---|---|---|---|---|
| 804 | S | Cl | F | 4-O—⟨phenyl⟩—Br | |
| 805 | O | F | F | 4-O—⟨phenyl⟩—CH₃ | 128–129 |
| 806 | O | F | F | 4-O—⟨phenyl⟩—CH₂CH₂CH₃ | |
| 807 | O | F | F | 4-O—⟨phenyl⟩—CH(CH₃)CH₂CH₃ | |
| 808 | O | F | F | 4-O—⟨phenyl⟩—(CH₂)₅CH₃ | |
| 809 | O | F | F | 4-O—⟨phenyl⟩—OCH₃ | |
| 810 | O | F | F | 4-O—⟨phenyl (3-CF₃)⟩ | |
| 811 | O | Cl | F | 4-O—⟨phenyl (3-CF₃)⟩ | |
| 812 | O | F | F | 4-O—⟨phenyl⟩—CF₃ | 97–100 |
| 813 | O | F | F | 4-O—⟨phenyl⟩—OCF₃ | |
| 814 | O | Cl | F | 4-O—⟨phenyl⟩—OCF₃ | |

-continued
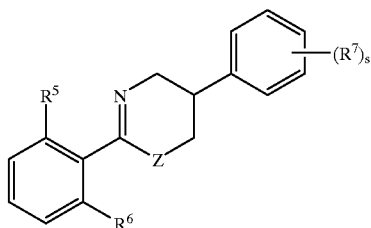
| Ex.No. | Z | R⁵ | R⁶ | (R⁷)ₛ | $n_{20}^D$ or m-p. |
|---|---|---|---|---|---|
| 815 | O | F | F | 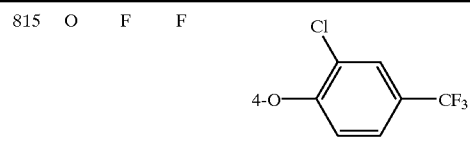 | |
| 816 | O | Cl | F | 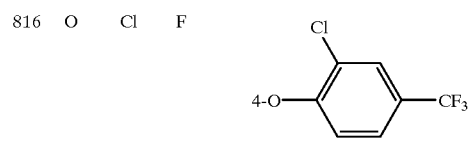 | |
| 817 | O | F | F | 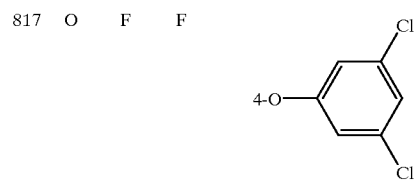 | |
| 818 | O | F | F | 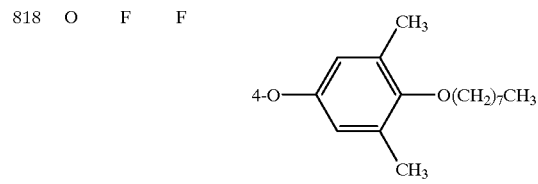 | |
compounds of formula
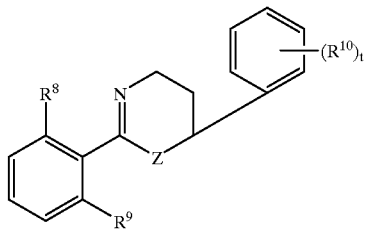
| Ex. No. | Z | R⁸ | R⁹ | (R¹⁰)ₜ | $n_{20}^D$ or m.p. |
|---|---|---|---|---|---|
| 819 | O | H | F | H | |
| 820 | O | H | Cl | H | |
| 821 | O | F | F | H | 1.5591 |
| 822 | O | Cl | F | H | 1.5783 |
| 823 | O | Cl | Cl | H | |
| 824 | S | H | F | H | |
| 825 | S | H | Cl | H | |
| 826 | O | H | Cl | 2-F | |

-continued

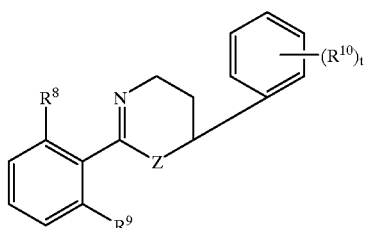

| Ex. No. | Z | R⁸ | R⁹ | (R¹⁰)ₜ | $n^D_{20}$ or m.p. |
|---|---|---|---|---|---|
| 827 | O | F  | F  | 2-F |  |
| 828 | O | Cl | F  | 2-F |  |
| 829 | O | F  | F  | 3-F |  |
| 830 | O | Cl | F  | 3-F |  |
| 831 | O | H  | Cl | 4-F |  |
| 832 | O | F  | F  | 4-F |  |
| 833 | O | Cl | F  | 4-F |  |
| 834 | O | F  | F  | 2-F,4-F |  |
| 835 | O | Cl | F  | 2-F,4-F |  |
| 836 | O | F  | F  | 2-F,4-Cl |  |
| 837 | O | F  | F  | 2-F,4-(CH₂)₄CH₃ |  |
| 838 | O | F  | F  | 2-F,4-(CH₂)₅CH₃ |  |
| 839 | O | F  | F  | 2-F,4-(CH₂)₆CH₃ |  |
| 840 | O | F  | F  | 2-F,4-(CH₂)₇CH₃ |  |
| 841 | O | Cl | F  | 2-F,4-(CH₂)₇CH₃ |  |
| 842 | O | Cl | F  | 2-F,4-OCH₂CH₃ |  |
| 843 | O | F  | F  | 2-F,4-O(CH₂)₃CH₃ |  |
| 844 | O | Cl | F  | 3-F,4-Cl |  |
| 845 | O | F  | F  | 3-F,4-(CH₂)₅CH₃ |  |
| 846 | O | F  | F  | 3-F,4-OCH₃ |  |
| 847 | O | F  | F  | 3-F, 4—C₆H₅ |  |
| 848 | O | Cl | F  | 3-F, 4—C₆H₅ |  |
| 849 | O | F  | F  | 3-F, 4—C₆H₄—CH₂CH₃ |  |
| 850 | O | F  | F  | 3-F,5-F |  |
| 851 | O | Cl | Cl | 3-F,5-F |  |
| 852 | O | H  | F  | 2-Cl |  |
| 853 | O | F  | F  | 2-Cl | 74.5–76.0 |
| 854 | O | Cl | F  | 2-Cl |  |
| 855 | O | F  | F  | 3-Cl | 1.5616 |
| 856 | O | Cl | F  | 3-Cl |  |
| 857 | O | H  | Cl | 4-Cl |  |
| 858 | O | H  | F  | 4-Cl |  |
| 859 | O | F  | F  | 4-Cl | 1.5702 |
| 860 | O | Cl | F  | 4-Cl | 1.5887 |
| 861 | O | Cl | Cl | 4-Cl |  |
| 862 | O | F  | F  | 2-Cl,3-Cl |  |
| 863 | O | Cl | F  | 2-Cl,3-Cl | — |
| 864 | O | F  | F  | 2-Cl,4-F |  |
| 865 | O | H  | Cl | 2-Cl,4-Cl |  |
| 866 | O | F  | F  | 2-Cl,4-Cl | 77.5–78.5 |
| 867 | O | Cl | F  | 2-Cl,4-Cl |  |
| 868 | O | F  | F  | 2-Cl,4-CH₃ |  |
| 869 | O | F  | F  | 2-Cl,4-CH₂CH₃ |  |
| 870 | O | F  | F  | 2-Cl,4-CH₂CH₂CH₃ |  |
| 871 | O | F  | F  | 2-Cl,4-(CH₂)₃CH₃ |  |
| 872 | O | F  | F  | 2-Cl,4-CH₂CH(CH₃)₂ |  |
| 873 | O | F  | F  | 2-Cl,4-C(CH₃)₃ |  |
| 874 | O | Cl | F  | 2-Cl,4-C(CH₃)₃ |  |
| 875 | O | F  | F  | 2-Cl,4-(CH₂)₄CH₃ |  |

-continued

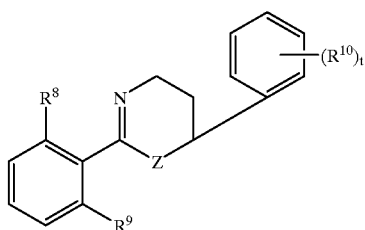

| Ex. No. | Z | R⁸ | R⁹ | (R¹⁰)_t | $n^D_{20}$ or m.p. |
|---|---|---|---|---|---|
| 876 | O | F | F | 2-Cl,4-(CH$_2$)$_5$CH$_3$ | |
| 877 | O | F | F | 2-Cl,4-(CH$_2$)$_6$CH$_3$ | |
| 878 | O | F | F | 2-Cl,4-(CH$_2$)$_7$CH$_3$ | |
| 879 | O | Cl | F | 2-Cl,4-(CH$_2$)$_7$CH$_3$ | |
| 880 | O | F | F | 2-Cl,4-(CH$_2$)$_9$CH$_3$ | |
| 881 | O | F | F | 2-Cl,4-(CH$_2$)$_{11}$CH$_3$ | |
| 882 | O | F | F | 2-Cl,4-OCH$_2$CH$_2$CH$_3$ | |
| 883 | O | Cl | F | 2-Cl,4-OCH$_2$CH$_2$CH$_3$ | |
| 884 | O | F | F | 2-Cl,4-O(CH$_2$)$_4$CH$_3$ | |
| 885 | O | F | F | 2-Cl,4-O(CH$_2$)$_8$CH$_3$ | |
| 886 | O | F | F | 2-Cl, 4—C$_6$H$_5$ | |
| 887 | O | F | F | 2-Cl, 4—(4-F-C$_6$H$_4$) | |
| 888 | O | F | F | 3-Cl,4-OCH$_2$CH$_5$ | |
| 889 | O | F | F | 3-Cl, 4—C$_6$H$_5$ | |
| 890 | O | F | F | 3-Cl, 4—(4-CH$_3$-C$_6$H$_4$) | |
| 891 | O | F | F | 3-Cl, 4—(4-CH$_2$CH$_2$CH$_3$-C$_6$H$_4$) | |
| 892 | O | Cl | F | 3-Cl, 4—(4-CH$_2$CH$_2$CH$_3$-C$_6$H$_4$) | |
| 893 | O | Cl | F | 3-Cl, 4-O—(4-Cl-C$_6$H$_4$) | |
| 894 | O | F | F | 3-Cl,5-Cl | |
| 895 | O | H | F | 2-Br | |
| 896 | O | F | F | 4-Br | |
| 897 | O | Cl | F | 4-Br | |
| 898 | O | F | F | 2-CH$_3$ | 1.5599 |
| 899 | O | Cl | F | 2-CH$_3$ | |
| 900 | S | F | F | 2-CH$_3$ | |
| 901 | O | H | Cl | 3-CH$_3$ | |
| 902 | O | F | F | 3-CH$_3$ | 1.5599 |
| 903 | O | Cl | F | 3-CH$_3$ | |
| 904 | S | F | F | 3-CH$_3$ | |
| 905 | O | F | F | 4-CH$_3$ | 1.5588 |

-continued

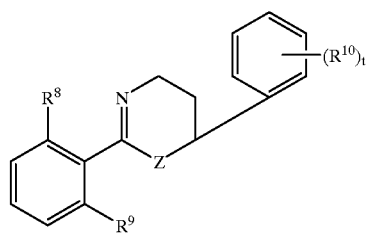

| Ex. No. | Z | $R^8$ | $R^9$ | $(R^{10})_t$ | $n^D_{20}$ or m.p. |
|---|---|---|---|---|---|
| 906 | O | Cl | F | 4-CH$_3$ | |
| 907 | O | F | F | 2-CH$_3$,4-F | |
| 908 | O | F | F | 2-CH$_3$,4-Cl | |
| 909 | O | Cl | Cl | 2-CH$_3$,4-Cl | |
| 910 | O | F | F | 2-CH$_3$,4-CH$_3$ | 1.5681 |
| 911 | O | F | F | 2-CH$_3$,4-(CH$_2$)$_7$CH$_3$ | |
| 912 | O | F | F | 2-CH$_3$,4-OCH$_2$CH$_2$CH$_3$ | |
| 913 | O | Cl | F | 2-CH$_3$,4-OCH$_2$CH$_2$CH$_3$ | |
| 914 | O | F | F | 2-CH$_3$, 4—C$_6$H$_4$—Cl | |
| 915 | O | F | F | 2-CH$_3$, 4—C$_6$H$_4$—CH$_2$CH$_3$ | |
| 916 | O | F | F | 2-CH$_3$, 4—C$_6$H$_4$—C(CH$_3$)$_3$ | |
| 917 | O | F | F | 2-CH$_3$, 4—C$_6$H$_4$—OCF$_3$ | |
| 918 | O | Cl | F | 2-CH$_3$, 4—C$_6$H$_4$—OCF$_3$ | |
| 919 | O | F | F | 2-CH$_3$, 4-O—C$_6$H$_4$—Cl | |
| 920 | O | F | F | 2-CH$_3$, 4-O—C$_6$H$_4$—(CH$_2$)$_5$CH$_3$ | |
| 921 | O | F | F | 2-CH$_3$, 4-O—C$_6$H$_4$—CF$_3$ | |
| 922 | O | Cl | F- | 2-CH$_3$, 4-O—C$_6$H$_4$—OCF$_3$ | |
| 923 | O | F | F | 2-CH$_3$,5-CH$_3$ | |
| 924 | O | F | F | 2-CH$_3$,5-CH(CH$_3$)$_2$ | |
| 925 | O | Cl | Cl | 2-CH$_3$,5-C(CH$_3$)$_3$ | |
| 926 | O | F | F | 3-CH$_3$,4-CH$_3$ | |

-continued
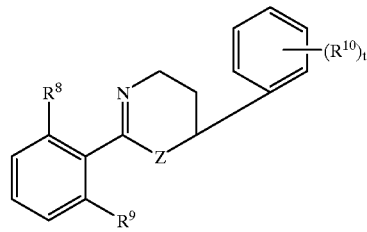
| Ex. No. | Z | R⁸ | R⁹ | (R¹⁰)ₜ | $n^D_{20}$ or m.p. |
|---|---|---|---|---|---|
| 927 | O | F | F | 3-CH₃, 4--Cl | |
| 928 | O | Cl | F | 3-CH₃, 4-O-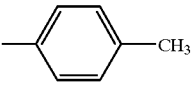-CH₃ | |
| 929 | O | F | F | 3-CH₃, 4-OCH₂-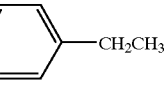-CH₂CH₃ | |
| 930 | O | F | F | 2-CH₂CH₃ | |
| 931 | O | F | F | 3-CH₂CH₃ | |
| 932 | O | Cl | F | 3-CH₂CH₃ | |
| 933 | O | F | F | 4-CH₂CH₃ | 1.5550 |
| 934 | O | F | F | 2-CH₂CH₃, 4--Cl | |
| 935 | O | F | F | 2-CH₂CH₃, 4-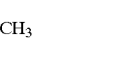-CH₂CH₃ | |
| 936 | O | F | F | 2-CH₂CH₃, 4-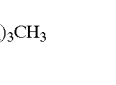-(CH₂)₃CH₃ | |
| 937 | O | F | F | 2-CH₂CH₃, 4--OCF₃ | |
| 938 | O | Cl | F | 2-CH₂CH₃, 4--Cl (2-Cl) | |
| 939 | O | F | F | 2-CH₂CH₃, 4-O--Cl | |
| 940 | O | F | F | 2-CH₂CH₃, 4-O--OCF₃ | |
| 941 | O | F | F | 2-CH₂CH₃, 5-Cl | |

-continued

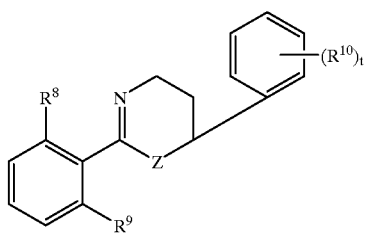

| Ex. No. | Z | R[8] | R[9] | (R[10])_t | $n^D_{20}$ or m.p. |
|---|---|---|---|---|---|
| 942 | O | F | F | 3-CH_2CH_3, 4-(phenyl) | |
| 943 | O | F | F | 2-CH_2CH_2CH_3 | |
| 944 | O | F | F | 3-CH_2CH_2CH_3 | |
| 945 | O | F | F | 4-CH_2CH_2CH_3 | |
| 946 | O | Cl | F | 4-CH_2CH_2CH_3 | |
| 947 | O | F | F | 2-CH_2CH_2CH_3,4-Cl | |
| 948 | O | F | F | 3-CH(CH_3)_2 | |
| 949 | O | F | F | 4-CH(CH_3)_2 | 1.5503 |
| 950 | O | Cl | F | 4-CH(CH_3)_2 | |
| 951 | O | F | F | 3-(CH_2)_3CH_3 | |
| 952 | O | F | F | 4-(CH_2)_3CH_3 | |
| 953 | S | F | F | 4-(CH_2)_3CH_3 | |
| 954 | O | F | F | 3-CH_2CH(CH_3)_2 | - |
| 955 | O | F | F | 4-CH_2CH(CH_3)_2 | |
| 956 | O | F | F | 4-CH(CH_3)CH_2CH_3 | |
| 957 | O | H | Cl | 3-C(CH_3)_3 | |
| 958 | O | F | F | 3-C(CH_3)_3 | |
| 959 | O | H | F | 4-C(CH_3)_3 | |
| 960 | O | F | F | 4-C(CH_3)_3 | 1.5475 |
| 961 | O | F | F | 2-OCH_3, 4-(4-CH(CH_3)_2-phenyl) | |
| 962 | O | F | F | 2-OCH_3, 4-(4-C(CH_3)_3-phenyl) | |
| 963 | O | F | F | 2-OCH_3, 4-(4-OCF_3-phenyl) | |
| 964 | O | F | F | 2-OCH_3,5-Cl | |
| 965 | O | Cl | F | 2-OCH_3,5-Cl | |
| 966 | O | F | F | 2-OCH_3,5-C(CH_3)_3 | |
| 967 | O | Cl | F | 2-OCH_3,5-C(CH_3)_3 | |
| 968 | O | F | F | 2-OCH_3,5-(CH_2)_6CH_3 | |
| 969 | O | F | F | 2-OCH_2CH_3 | |
| 970 | O | Cl | F | 2-OCH_2CH_3 | |
| 971 | O | F | F | 3-OCH_2CH_3 | |
| 972 | O | F | F | 4-OCH_2CH_3 | |
| 973 | O | F | F | 2-OCH_2CH_3,4-F | |
| 974 | O | H | Cl | 2-OCH_2CH_3,4-Cl | |
| 975 | O | F | F | 2-OCH_2CH_3,4-Cl | |
| 976 | O | Cl | F | 2-OCH_2CH_3,4-Cl | |
| 977 | O | F | F | 2-OCH_2CH_3,4-CH_3 | |
| 978 | O | F | F | 2-OCH_2CH_3,4-CH(CH_3) | |
| 979 | O | F | F | 2-OCH_2CH_3,4-C(CH_3)_3 | 111–112.5 |
| 980 | O | Cl | F | 2-OCH_2CH_3,4-C(CH_3)_3 | 130–133 |
| 981 | O | F | F | 2-OCH_2CH_3,4-Si(CH_3)_3 | |
| 982 | O | Cl | F | 2-OCH_2CH_3,4-Si(CH_3)_3 | |

-continued
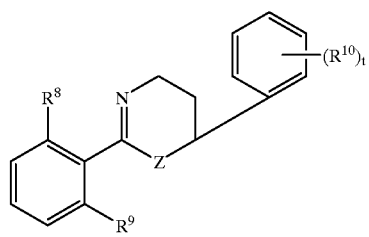
| Ex. No. | Z | R⁸ | R⁹ | (R¹⁰)_t | $n_D^{20}$ or m.p. |
|---|---|---|---|---|---|
| 983 | O | Cl | F | 4—cyclohexyl(H) | |
| 984 | O | F | F | 4—cyclohexyl(H)—C(CH₃)₃ | |
| 985 | O | Cl | F | 4—cyclohexyl(H)—C(CH₃)₃ | |
| 986 | O | F | F | 3—phenyl—OCF₃ | |
| 987 | O | F | F | 4—phenyl | 104–108 |
| 988 | O | Cl | F | 4—phenyl | 1.6283 |
| 989 | O | F | F | 4—phenyl—F | |
| 990 | O | Cl | F | 4—phenyl—F | |
| 991 | O | F | F | 4—phenyl(2-Cl) | |
| 992 | O | F | F | 4—phenyl(3-Cl) | |
| 993 | O | F | F | 4—phenyl—Cl | |

-continued

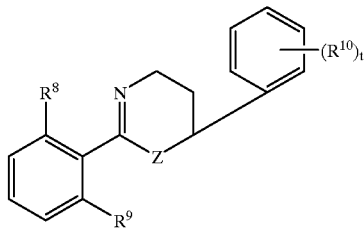

| Ex. No. | Z | R⁸ | R⁹ | (R¹⁰)ₜ | $n^D_{20}$ or m.p. |
|---|---|---|---|---|---|
| 994 | S | F | F | 4—⟨phenyl⟩—Cl | |

The preparation of individual examples mentioned in the Table is described below:

EXAMPLE 85

A mixture of 1.74 g (15.2 mmol) of methanesulfonyl chloride and 10 ml of tetrahydrofuran is added dropwise to a mixture of 4.5 g (13.8 mmol) of N-(2,6-difluorobenzoyl)-3-amino-3-(4-chlorophenyl)-1-propanol, 1.54 g (15.2 mmol) of triethylamine and 50 ml of tetrahydrofuran, while cooling with ice and stirring. The mixture is stirred at room temperature for 2 hours and filtered, and the filtrate is concentrated in vacuo. The residue is taken up in 50 ml of methanol, 2 g of potassium hydroxide are added and the mixture is stirred at 70° C. for 30 minutes. After customary working up, the crude product is purified by column chromatography on silica gel using the mobile phase n-hexane/ethyl acetate 8/2. 3.1 g (72.9%) of 2-(2,6-difluorophenyl)-4-(4-chlorophenyl)-5,6-dihydro-(4H)1,3-oxazine are obtained as a colorless oil.

$^1$H-NMR (60 MHz, CDCl$_3$, TMS) δ (ppm): 1.6~2.6 (2H, m), 4.2~4.4 (2H, m), 4.7 (1H, dd, J=5 Hz, J=8 Hz), 6.6~7.6 (7H, m); IR: 1674 cm$^{-1}$ (C=N)

EXAMPLE 197

A mixture of 5.0 g (14.4 mmol) of N-(2,6-difluorobenzoyl)-3-amino-3-(4-tert-butylphenyl)-1-propanol, 3.2 g (14.4 mmol) of phosphorus pentasulfide and 30 ml of toluene is heated under reflux for 6 hours. The mixture is allowed to cool, 10 ml of 20% strength aqueous sodium hydroxide solution are added and the mixture is heated under reflux for 30 minutes. After customary working up, the crude product is purified by column chromatography on silica gel (mobile phase n-hexane/ethyl acetate 8/2). 2.7 g (54.3%) of 2-(2,6-difluorophenyl)-4-(4-tert-butylphenyl)-5,6-dihydro-(4H)1,3-thiazine of melting point 91.0–91.5° C. are obtained.

$^1$H-NMR (60 MHz, CDCl$_3$, TMS) δ (ppm): 1.3 (9H, s); 1.4~2.5 (2H, m), 3.0~3.3 (2H, m), 4.8 (1H, dd, J=4 Hz, J=8 Hz), 6.6~7.5 (7H, m);

EXAMPLE 36

The procedure is as for Example 85, but 3.5 g (11.4 mmol) of N-(2-chloro-6-fluorobenzoyl)-3-amino-3-phenyl-1-propanol are employed instead of N-(2,6-difluorobenzoyl)-3-amino-3-(4-chlorophenyl)-1-propanol. 2.2 g (66.8%) of 2-(2-chloro-6-fluorophenyl)-4-phenyl-5,6-dihydro(4H)1,3-oxazine are obtained as a colorless oil.

$^1$H-NMR (60 MHz, CDCl$_3$, TMS) δ (ppm): 1.7~2.6 (2H, m), 4.2~4.5 (2H, m), 4.8 (1H, dd, J=5 Hz, J=8 Hz), 6.8~7.5 (8H, m); IR: 1680 cm$^{-1}$ (C=N)

EXAMPLE 298

The procedure is as for Example 85, but 4 g (11.1 mmol) of N-(2,6-difluorobenzoyl)-3-amino-3-(3-trifluoromethylphenyl)-1-propanol are employed instead of N-(2,6-difluorobenzoyl)-3-amino-3-(4-chlorophenyl)-1-propanol. 2.7 g (71.1%) of 2-(2,6-difluorophenyl)-4-(3-trifluoromethylphenyl)-5,6-dihydro(4H)1,3-oxazine are obtained as a colorless oil.

$^1$H-NMR (60 MHz, CDCl$_3$, TMS) δ (ppm): 1.7~2.6 (2H, m), 4.0~4.5 (2H, m), 4.8 (1H, dd, J=5 Hz, J=8 Hz), 6.6~7.7 (7H, m); IR: 1676 cm$^{-1}$ (C=N)

EXAMPLE 193

The procedure is as for Example 85, but 4.0 g (11.5 mmol) of N-(2,6-difluorobenzoyl)-3-amino-3-(3-tert-butylphenyl)-1-propanol are employed instead of N-(2,6-difluorobenzoyl)-3-amino-3-(4-chlorophenyl) 1-propanol. 2.6 g (68.6%) of 2-(2,6-difluorophenyl)-4-(3-tert-butylphenyl)-5,6-dihydro(4H)1,3- oxazine are obtained as a colorless oil.

$^1$H-NMR (60 MHz, CDCl$_3$, TMS) δ (ppm): 1.3 (9H, s); 1.7~2.4 (2H, m), 4.2~4.5 (2H, m), 4.8 (1H, dd, J=5 Hz, J=8 Hz), 6.8~7.5 (7H, m); IR: 1676 cm$^{-1}$ (C=N)

EXAMPLE 213

The procedure is as for Example 85, but 4.0 g (10.3 mmol) of N-(2,6-difluorobenzoyl)-3-amino-3- (3-n-heptylphenyl)-1-propanol are employed instead of N-(2,6-difluorobenzoyl)-3-amino-3-(4-chlorophenyl)-1-propanol. 2.7 g (70.8%) of 2-(2,6-difluorophenyl-4-(3-n-heptylphenyl)- 5,6-dihydro(4H)1,3-oxazine are obtained as a colorless oil.

$^1$H-NMR (60 MHz, CDCl$_3$, TMS) δ (ppm): 0.5~2.8 (17H, m), 4.1~4.4 (2H, m), 4.7 (1H, dd, J=5 Hz, J=7 Hz), 6.5~7.4 (7H, m); IR: 1676 cm$^{-1}$ (C=N)

EXAMPLE 154

The procedure is as for Example 85, but 5.0 g (10.8 mmol) of N-(2,6-difluorobenzoyl)-3-amino-3-(3-methyl-4'- trifluoromethoxybiphenyl-4-yl)-1-propanol are employed instead of N-(2,6-difluorobenzoyl)-3-amino-3-(4-chlorophenyl)-1-propanol. 3.1 g (64.5%) of 2-(2,6-difluorophenyl)-4-(3-methyl-4'-trifluoromethoxybiphenyl-4-yl)-5,6-dihydro(4H)1,3-oxazine are obtained as a colorless oil.

$^1$H-NMR (60 MHz, CDCl$_3$, TMS) δ (ppm): 1.6~2.6 (2H, m), 2.4 (3H, s); 4.2~4.4 (2H, m), 4.9 (1H, dd, J=5 Hz, J=8 Hz), 6.6~7.6 (10H, m); IR: 1678 cm$^{-1}$ (C=N)

Starting Substances of the Formula (II)

Example (II-1)

Stage 1:

Sodium (5.75 g, 0.25 mol) is added in portions to gently boiling diethyl carbonate (195 g; 1.65 mol) such that simmering is maintained. Thereafter, the bath temperature is increased to 140° C., p-t-butylacetophenone (44 g, 0.25 mol) is added dropwise in the course of 30 minutes, and at the same time the ethanol formed by reaction is distilled off over a bridge. The bath temperature is further increased to 160° C. and stirring of the batch is continued until the overhead temperature reaches 120° C. The mixture is cooled, poured onto 80 g of ice/20 ml of glacial acetic acid and extracted with diethyl ether.

After the crude product has been distilled, 32.5 g of ethyl 2-(p-t-butylbenzoyl)-acetate (52% of theory) of boiling point 126° C./0.6 mbar are obtained.

Stage 2:

Ethyl 2-(p-t-butylbenzoyl)-acetate (14.88 g, 0.06 mol) is added to a solution of O-methyl-hydroxylamine hydrochloride (5.01 g, 0.06 mol) in 60 ml of pyridine, and the mixture is stirred at 70° C. for 15 hours, cooled, poured onto 500 ml of water and extracted with methylene chloride.

14.9 g of ethyl 3-(p-t-butylphenyl)-3-methoximinopropionate (90% of theory) are obtained as a pale yellow oil.

Stage 3:

A solution of ethyl 3-(p-t-butylphenyl)-3-methoximinopropionate (14.9 g, 0.054 mol) in 50 ml of dimethoxyethane is added dropwise to a suspension of lithium aluminum hydride (6.16 g, 0.162 mol) in 100 ml of dimethoxyethane in the course of 30 minutes. The mixture is then boiled under reflux for 2 hours and cooled. 32.4 ml of a saturated aqueous sodium chloride solution are added at 0° C. The mixture is heated at 60° C. for 1 hour and filtered, the residue on the filter is extracted hot with toluene and the extract is filtered again. The filtrates are concentrated together.

9.9 g of 3-amino-3-(4-t-butylphenyl)-1-propanol (88% of theory) are obtained as a clear oil of adequate purity for further reaction (compare Example 1).

Example (II-2)

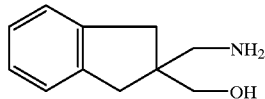

2.21 g of LiAlH$_4$ are initially introduced into 90 ml of dry dimethoxyethane, and 4 g of ethyl 2-cyano-indane-2-carboxylate [prepared by the method of A. Bayer and W. Perkin, Ber. Dtsch. Chem. Ges. 17 (1884) 122] are added at 0 to 5° C. The mixture is then heated under reflux for 2 hours. It is cooled to 0° C. and 11 ml of saturated sodium chloride solution are then carefully added dropwise. When the exothermic reaction has ended, the mixture is heated at 60° C. for one hour and then left to stand overnight. The following morning, the precipitate is filtered off with suction and washed twice with dimethoxyethane and the filtrate is evaporated. The oil which remains (3.24 g) is used further in the crude state.

Starting Substances of the Formula (IVa)

Example (IVa-1)

N-[3-Hydroxy-1-(4-t-butylphenyl)-propyl]-2,6-difluorobenzamide 2,6-Difluorobenzoyl chloride (2.65 g, 0.015 mol) is added in portions to a solution of 3-amino-3- (4-t-butylphenyl)-1-propanol (3.1 g, 0.015 mol) and triethylamine (3.03 g, 0.04 mol) in 30 ml of acetonitrile at room temperature (20° C.) in the course of 10 minutes. The reaction mixture is further stirred for 7 hours, water is added and the mixture is extracted with ethyl acetate. 4.5 g of N-[1-(4-t-butylphenyl)-3-hydroxy-propyl]-2,6-difluorobenzamide are isolated from the ethyl acetate phase as a crude product having a content of 28% according to GC/MS analysis, which is employed as such in the next reaction step.

Example (IVa-2)

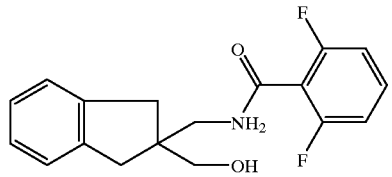

3.24 g of 2-aminomethyl-2-hydroxymethyl-indane are initially introduced into 40 ml of dry chloroform, and 2.73 ml of triethylamine are then added. The mixture is cooled to −10° C. and 3.24 g of 1,6-difluoro-benzoyl chloride, dissolved in 20 ml of dry chloroform, are then added dropwise. The mixture is subsequently stirred at −10° C. for 2 hours and then allowed to come to room temperature. For working up, it is poured onto sodium dihydrogen phosphate solution, the organic phase is separated off and subsequently extracted and the extracts are washed first with sodium dihydrogen phosphate solution and then with bicarbonate solution, dried with Na$_2$SO$_4$ and evaporated. Yield: 5.42 g; melting point 111° C.

Starting Substances of the Formula (V)

Example (V-1)

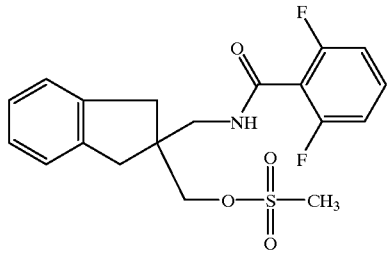

3.75 g of 2-(2,6-difluorobenzamido)methyl-2-hydroxymethyl-indane and 1.64 ml of triethylamine are initially introduced into 47 ml of dry tetrahydrofuran, the mixture is cooled to 0° C. and 1.37 ml of methanesulfonyl chloride are added dropwise. The mixture is stirred at 0° C. for half an hour and then poured onto 200 ml of 5% strength sodium dihydrogen phosphate solution and extracted three times with 100 ml of methylene chloride each time. The combined extracts are dried with $Na_2SO_4$ and evaporated. Residue: 5.5 g of the compound drawn above of the formula (V-1) (83% pure according to HPLC), further used in the next stage without purification.

FORMULATION EXAMPLES (Parts=Parts by Weight)

Formulation Example 1 (Emulsion)

10 parts of the compound according to Example 239, 5 parts of alkyl-arylsulfonate, 5 parts of polyoxyalkylenealkyl-aryl ether and 80 parts of xylene are mixed uniformly to give an emulsion.

Formulation Example 2 (Sprayable Powder)

10 parts of the compound according to Example 116, 5 parts of polyoxyalkylenealkylallyl-sulfuric acid ester salt, 5 parts of ligninsulfonic acid salt, 10 parts of quartz powder and 70 parts of diatomaceous earth are mixed and ground to a sprayable powder.

Formulation Example 3 (Powder)

1 part of the compound according to Example 138, 1 part of quartz sand and 98 parts of finely powdered clay are mixed and ground to a powder.

Formulation Example 4 (Granules)

5 parts of the compound according to Example 50, 0.5 part of dodecylbenzenesulfonate salt, 3.5 parts of ligninsulfonic acid salt, 30 parts of bentonite and 61 parts of talc are mixed, the mixture is kneaded with an appropriate amount of water and granulated with the aid of a granulator and the granules are air-dried in a fluidized bed dryer.

Formulation Example 5 (Free-Flowing Composition)

10 parts of the compound according to Example 154, 5 parts of polyoxyalkylenealkyl-aryl ether, 5 parts of ethylene glycol and 79.6 parts of water are stirred to give a uniform dispersion, and 0.4 part of xanthan solution, as a thickener, is mixed with the dispersion to give a free-flowing composition.

Formulation Example 6 (Free-Flowing Composition)

10 parts of the compound according to Example 445, 2 parts of alkylbenzenesulfonate salt, 3 parts of polyoxyalkylenealkyl-aryl ether, 5 parts of propylene glycol and 79 parts of water are stirred to form a uniform dispersion, 1 part of an antifoam agent is added and the mixture is ground uniformly.

USE EXAMPLES

Example A

Myzus Test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) which are heavily infested with the green peach aphid *Myzus persicae* are treated by being dipped into the preparation of active compound of the desired concentration.

After the specified period of time, the destruction in percent is determined. 100% means that all the aphids have been killed; 0% means that none of the aphids have been killed.

In this test, a degree of destruction of at least 80% is shown after 6 days, for example by the compound of Preparation Example 1 and 17 at an active compound concentration of 0.1%.

Example B

Nephotettix Test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Rice seedlings (*Oryzae sativa*) are treated by being dipped into the preparation of active compound of the desired concentration and are infested with larvae of the green rice leafhopper *Nephotettix cincticeps* while the seedlings are still moist.

After the specified period of time, the destruction in % is determined. 100% means that all the leafhoppers have been killed; 0% means that none of the leafhoppers have been killed.

In this test, a degree of destruction of 100% is shown after 6 days, for example by the compound of Preparation Example 1, 4, 11, 6, 8, 42 and 35 at an active compound concentration of 0.1%.

Example C

Plutella Test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are infested with caterpillars of the diamond-back moth *Plutella maculipennis* while the leaves are still moist.

After the specified period of time, the destruction in % is determined. 100% means that all the caterpillars have been killed; 0% means that none of the caterpillars have been killed.

In this test, a degree of destruction of 80 to 100% is shown after 7 days, for example by the compound of Preparation Example 1, 11, 13, 17, 24 and 42 at an active compound concentration of 0.1%.

Example D

Panonychus Test

Solvent: 3 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with emulsifier-containing water to the desired concentrations.

Plum saplings (*Prunus domestica*) approximately 30 cm high which are heavily infested with all development stages of the fruit tree red spider mite *Panonychus ulmi* are sprayed with a preparation of active compound of the desired concentration.

After the specified period of time, the activity in % is determined. 100% means that all the spider mites have been killed; 0% means that none of the spider mites have been killed.

In this test, a degree of destruction of 100% is shown after 7 days, for example by the compound of Preparation Example 1 at an active compound concentration of 0.02%.

Example E

Tetranychus Test (OP Resistant/Immersion Treatment)

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with emulsifier-containing water to the desired concentrations.

Bean plants (*Phaseolus vulgaris*) which are heavily infested with all development stages of the common red spider mite *Tetranychus urticae* are dipped into a preparation of active compound of the desired concentration.

After the specified period of time, the activity in % is determined. 100% means that all the spider mites have been killed; 0% means that none of the spider mites have been killed.

In this test, a degree of destruction of 98 to 100% is shown after 13 days, for example by the compound of Preparation Example 1 at an active compound concentration of 0.1%.

Example F

Phaedon Larvae Test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of the active compound of the desired concentration and are infested with mustard beetle larvae (*Phaedon cochleariae*), as long as the leaves are still moist.

After the desired time, the destruction in % is determined. 100% means that all the beetle larvae have been killed; 0% means that none of the beetle larvae have been killed.

In this test, a degree of destruction of 100% was shown after 7 days, for example by the compounds of Preparation Examples 17 and 24 at an active compound concentration of, for example, 0.1%.

Example G

Spodoptera Test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of the active compound of the desired concentration and are infested with caterpillars of the owlet moth (*Spodoptera frugiperda*), as long as the leaves are still moist.

After the desired time, the destruction in % is determined. 100% means that all the caterpillars have been killed; 0% means that none of the caterpillars have been killed.

In this test, a destruction of 100% after 7 days was caused, for example by the compound of Preparation Example 24 at an active compound concentration of, for example, 0.1%.

Example H

Tetranychus Test (Ovicidal Action)

A hole is drilled in the lid of an icecream cup (diameter 9 cm) filled with a little water, and through this is inserted a filter paper in the form of a strip, which becomes thoroughly soaked with the water. The leaf of a kidney bean is placed on top.

10 female insects of *Tetranychus urticae* are placed on the leaf, left there for 24 hours to lay eggs and then removed.

The emulsion of Formulation Example 1, diluted with water to an active compound concentration of 500 ppm, is applied and the container is left to stand at a temperature of 25° C. After 7 days, the number of larvae which have hatched is determined under a microscope and the ovicidal action is determined from the equation given below. The test was repeated three times. 2,4-Diphenyl-2-oxazine was used as the comparison substance.

$$\text{Ovicidal action (\%)} = \frac{\text{Number of eggs laid} - \text{number of larvae hatched}}{\text{number of eggs laid}} \times 100$$

The compounds according to the individual Preparation Examples showed the particular ovicidal action stated.

| | | | | |
|---|---|---|---|---|
| 45 = 93% | 46 = 78% | 47 = 95% | 48 = 95% | 49 = 95% |
| 64 = 98% | 74 = 93% | 122 = 95% | 135 = 90% | 140 = 84% |
| 141 = 85% | 142 = 90% | 143 = 87% | 161 = 93% | 162 = 95% |
| 166 = 98% | 177 = 98% | 178 = 98% | 179 = 95% | 233 = 90% |
| 243 = 75% | 244 = 90% | 245 = 93% | 246 = 95% | 264 = 93% |
| 265 = 98% | 298 = 78% | 299 = 90% | 301 = 80% | 302 = 83% |
| 352 = 88% | 353 = 90% | 354 = 90% | 355 = 92% | 357 = 95% |
| 365 = 93% | 366 = 90% | 367 = 93% | 368 = 98% | 370 = 95% |
| 371 = 90% | 373 = 90% | 374 = 83% | 375 = 78% | 376 = 93% |
| 377 = 90% | 378 = 95% | 380 = 98% | 385 = 90% | 387 = 83% |
| 402 = 90% | 412 = 93% | 413 = 78% | 414 = 93% | 419 = 88% |
| 370 = 85% | 421 = 93% | 426 = 88% | 428 = 76% | 429 = 91% |
| 430 = 82% | 431 = 90% | 432 = 87% | 433 = 93% | 434 = 98% |
| 435 = 79% | 436 = 93% | | | |

All the other compounds of Preparation Examples 33 to 448 showed 100% ovicidal action in this test. The comparison substance showed an ovicidal action of only 30%.

Example I

Tetranychus Test (Ovicidal Action)

A hole is drilled in the lid of an icecream cup (diameter 9 cm) filled with a little water, and through this is inserted a filter paper in the form of a strip, which becomes thoroughly soaked with the water. The leaf of a kidney bean is placed on top.

10 female insects of *Tetranychus kanzawai* are placed on the leaf, left there for 24 hours to lay eggs and then removed.

The emulsion of Formulation Example 1, diluted with water to an active compound concentration of 500 ppm, is applied and the container is left to stand at a temperature of 25° C. After 7 days, the number of larvae which have hatched is determined under a microscope and the ovicidal action is determined as in Example H. The test was repeated three times. 2,4-Diphenyl-2-oxazine was used as the comparison substance.

The compounds according to the individual Preparation Examples showed the particular ovicidal action stated.

| | | | | |
|---|---|---|---|---|
| 45 = 95% | 46 = 82% | 48 = 90% | 49 = 98% | 57 = 98% |
| 70 = 95% | 74 = 90% | 86 = 98% | 122 = 95% | 135 = 95% |
| 140 = 85% | 141 = 83% | 142 = 98% | 143 = 95% | 156 = 95% |
| 179 = 98% | 188 = 98% | 233 = 85% | 243 = 80% | 244 = 90% |
| 245 = 95% | 246 = 95% | 265 = 98% | 289 = 95% | 298 = 98% |
| 299 = 95% | 301 = 80% | 332 = 98% | 352 = 95% | 353 = 90% |
| 354 = 93% | 355 = 90% | 365 = 85% | 368 = 98% | 371 = 85% |
| 373 = 93% | 376 = 90% | 375 = 75% | 378 = 85% | 385 = 98% |
| 387 = 85% | 399 = 95% | 413 = 75% | 417 = 95% | 419 = 80% |
| 420 = 85% | 421 = 95% | 428 = 75% | 429 = 95% | 430 = 98% |
| 432 = 85% | 435 = 75% | 442 = 88% | | |

All the other compounds of Preparation Examples 33 to 448 showed 100% ovicidal action in this test. The comparison substance showed an ovicidal action of only 25%.

Example K

Tetranychus Test (Ovicidal Action)

A hole is drilled in the lid of an icecream cup (diameter 9 cm) filled with a little water, and through this is inserted a filter paper in the form of a strip, which becomes completely soaked with the water. The leaf of a kidney bean is placed on top.

10 female insects of *Tetranychus urticae* are placed on the leaf, left there for 24 hours to lay eggs and then removed.

After 8 days at a constant temperature of 25° C., the protonymphs are counted, the emulsion of Formulation Example 1, diluted with water to an active compound concentration of 500 ppm, is applied and the container is left to stand at a temperature of 25° C. After 7 days, the number of insects is determined under a microscope and the destructive action is determined from the following equation. The test was repeated three times. 2,4-Diphenyl-2-oxazine was used as the comparison substance.

$$\text{Destructive action (\%)} = \frac{\text{Number of protonymphs} - \text{number of insects}}{\text{number of protonymphs}} \times 100$$

The compounds according to the individual Preparation Examples showed the particular ovicidal action stated.

| | | | | |
|---|---|---|---|---|
| 46 = 95% | 142 = 98% | 244 = 95% | 245 = 95% | 298 = 85% |
| 299 = 90% | 366 = 98% | 375 = 90% | 377 = 90% | 426 = 95% |
| 442 = 96% | | | | |

All the other compounds of Preparation Examples 33 to 448 showed 100% destructive action in this test. The comparison substance showed a destructive action of only 25%.

Example L

Myzus Test

Seedlings of the Japanese radish in the 2-leaf stage, grown in dishes, are infested with in each case 5 female insects of *Myzus persicae*.

The insects are left there for 3 days to lay larvae, and are then removed.

The emulsion of Formulation Example 1, diluted with water to an active compound concentration of 500 ppm, is applied and the seedlings thus treated are placed in a greenhouse. After 96 hours, the destructive action in % is determined. 100% means that all the insects have been killed, 0% means that none of the insects have been killed. The test is repeated three times. 2,4-Diphenyl-2-oxazine was used as the comparison substance.

The compounds according to the individual Preparation Examples showed the particular destructive action stated in this test:

| | | | | |
|---|---|---|---|---|
| 40 = 63% | 43 = 73% | 44 = 56% | 80 = 92% | 81 = 85% |
| 82 = 78% | 83 = 80% | 86 = 90% | 87 = 88% | 89 = 95% |
| 92 = 98% | 93 = 98% | 103 = 78% | 104 = 95% | 105 = 93% |
| 108 = 67% | 125 = 58% | 138 = 76% | 139 = 63% | 140 = 56% |
| 141 = 60% | 154 = 98% | 179 = 99% | 185 = 94% | 193 = 66% |
| 194 = 93% | 197 = 95% | 217 = 79% | 218 = 63% | 229 = 60% |
| 233 = 75% | 252 = 60% | 288 = 58% | 294 = 67% | 295 = 95% |
| 296 = 98% | 297 = 80% | 298 = 60% | 299 = 56% | 302 = 63% |
| 323 = 79% | 324 = 93% | 326 = 75% | 330 = 69% | 331 = 82% |
| 332 = 93% | 333 = 61% | 338 = 77% | 398 = 98% | |

A 100% destructive action was shown by the compounds of Preparation Examples Nos. 78, 84, 85, 88, 126, 127, 128, 129, 137, 153, 184, 186, 187, 189, 208, 209, 211, 213, 216, 219, 220, 222, 224, 230, 231, 234, 235, 236, 237, 238, 239, 253, 254, 255, 256, 257, 258, 259, 260, 261, 262, 303, 304, 305, 307, 308, 309, 310, 317, 318, 319, 320, 321, 322, 325, 444, 445, 446, 447 and 448, and the comparison substance showed a destructive action of only 13%.

Example M

Aphis Test

Cucumber seedlings in the 1-leaf stage, grown in dishes, are infested with in each case 5 female insects of *Aphis gossypii*. The insects are left there for 3 days to lay larvae, and are then removed.

The emulsion of Formulation Example 1, diluted with water to an active compound concentration of 500 ppm, is applied and the seedlings thus treated are placed in a greenhouse.

After 96 hours, the destructive action in % is determined. 100% means that all the insects have been killed, 0% means that none of the insects have been killed. The test was repeated three times. 2,4-Diphenyl-2-oxazine was used as the comparison substance.

The compounds according to the individual Preparation Examples showed the particular destructive action stated in this test.

| | | | | |
|---|---|---|---|---|
| 43 = 58% | 78 = 67% | 80 = 95% | 81 = 98% | 82 = 80% |
| 83 = 60% | 84 = 56% | 103 = 79% | 104 = 93% | 126 = 75% |

-continued

| | | | | |
|---|---|---|---|---|
| 127 = 69% | 128 = 82% | 129 = 93% | 138 = 90% | 154 = 98% |
| 185 = 90% | 194 = 95% | 197 = 90% | 217 = 85% | 233 = 80% |
| 295 = 98% | 296 = 98% | 297 = 85% | 317 = 95% | 319 = 90% |
| 325 = 85% | | | | |

A 100% destructive action was shown by the compounds of Preparation Examples 1, 33, 34, 35, 36, 37, 38, 39, 85, 86, 87, 88, 89, 92, 93, 105, 137, 153, 179, 184, 186, 187, 189, 208, 209, 211, 213, 216, 219, 220, 222, 224, 230, 231, 234, 235, 236, 237, 238, 239, 253, 254, 255, 256, 257, 258, 259, 260, 261, 262, 303, 304, 305, 307, 308, 309, 310, 318, 320, 321, 322, 323, 324, 326, 331, 332, 338, 398, 444, 445, 446, 447 and 448,
and the comparison substance showed a destructive action of only 6%.

Example N

Nephotettix Test

The emulsion of Formulation Example 1, diluted with water to an active compound concentration of 500 ppm, is applied to rice seedlings grown in pots. After drying, a cylinder of acrylic resin is placed over each pot, each seedling is infested with 10 larvae of Nephotettix cincticeps and the pot is covered with gauze.

The seedlings thus treated are placed in a greenhouse. After 7 days, the destructive action is determined.

100% means that all the larvae have been killed, 0% means that none of the larvae have been killed. The test was repeated three times. 2,4-Diphenyl-2-oxazine was used as the comparison substance.

The compounds according to the individual Preparation Examples showed the particular destructive action stated in this test:

| | | | | |
|---|---|---|---|---|
| 33 = 95% | 34 = 87% | 38 = 93% | 39 = 95% | 44 = 98% |
| 75 = 98% | 76 = 95% | 81 = 90% | 83 = 95% | 92 = 98% |
| 125 = 93% | 130 = 87% | 138 = 95% | 139 = 90% | 183 = 85% |
| 184 = 97% | 241 = 90% | 242 = 95% | 243 = 55% | 263 = 95% |
| 294 = 95% | 299 = 90% | 333 = 67% | 434 = 78% | 438 = 90% |
| 439 = 92% | | | | |

A 100% destructive action was shown by the compounds of Preparation Examples 36, 37, 40, 42, 43, 67, 68, 77, 78, 80, 82, 85, 86, 121, 123, 124, 126, 127, 128, 129, 135, 137, 142, 163, 168, 177, 186, 189, 193, 198, 200, 202, 204, 229, 265, 273, 295, 298, 306, 444, 445, 446, 447 and 448,
and the comparison substance showed no destructive action.

Example O

Nilaparvata Test

The emulsion of Formulation Example 1, diluted with water to an active compound concentration of 500 ppm, is applied to rice seedlings grown in pots. After drying, a cylinder of acrylic resin is placed over each pot, each seedling is infested with 10 larvae of Nilaparvata lugens and the pot is covered with gauze.

The seedlings thus treated are placed in a greenhouse. After 7 days, the destructive action is determined.

100% means that all the larvae have been killed, 0% means that none of the larvae have been killed. The test was repeated three times. 2,4-Diphenyl-2-oxazine was used as the comparison substance.

The compounds according to the individual Preparation Examples showed the particular destructive action stated in this test:

| | | | | |
|---|---|---|---|---|
| 35 = 95% | 42 = 98% | 68 = 95% | 75 = 98% | 76 = 95% |
| 80 = 98% | 83 = 98% | 127 = 95% | 138 = 98% | 142 = 98% |
| 184 = 95% | 189 = 98% | 242 = 95% | 298 = 95% | 447 = 95% |

A 100% destructive action was shown by the compounds of Preparation Examples 33, 36, 37, 39, 40, 41, 43, 44, 67, 77, 78, 82, 85, 86, 92, 130, 123, 124, 126, 128, 129, 135, 137, 163, 168, 177, 186, 193, 198, 200, 202, 204, 229, 263, 265, 273, 294, 295, 296, 306, 444, 445, 446 and 448,
and the comparison substance showed no destructive action.

Test P

Plutella Test

Seedlings of the Japanese radish in the 2-leaf stage, grown in pots, were infested with in each case 15 larvae of Plutella xylostella. The emulsion of Formulation Example 1, diluted with water to an active compound concentration of 500 ppm, is applied. The seedlings thus treated are placed in a greenhouse. After 3 days, the destructive action in % is determined.

100% means that all the larvae have been killed, 0% means that none of the larvae have been killed. The test was repeated three times. 2,4-Diphenyl-2-oxazine was used as the comparison substance.

The compounds according to the individual Preparation Examples showed the particular destructive action stated in this test:

| | | | | |
|---|---|---|---|---|
| 40 = 70% | 41 = 80% | 42 = 75% | 81 = 55% | 120 = 95% |
| 187 = 50% | 188 = 53% | 214 = 98% | 269 = 82% | 281 = 95% |
| 287 = 62% | 316 = 93% | 335 = 95% | 336 = 92% | 337 = 98% |
| 345 = 92% | | | | |

A 100% destructive action was shown by the compounds of Preparation Examples 57, 58, 59, 60, 61, 62, 63, 65, 66, 112, 113, 114, 115, 116, 117, 118, 119, 131, 132, 133, 134, 151, 152, 153, 154, 155, 156, 157, 158, 159, 164, 165, 170, 171, 172, 173, 174, 175, 176, 208, 209, 211, 213, 216, 219, 220, 222, 224, 234, 235, 236, 237, 238, 239, 242, 255, 256, 257, 258, 259, 260, 261, 262, 272, 278, 284, 286, 317 to 326, 330 to 334, 338 to 344, 346, 347 and 444 to 448,
and the comparison substance showed no destructive action.

Test O

Culex Test

The emulsion of Formulation Example 1 is diluted with water to an active compound concentration of 500 ppm. 50 ml portions of this formulation are introduced into 120 ml icecream cups. 20 larvae of Culex pipiens and about 40 mg of yeast, as food, are introduced into each cup. After 7 days, the destructive action in % is determined.

100% means that all the larvae have been killed, 0% means that none of the larvae have been killed. The test was repeated three times. 2,4-Diphenyl-2-oxazine was used as the comparison substance.

The compounds according to the individual Preparation Examples showed the particular destructive action stated in this test:

| | | | | |
|---|---|---|---|---|
| 33 = 83% | 34 = 80% | 38 = 85% | 39 = 92% | 40 = 85% |
| 45 = 80% | 79 = 95% | 84 = 78% | 91 = 82% | 125 = 90% |
| 136 = 85% | 141 = 90% | 192 = 85% | 194 = 85% | 248 = 90% |
| 327 = 78% | 328 = 80% | 329 = 80% | 335 = 75% | 365 = 80% |
| 375 = 83% | 397 = 80% | 405 = 95% | 413 = 78% | 440 = 80% |

All the other compounds of Preparation Examples 33 to 448 showed a destructive action of 100%. The comparison substance showed a destructive action of only 6%.

Example R

Cockroach Test

Test animals: *Periplaneta americana*

Solvent:
35 parts by weight of ethylene glycol monomethyl ether
35 parts by weight of nonylphenol polyglycol ether To produce a suitable formulation, three parts by weight of active compound are mixed with seven parts of the solvent/emulsifier mixture indicated above and the resulting emulsion concentrate is diluted with water to the particular concentration desired.

2 ml of this active compound preparation are pipetted onto filter paper disks (φ 9.5 cm) in Petri dishes of suitable size. After drying the filter disks, 5 test animals of *P. americana* are transferred and the dishes are covered.

After 3 days, the effectiveness of the active compound preparation is determined. 100% means that all the cockroaches have been killed; 0% means that none of the cockroaches have been killed.

In this test, for example the compound of Preparation Example 6 showed a destruction of 100% in an active compound concentration of, for example, 1000 ppm.

Example S

Blowfly Larvae Test

Test animals: *Lucilia cuprina* larvae

Emulsifier:
35 parts by weight of ethylene glycol monomethyl ether
35 parts by weight of nonylphenol polyglycol ether To produce a suitable preparation of active compound, three parts by weight of active compound are mixed with seven parts by weight of the mixture indicated above and the resulting emulsion concentrate is diluted with water to the particular desired concentration.

About 20 *Lucilia cuprina res.* larvae are introduced into a test-tube which contains about 1 cm³ of horse meat and 0.5 ml of the preparation of active compound. After 24 hours, the effectiveness of the active compound preparation is determined. 100% means that all the blowfly larvae have been killed; 0% means that none of the blowfly larvae have been killed.

In this test, a destruction of 100% was caused, for example by the compound of Preparation Examples 24, 316 and 321 at an active compound concentration of, for example, 1000 ppm.

Example T

Nymph Molting Test on Multi-Host Ticks

Test animals: *Amblyomma variegatium*, ticks sucked full

Emulsifier:
35 parts by weight of ethylene glycol monomethyl ether
35 parts by weight of nonylphenol polyglycol ether To produce a suitable formulation, three parts by weight of active compound are mixed with seven parts by weight of the solvent/emulsifier mixture indicated above and the resulting emulsion concentrate is diluted with water to the particular desired concentration.

10 nymphs sucked full are immersed for 1 minute in the active compound preparation to be tested. The animals are transferred to Petri dishes (φ 9.5 cm) containing filter disks and the dishes are covered. After storage for 4 weeks in a climatically controlled room, the molting rate is determined. 100% means that all the animals have molted normally; 0% means that none of the animals have molted normally.

In this test, a molting rate of 0% was caused, for example by the compound of Preparation Example 1 at an active compound concentration of, for example, 1000 ppm.

We claim:

1. An azine derivative of the formula

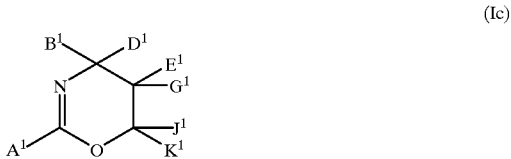

(Ic)

in which

A¹ represents phenyl, which is monosubstituted to pentasubstituted in an identical or different manner by halogen, $C_1$–$C_6$-alkoxy, $C_1$–$C_6$-alkylthio, $C_1$–$C_6$-halogenoalkyl, $C_1$–$C_6$-halogenoalkoxy, $C_1$–$C_6$-halogenoalkylthio, nitro or cyano;

or represents naphthyl, which is optionally monosubstituted to trisubstituted in an identical or different manner, wherein the substituents are halogen, $C_1$–$C_6$-alkyl, $C_1$–$C_6$-alkoxy or $C_1$–$C_6$-halogenoalkoxy;

or represents pyridyl, which is optionally monosubstituted to trisubstituted in identical or different manner, wherein the substituents are halogen, $C_1$–$C_6$-alkyl, $C_1$–$C_6$-alkoxy, $C_1$–$C_6$-halogenoalkyl, $C_1$–$C_6$-halogenoalkoxy or cyano;

or represents thienyl, which is optionally monosubstituted to trisubstituted in an identical or different manner, wherein the substituents are halogen or $C_1$–$C_6$-alkyl;

or represents pyrazolyl, which is optionally monosubstituted to trisubstituted in an identical different manner, wherein the substituents are halogen or $C_1$–$C_3$-alkyl, B¹ represents hydrogen; or represents $C_1$–$C_6$-alkyl, or represents phenyl, benzyl, pheneth-1-yl, pheneth-2-yl, phenoxymethyl, phenylthiomethyl, phenylsulfinylmethyl, phenylsulfonylmethyl, phenylthioeth-1-yl, phenylsulfinyleth-1-yl, phenylsulfonyleth-1-yl, phenoxyeth-1-yl, phenoxyeth-2-yl or styryl, in each case the phenyl moieties recited above are monosubstituted to pentasubstituted in an identical or different manner, and the substituents on the phenyl moieties are halogen
$C_1$–$C_{18}$-alkyl,
$C_1$–$C_8$-alkoxy-$C_1$–$C_8$-alkyl,
$C_1$–$C_8$-halogenoalkoxy, $C_1$–$C_4$-halogenoalkyl,
$C_1$–$C_{18}$-alkoxy, which is optionally interrupted by a further 1 to 3 oxygen atoms,
$C_1$–$C_{18}$-alkylthio,
$C_1$–$C_8$-halogenoalkylthio,
tri-$C_1$–$C_8$-alkylsilyl,
phenyl-di-$C_1$–$C_8$-alkylsilyl,
3,4-difluoromethylenedioxo,
3,4-tetrafluoroethylenedioxo,
a fused-on benzo group,
a fused-on $C_3$–$C_4$-alkanediyl group, benzyliminooxymethyl, which is optionally substituted by $C_1$–$C_4$-alkyl or $C_3$–$C_6$-cycloalkyl or halogen,
cyclohexyl or cyclohexyloxy, in each case optionally substituted by $C_1$–$C_6$-alkyl, $C_1$–$C_6$-alkoxy, cyclohexyl or phenyl,
pyridyloxy, which is optionally monosubstituted or disubstituted in an identical or different manner by halogen, $C_1$–$C_4$-alkyl or $C_1$–$C_4$-halogenoalkyl,
phenyl, phenyl-$C_1$–$C_6$-alkyl, phenoxy, phenylthio, phenyl-$C_1$–$C_6$-alkoxy or benzylthio,
in each case optionally monosubstituted to pentasubstituted in an identical or different manner by $C_1$–$C_{12}$-alkyl, halogen, $C_1$–$C_4$-halogenoalkyl, $C_1$–$C_{12}$-alkoxy, $C_1$–$C_6$-halogenoalkoxy, $C_1$–$C_6$-alkoxy-$C_1$–$C_6$-alkyl, $C_1$–$C_6$-alkoxy-ethyleneoxy, $C_1$–$C_6$-alkylthio or $C_1$–$C_6$-halogenoalkylthio,
$D^1$ represents hydrogen or methyl,
$E^1$ represents hydrogen, methyl or phenyl, phenyl-$C_1$–$C_6$-alkyl, phenoxy-$C_1$–$C_6$-alkyl, phenylthio-$C_1$–$C_6$-alkyl, phenylsulfinyl-$C_1$–$C_6$-alkyl or phenylsulfonyl-$C_1$–$C_6$-alkyl, in each case the phenyl moieties recited above are monosubstituted to tetrasubstituted in an identical or different manner, wherein the substituents on the phenyl moieties are the same as the substituents recited for the phenyl moieties recited in the definition of substituent $B^1$,
$G^1$ represents hydrogen or methyl,
$J^1$ represents hydrogen or methyl,
$K^1$ represents hydrogen or methyl, or represents phenyl, which is monosubstituted to tetrasubstituted in an identical or different manner by the substituents mentioned for the phenyl moieties recited in connection with the definition of $B^1$, or
$B^1$ and $D^1$ together represent 2- and 6-membered alkanediyl, which is optionally monosubstituted to tetrasubstituted in an identical or different manner, wherein one or two $CH_2$ groups are optionally replaced by O or S, wherein the substituents are
$C_1$–$C_4$-alkyl, and optionally substituted phenyl or an optionally substituted fused-on benzo group, which when substituted are monosubstituted to tetrasubstituted in an identical or different manner, wherein the optional substituents are the substituents mentioned for the phenyl moieties recited in connection with the definition of substituent $B^1$, or
$D^1$ and $G^1$ represent 2- to 6-membered alkanediyl, which is optionally monosubstituted to tetrasubstituted in an identical or different manner, wherein one or two $CH_2$ groups are optionally replaced by O or S, wherein the substituents are
$C_1$–$C_4$-alkyl, and optionally substituted phenyl or an optionally substituted fused-on benzo group, which when substituted are monosubstituted to tetrasubstituted in an identical or different manner, wherein the optional substituents are the substituents mentioned for the phenyl moieties recited in connection with the definition of substituent $B^1$, or
$E^1$ and $G^1$ together represent 2- to 6-membered alkanediyl, which is optionally monosubstituted to tetrasubstituted in an identical or different manner, wherein one or two $CH_2$ groups are optionally replaced by O or S, wherein the substituents are
$C_1$–$C_4$-alkyl, and optionally substituted phenyl or an optionally substituted fused-on benzo group, which when substituted are monosubstituted to tetrasubstituted in an identical or different manner, wherein the optional substituents are the substituents mentioned for the phenyl moieties recited in connection with the definition of substituent $B^1$, and
with the proviso that at least one of the substituents $B^1$, $D^1$, $E^1$, $G^1$, $J^1$ and $K^1$ does not represent hydrogen or alkyl,
provided that $J^1$ does not represent methyl when $K^1$ represents methyl or hydrogen and further provided that $D^1$ does not represent methyl when $B^1$ represents alkyl or hydrogen.

2. An azine derivative according to claim 1, in which
$A^1$ represents phenyl, which is monosubstituted to pentasubstituted in an identical or different manner by
F, Cl, Br, $C_1$–$C_3$-alkoxy, $C_1$–$C_3$-alkylthio, $C_1$–$C_2$-alkyl which is monosubstituted to pentasubstituted in an identical or different manner by F or Cl, $C_1$–$C_4$-alkoxy which is monosubstituted to pentasubstituted in an identical or different manner by F or Cl, $SCF_3$, $SCHF_2$, nitro or cyano;
or represents naphthyl, which is optionally monosubstituted to trisubstituted in an identical or different manner, wherein the substituents are
F, Cl, $C_1$–$C_6$-alkyl, $C_1$–$C_6$-alkoxy or $C_1$–$C_6$-alkoxy which is monosubstituted to trisubstituted in an identical or different manner by F or Cl;
or represents pyridyl, which is optionally monosubstituted to disubstituted in an identical or different manner, wherein the substituents are F, Cl, $C_1$–$C_3$-alkyl, $C_1$–$C_3$-alkoxy, $CF_3$, $OCF_3$ or cyano;
or represents thienyl, which is optionally monosubstituted to disubstituted in an identical or different manner, wherein the substituents are Cl, Br, $CH_3$ or $C_2H_5$;
or represents pyrazolyl, which is optionally monosubstituted to trisubstituted in an identical or different manner, wherein the substituents are F, Cl, Br or $C_1$–$C_3$-alkyl,
$B^1$ represents hydrogen; or represents $C_1$–$C_4$-alkyl; or represents phenyl, benzyl, pheneth-1-yl, pheneth-2-yl, phenoxymethyl, phenylthiomethyl, phenylsulfinylmethyl, phenylsulfonylmethyl, phenylthioeth-1-yl, phenylsulfinyleth-1-yl, phenylsulfonyleth-1-yl, phenoxyeth-1-yl, phenoxyeth-2-yl or styryl, in each case the phenyl moieties recited above are monosubstituted to pentasubstituted in an identical or different manner, wherein the substituents on the phenyl moieties are
F, Cl, Br,
$C_1$–$C_{18}$-alkyl,
$C_1$–$C_6$-alkoxy-$C_1$–$C_8$-alkyl,
$C_1$–$C_8$-alkoxy which is monosubstituted to hexasubstituted in an identical or different manner by F or Cl,
$C_1$–$C_2$-alkyl which is monosubstituted to pentasubstituted in an identical or different manner by F or Cl,
$C_1$–$C_{18}$-alkoxy and —$(OC_2H_4)_{1-3}$-O-$C_1$–$C_6$-alkyl, $C_1$–$C_{15}$-alkylthio,
$C_1$–$C_8$-alkylthio which is monosubstituted to hexasubstituted in an identical or different manner by F or Cl,
tri-$C_1$–$C_6$-alkylsilyl,
phenyl-di-$C_1$–$C_6$-alkylsilyl,
3,4-difluoromethylenedioxo,
3,4-tetrafluoroethylenedioxo,
a fused-on benzo group,
a fused-on $C_4$-alkanediyl group,
the groups

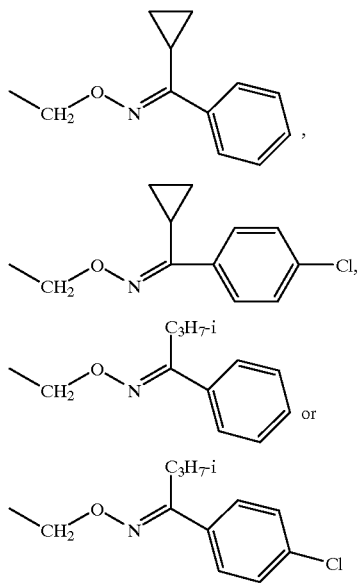

cyclohexyl or cyclohexyloxy, in each case optionally substituted by $C_1$–$C_4$-alkyl, $C_1$–$C_4$-alkoxy, cyclohexyl or phenyl,
pyridyloxy, which is optionally monosubstituted or disubstituted in an identical or different manner by F, Cl or $CF_3$,
phenyl, phenyl-$C_1$–$C_6$-alkyl, phenoxy, phenylthio, phenyl-$C_1$–$C_6$-alkoxy or benzylthio, in each case optionally monosubstituted to pentasubstituted in an identical or different manner by
$C_1$–$C_{12}$-alkyl, F, Cl, Br, $C_1$–$C_4$-alkyl which is monosubstituted to hexasubstituted by F or Cl, $C_1$–$C_{12}$-alkoxy, $C_1$–$C_4$-alkoxy which is monosubstituted to hexasubstituted in an identical or different manner by F or Cl,
$C_1$–$C_4$-alkoxy-$C_1$–$C_4$-alkyl, $C_1$–$C_4$-alkoxy-ethyleneoxy, $C_1$–$C_4$-alkylthio, or $C_1$–$C_4$-alkylthio which is monosubstituted to hexasubstituted in an identical or different manner by F or Cl,
$D^1$ represents hydrogen or methyl,
$E^1$ represents hydrogen, methyl or phenyl, phenyl-$C_1$–$C_4$-alkyl, phenoxy-$C_1$–$C_4$-alkyl, phenylthio-$C_1$–$C_4$-alkyl, phenylsulfinyl-$C_1$–$C_4$-alkyl or phenylsulfonyl-$C_1$–$C_4$-alkyl, in each case the phenyl moieties recited above are monosubstituted to tetrasubstituted in an identical or different manner wherein the substituents on the phenyl moieties are the same as the substituents recited for the phenyl moieties recited in the definition of substituent $B^1$,
$G^1$ represents hydrogen or methyl,
$J^1$ represents hydrogen or methyl,
$K^1$ represents hydrogen or methyl, or represents phenyl, which is monosubstituted to tetrasubstituted in an identical or different manner by the substituents mentioned for phenyl moieties recited in connection with the definition of $B^1$, or
$B^1$ and $D^1$ together represent 2- to 6-membered alkanediyl, which is optionally monosubstituted to tetrasubstituted in an identical or different manner, wherein one or two $CH_3$ groups are optionally replaced by O or S, wherein the substituents are
$C_1$–$C_4$-alkyl, and optionally substituted phenyl or an optionally substituted fused-on benzo group, which when substituted are monosubstituted to tetrasubstituted in an identical or different manner, wherein the optional substituents are the substituents mentioned for the phenyl moieties recited in connection with the definition of substituent $B^1$, or
$D^1$ and $G^1$ together represent 2- to 6-membered alkanediyl, which is optionally monosubstituted to tetrasubstituted in an identical or different manner, wherein one or two $CH_2$ groups are optionally replaced by O or S, wherein the substituents are
$C_1$–$C_4$-alkyl, and optionally substituted phenyl or an optionally substituted fused-on benzo group, which when substituted are monosubstituted to tetrasubstituted in an identical or different manner, wherein the optional substituents are the substituents mentioned for the phenyl moieties recited in connection with the definition of substituent $B^1$, or
$E^1$ and $G^1$ together represent 2- to 6-membered alkanediyl, which is optionally monosubstituted to tetrasubstituted in an identical or different manner, wherein one or two $CH_2$ groups are optionally replaced by O or S, wherein the substituents are
$C_1$–$C_4$-alkyl, and optionally substituted phenyl or an optionally substituted fused-on benzo group, which when substituted are monosubstituted to tetrasubstituted in an identical or different manner, wherein the optional substituents are the substituents mentioned for the phenyl moieties recited in connection with the definition of substituent $B^1$, or
with the proviso that at least one of the substituents $B^1$, $D^1$, $E^1$, $G^1$, $J_1$ and $K^1$ does not represent hydrogen or alkyl.

3. An azine derivative as claimed in claim 1, in which
$A^1$ represents phenyl, which is monosubstituted to pentasubstituted in an identical or different manner by
F, Cl, Br, $C_1$–$C_3$-alkoxy, $C_1$–$C_3$-alkylthio, $C_1$–$C_2$-alkyl which is monosubstituted to pentasubstituted in an identical or different manner by F or Cl, $C_1$–$C_4$-alkoxy which is monosubstituted to pentasubstituted in an identical or different manner by F or Cl, $SCF_3$, $SCHF_2$, nitro or cyano;
$B^1$ represents hydrogen; or represents $C_1$–$C_4$-alkyl; or represents phenyl, benzyl, pheneth-1-yl, pheneth-2-yl, phenoxymethyl, phenylthiomethyl, phenylsulfinylmethyl, phenylsulfonylmethyl, phenylthioeth-1-yl, phenylsulfinyleth-1-yl, phenylsulfonyleth-1-yl, phenoxyeth-1-yl, phenoxyeth-2-yl or styryl, wherein the phenyl moieties recited above are in each case monosubstituted to pentasubstituted in identical or different manner, and the substituents on the phenyl moieties are
F, Cl, Br,
$C_1$–$C_{18}$-alkyl,
$C_1$–$C_6$-alkoxy-$C_1$–$C_8$-alkyl, $C_1$–$C_8$-alkoxy which is monosubstituted to hexasubstituted in an identical or different manner by F or Cl, $C_1$–$C_2$-alkyl which is monosubstituted to pentasubstituted in an identical or different manner by F or Cl,
$C_1$–$C_{18}$-alkoxy and —$(OC_2H_4)_{1-3}$-O-$C_1$–$C_6$-alkyl,
$C_1$–$C_{15}$-alkylthio,
$C_1$–$C_8$-alkylthio which is monosubstituted to hexasubstituted in an identical or different manner by F or Cl,
tri-$C_1$–$C_6$-alkylsilyl,
phenyl-di-$C_1$–$C_6$-alkylsilyl,
3,4-difluoromethylenedioxo,
3,4-tetrafluoroethylenedioxo,
a fused-on benzo group,
a fused-on $C_4$-alkanediyl group,
the groups

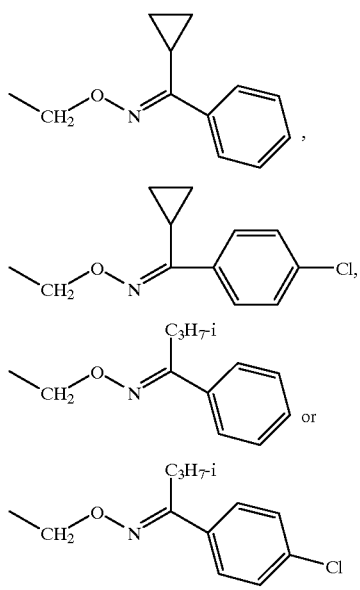

cyclohexyl or cyclohexyloxy, in each case optionally substituted by $C_1$–$C_4$-alkyl, $C_1$–$C_4$-alkoxy, cyclohexyl or phenyl,
pyridyloxy which is optionally monosubstituted or disubstituted in an identical or different manner by F, Cl or CF,
phenyl, phenyl-$C_1$–$C_6$-alkyl, phenoxy, phenylthio, phenyl-$C_1$–$C_6$-alkoxy or benzylthio, in each case optionally monosubstituted to pentasubstituted in an identical or different manner by
$C_1$–$C_{12}$-alkyl, F, Cl, Br, $C_1$–$C_4$-alkyl which is monosubstituted to hexasubstituted by F or Cl, $C_1$–$C_{12}$-alkoxy, $C_1$–$C_4$-alkoxy which is monosubstituted to hexasubstituted in an identical or different manner by F or Cl,
$C_1$–$C_4$-alkoxy-$C_1$–$C_4$-alkyl, $C_1$–$C_4$-alkoxyethyleneoxy, $C_1$–$C_4$-alkylthio or $C_1$–$C_4$-alkylthio which in monosubstituted to hexasubstituted in an identical or different manner by F or Cl,
$D^1$ represents hydrogen or methyl,
$E^1$ represents hydrogen or methyl, or phenyl, phenyl-$C_1$–$C_4$-alkyl, phenoxy-$C_1$–$C_4$-alkyl, phenylthio-$C_1$–$C_4$-alkyl, phenylsulfinyl-$C_1$–$C_4$-alkyl or phenylsulfonyl-$C_1$–$C_4$-alkyl, in each case the phenyl moieties recited above are monosubstituted to tetrasubstituted in an identical or different manner wherein the substituents on the phenyl moieties are the same as the substituents recited for the phenyl moieties recited in the definition of substituent $B^1$, $G^1$ represents hydrogen or methyl,
$J^1$ represents hydrogen or methyl,
$K^1$ represents hydrogen or methyl, or represents phenyl, which is monosubstituted to tetrasubstituted in an identical or different manner by the substituents mentioned for the phenyl moieties recited in connection with the definition of $B^1$, or
$B^1$ and $D^1$ together represent 2- to 6-membered alkanediyl which is optionally monosubstituted to tetrasubstituted in an identical or different manner, wherein one or two $CH_2$ groups are optionally replaced by O or S, wherein the substituents are
  $C_1$–$C_4$-alkyl, and optionally substituted phenyl or an optionally substituted fused-on benzo group, which when substituted are monosubstituted to tetrasubstituted in an identical or different manner, wherein the optional substituents are the substituents mentioned for the phenyl moieties recited in connection with the definition of substituent $B^1$,
$D^1$ and $G^1$ together represent 2- to 6-membered alkanediyl which is optionally monosubstituted to tetrasubstituted in an identical or different manner, wherein one or two $CH_2$ groups are optionally replaced by O or S, wherein the substituents are
  $C_1$–$C_4$-alkyl, and optionally substituted phenyl or an optionally substituted fused-on benzo group, which when substituted are nonosubstituted to tetrasubstituted in an identical or different manner, wherein the optional substituents are the substituents mentioned for the phenyl moieties recited in connection with the definition of substituent $B^1$, or
$E^1$ and $G^1$ together represent 2- to 6-membered alkanediyl which is optionally monosubstituted to tetrasubstituted in an identical or different manner, wherein one or two $CH_2$ groups are optionally replaced by O or S, wherein the substituents are
  $C_1$–$C_4$-alkyl, and optionally substituted phenyl or an optionally substituted fused-on benzo group, which when substituted are monosubstituted to tetrasubstituted in an identical or different manner, wherein the optional substituents are the substituents mentioned for the phenyl moieties recited in connection with the definition of substituent $B^1$,
with the proviso that at least one of the substituents $B^1$, $D^1$, $E^1$, $G^1$, $J^1$ and $K^1$ does not represent hydrogen or alkyl.

4. An azine derivative of the formula (Ia-4)

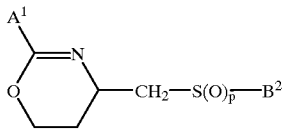

in which
$A^1$ represents the meanings given in claim 1 and
p represents 0,1 or 2 and
$B^2$ represents phenyl which is monosubstituted to tetrasubstituted in an identical or different manner, wherein the substituents are the substituents for the phenyl moieties recited in claim 1 under $B^1$.

5. An azine derivative of the formula

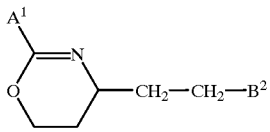

(Ia-5)

in which $A^1$ represents the meanings given in claim 1 and $B^2$ represents phenyl which is monosubstituted to tetrasubstituted in an identical or different manner, wherein the substituents are the substituents for the phenyl moieties recited in claim 1 under $B^1$.

6. An azine derivative of the formula

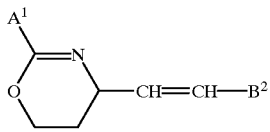

(Ia-6)

in which $A^1$ represents the meanings given in claim 1 and $B^2$ represents phenyl which is monosubstituted to tetrasubstituted in an identical or different manner, wherein the substituents are the substituents for the phenyl moieties recited in claim 1 under $B^1$.

7. An azine derivative of the formula

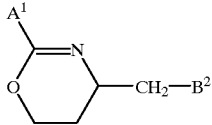

(Ia-7)

in which $A^1$ represents the meanings given in claim 1 and $B^2$ represents phenyl which is monosubstituted to tetrasubstituted in an identical or different manner, wherein the substituents are the substituents for the phenyl moieties recited in claim 1 under $B^1$.

8. An azine derivative of the formula

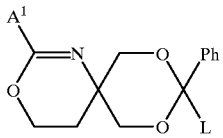

(Ia-10)

in which $A^1$ represents the meanings given in claim 1,

L represents hydrogen or methyl and

Ph represents phenyl which is optionally monosubstituted to tetrasubstituted in an identical or different manner, wherein the substituents are the substituents for the phenyl moieties recited in claim 1 under $B^1$.

9. An azine derivative of the formula

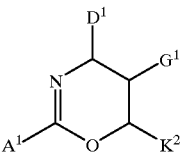

(Ia-15)

in which $A^1$, $D^1$ and $G^1$ represent the meanings given in claim 1 and $K^2$ represents phenyl which is monosubstituted to tetrasubstituted in an identical or different manner, wherein the substituents are the substituents for the phenyl moieties recited in claim 1 under $B^1$.

10. An azine derivative of the formula

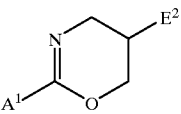

(Ia-16)

in which $A^1$ represent the meanings given in claim 1 and $E^2$ represents phenyl which is monosubstituted to tetrasubstituted in an identical or different manner, wherein the substituents are the substituents for the phenyl moieties recited in claim 1 under $B^1$.

11. A compound according to claim 1, wherein such compound is

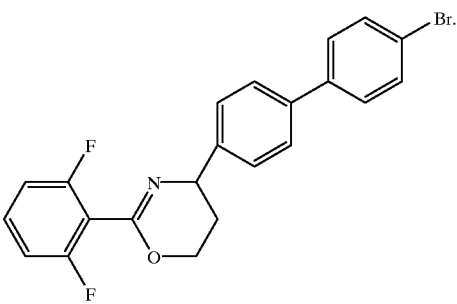

12. An azine derivative according to claim 1, wherein $J^1$ represents hydrogen.

13. An azine derivative according to claim 1, wherein $D^1$ represents hydrogen.

14. An azine derivative according to claim 1, wherein $B^1$, $K^1$ or $G^1$ and $D^1$ together, $D^1$ and $G^1$ together $E^1$ and $G^1$ together present a radical which is substituted by tri-$C_1$–$C_8$-alkylsilyl.

15. A process for the preparation of an azine derivative of the formula (Ia) as claimed in claim 1, which comprises a) reacting an aminoalcohol of the formula

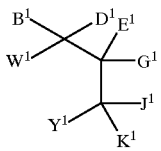
(II)

in which $B^1$, $D^1$, $E^1$, $G^1$, $J^1$ and $K^1$ have the meanings given in claim 1;

$W^1$ represents amino and $Y^1$ represents hydroxyl;

or $W^1$ represents hydroxyl and $Y^1$ represents amino;

with a carboxylic acid of the formula $$A^1-COOH \qquad (III)$$

in which $A^1$ has the meaning given in claim 1;

with a dehydrating agent, optionally in the presence or a diluent;

or b) reacting an amide-alcohol of the formula

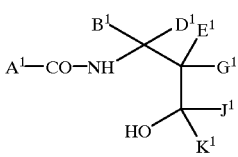
(IVa)

or

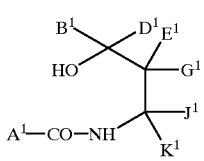
(IVb)

in which $A^1$, $B^1$, $D^1$, $E^1$, $G^1$, $J^1$ and $K^1$ have the meanings given in claim 1, with a dehydrating agent, optionally in the presence or a diluent;

or c) reacting an amide derivative of the formula

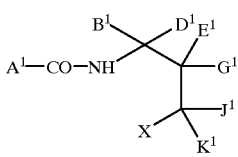
(Va)

or

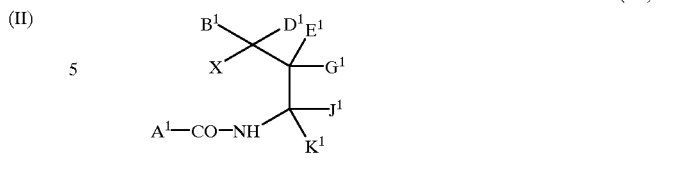
(Vb)

in which $A^1$, $B^1$, $D^1$, $E^1$, $G^1$, $J^1$ and $K^1$ have the meanings given in claim 1, and X represents halogen, alkylsulfonyloxy or arylsulfonyloxy, with a dehydrating agent, optionally in the presence or a diluent;

or d) reacting an amide-alcohol of the formula

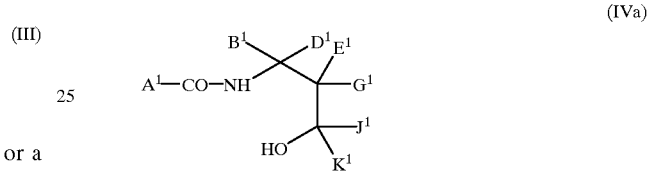
(IVa)

or

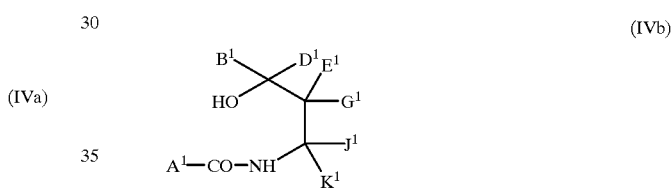
(IVb)

in which $A^1$, $B^1$, $D^1$, $E^1$, $G^1$, $J^1$ and $K^1$ have the meanings given in claim 1, with a thienylating agent, optionally in the presence of a diluent.

16. A pesticidal composition comprising a pesticidally effective amount of compound according to claim 1 and a diluent.

17. A method of combatting pests which comprises applying to such pests or to a locus from which it is desired to exclude such pests an amount effective therefor of a compound according to claim 1.

18. The method according to claim 17, wherein such compound is

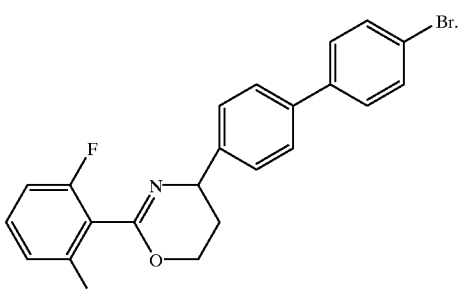

19. An azine derivative of the formula,

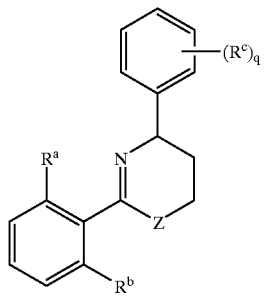
(Ia-30)

in which $R^a$ represents hydrogen, fluorine or chlorine, $R^b$ represents fluorine or chlorine, q represents a number from 0 to 5, $R^c$ represents $C_1$–$C_{15}$-alkyl, $C_1$–$C_{15}$-alkoxy, $C_1$–$C_{10}$-alkylthio, halogen, lower halogenoalkyl, lower halogenoalkoxy or tri(lower alkyl)silyl, or represents $C_3$–$C_7$-cycloalkyl, which is optionally monosubstituted to trisubstituted by lower alkyl, or represents

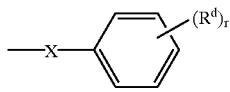

in which

X represents a direct bond, oxygen, lower alkanediyl, lower alkanediyloxy or di (lower alkyl)silyl, r represents a number from 0 to 5, $R^d$ represents $C_1$–$C_{12}$-alkyl, $C_1$–$C_{12}$-alkoxy, halogen, lower halogenoalkyl, lower halogenoalkoxy or tri (lower alkyl)silyl and Z represents oxygen.

20. A compound according to claim 19, wherein $R^c$ represents

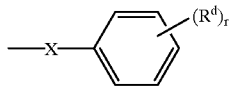

in which

X represents a direct bond and $R^d$ represents halogen, lower halogenoalkyl, and lower halogenoalkoxy.

* * * * *

UNITED STATES PATENT AND TRADEMARK OFFICE
CERTIFICATE OF CORRECTION

PATENT NO. : 6,166,010
DATED : December 26, 2000
INVENTOR(S) : Itoh et al.

It is certified that error appears in the above-identified patent and that said Letters Patent is hereby corrected as shown below:

<u>Column 171,</u>
Line 44, delete "CF" and substitute -- $CF_3$ --

Signed and Sealed this

Twenty-sixth Day of February, 2002

Attest:

JAMES E. ROGAN
*Attesting Officer*     *Director of the United States Patent and Trademark Office*